United States Patent
Basser et al.

(10) Patent No.: US 6,289,753 B1
(45) Date of Patent: Sep. 18, 2001

(54) METHOD FOR MEASURING MECHANICAL PROPERTIES OF THE COLLAGEN NETWORK IN CARTILAGE

(75) Inventors: Peter J. Basser, Washington, DC (US); Alice Maroudas, Haifa (IL)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/367,360

(22) PCT Filed: Feb. 13, 1998

(86) PCT No.: PCT/US98/02727

§ 371 Date: Aug. 11, 1999

§ 102(e) Date: Aug. 11, 1999

(87) PCT Pub. No.: WO98/36276

PCT Pub. Date: Aug. 20, 1998

Related U.S. Application Data

(60) Provisional application No. 60/038,005, filed on Feb. 14, 1997.

(51) Int. Cl.[7] ............................................... G01N 33/483
(52) U.S. Cl. ............................................................. 73/866
(58) Field of Search .............................. 73/866, 73, 760; 600/587

(56) References Cited

U.S. PATENT DOCUMENTS

| 4,967,764 | * | 11/1990 | Basser . |
| 5,433,215 | * | 7/1995 | Athanasiou et al. . |
| 5,521,087 | * | 5/1996 | Lee et al. . |

FOREIGN PATENT DOCUMENTS

WO 91/09568 * 7/1991 (WO) .

* cited by examiner

Primary Examiner—Robert Raevis
(74) Attorney, Agent, or Firm—Morgan & Finnegan, L.L.P.

(57) ABSTRACT

A method for measuring the mechanical integrity of a collagen network in cartilage and of other extracellular matrices according to applying a known mechanical stress to the sample; measuring a quantity representing hydration of the sample; and providing the extracellular network recoil pressure according to the known applied mechanical stress and the independently determined proteoglycan osmotic pressure corresponding to the hydration. In accordance with an embodiment of the present invention, an in vitro mechanowsmotic titration method for determining the collagen network tension (i.e., recoil pressure) for a given collagen network hydration is used. In accordance with a further embodiment of the present invention, the method may be used for diagnosing and/or monitoring the progression of diseases, such as osteoarthritis, preferably according to the collagen network stiffness, which for example, is shown to be reduced in osteoardritic cartilage compared with normal cartilage.

13 Claims, 18 Drawing Sheets

O, o, · Solutes of different sizes

| AGE (years) | H2O/dry (gm/gm) | $(V_t-V_c)/N_c$ | FCD/wet wt. (meq/gm) | FCD/dry wt. (meq/gm) | FCD/coll wt. (meq/gm) | FCD$_{eff}$ (meq/gm) | $P_c=\pi_{PG}$ (atm) |
|---|---|---|---|---|---|---|---|
| 90 n=8 | 1.90±0.10 | 5.75±0.11 | 0.201±0.003 | 0.584±0.016 | 1.12±0.05 | 0.401±0.009 | 4.46±0.23 |
| 55 n=7 | 2.01±0.08 | 5.90±1.39 | 0.178±0.019 | 0.540±0.057 | 1.00±0.12 | 0.360±0.014 | 3.65±0.41 |
| 40 n=2 | 2.45±0.04 | 5.92±0.05 | 0.154±0.013 | 0.528±0.049 | 0.86±0.07 | 0.276±0.025 | 2.45±0.48 |
| mean n=17 | 2.01±0.23 | 5.83±0.63 | 0.187±0.015 | 0.559±0.063 | 1.04±0.11 | 0.376±0.072 | 3.89±0.54 |
| 90 after trypsin treatment n=4 | 2.13±0.14 | 5.55±0.21 | 0.128±0.009 | 0.402±0.017 | 0.68±0.05 | 0.262±0.043 | 2.19±0.24 |
| gross Fibr | 4.56 | 10.29 | 0.094 | 0.52 | 0.83 | 0.37 | 0.86 |
| surf. Fibr | 3.52 | 6.81 | 0.080 | 0.36 | 0.47 | 0.138 | 0.86 |
| OA surf. fibr | 3.44 | 9.61 | 0.122 | 0.54 | 1.03 | 0.190 | 1.37 |
| surf. fibr | 3.64 | 7.96 | 0.123 | 0.57 | 0.87 | 0.200 | 1.48 |
| mean | 3.79±0.35 | 8.67±1.81 | 0.105±0.018 | 0.50±0.07 | 0.80±0.23 | 0.166±0.034 | 1.1±0.34 |

The difference in $P_c$ between the normal specimens and OA specimens is highly significant (P < 0.0005). The difference in $P_c$ amongst the normal specimens of different ages are also highly significant (P < 0.0025).

FIG. 11

| gm PEG per 100 gm H$_2$O | $\pi_{PEG}$ (atm) | M$_0$ (gm) | M/M$_0$ | m$_{tot}$ H$_2$O (gm) | F (gm IF water per gm collagen) | m$_{IF}$ H$_2$O (gm) | m$_{EF}$ H$_2$O (gm) | FCD$_{total}$ (meq per gm tissue) | FCD$_{eff}$ (meq per gm EF water) | $\pi_{PG}$ (atm) | P$_c$ (atm) | V$_{tot}$/V$_c$ | (V$_{tot}$-V$_c$)/V$_c$ |
|---|---|---|---|---|---|---|---|---|---|---|---|---|---|
| 0 | 0 | .01880 | 1 | .01252 | .8826 | .00288 | .00964 | .203 | .396 | 4.42 | 4.42 | 7.01 | 6.01 |
| 8 | 0.88 | .01879 | 1 | .01252 | .8826 | .00288 | .00964 | .203 | .396 | 4.42 | 3.54 | 7.01 | 6.01 |
| 10 | 1.10 | .01868 | .994 | .01240 | .8794 | .00287 | .00953 | .203 | .400 | 4.49 | 3.39 | 6.96 | 5.96 |
| 12 | 1.57 | .01842 | .980 | .01216 | .8715 | .00284 | .00932 | .203 | .410 | 4.68 | 3.11 | 6.86 | 5.86 |
| 15 | 2.45 | .01805 | .960 | .01177 | .8603 | .00281 | .00896 | .203 | .425 | 4.98 | 2.53 | 6.70 | 5.70 |
| 20 | 4.38 | .01745 | .928 | .01119 | .8416 | .00274 | .00845 | .203 | .452 | 5.53 | 1.15 | 6.46 | 5.46 |
| 20 | 4.38 | .01712 | .910 | .01084 | .8302 | .00271 | .00813 | .203 | .470 | 5.91 | 1.53 | 6.33 | 5.33 |
| 25 | 6.89 | .01600 | .85 | .00972 | .7957 | .00259 | .00713 | .203 | .536 | 7.42 | 0.53 | 5.86 | 4.86 |
| 27 | 8.05 | .01556 | .82 | .00938 | .7857 | .00256 | .00682 | .203 | .560 | 8.02 | 0 | 5.72 | 4.72 |

M$_0$ - Initial wet tissue weight after equilibration in 0.15 M NaCl solution; M - Wet tissue weight after equilibration in PEG solution; F - is defined as the ratio : m$_{IF}$ H$_2$O / m$_0$

FIG. 12

| | | | |
|---|---|---|---|
| Initial wet weight of specimen, $M_0$ | (gm) | 0.01880 | measured |
| Dry weight of specimen, $m_{dry}$ | (gm) | 0.00628 | measured |
| Weight of water, $m_{tot\ H_2O}$ | (gm) | 0.01252 | calculated |
| Collagen weight, $m_c$ | (gm) | 0.00326 | measured |
| $v_c = 0.74\ cm^3/gm\ (40)$ | | | |
| Collagen volume, $V_c$ | ($cm^3$) | 0.00241 | calculated (40) |
| *GAG weight, $m_{GAG}$ | (gm) | 0.00115 | from previous data |
| $V_{GAG} = 0.54\ cm^3/gm\ (39)$ | | | |
| GAG volume, $V_{GAG}$ | ($cm^3$) | 0.00060 | calculated (39) |
| Total dry tissue volume $V_{dry}$ ($V_{dry} = V_{total\ protein} + V_{GAG}$) | ($cm^3$) | 0.00441 | calculated |
| Total tissue volume, $V_{tot}$ ($V_{tot} = V_{dry} - V_{tot\ H_2O}$) | ($cm^3$) | 0.01629 | calculated |

- *Mean GAG content was taken as 19% by dry weight, value typical of middle zone non-fibrillated elderly human femoral head cartilage and consistent with present FCD measurements (author's unpublished data, also (58))
- Non-collagenous proteins comprise both PG protein and other matrix proteins.
- The mean density of non-collagenous proteins in cartilage was taken as 1.35 gm/cm³ which is similar to those reported for other non-collagenous proteins (38).

FIG. 13

| PG solution | collagen network |
|---|---|
| compressibility: $k_G = V \dfrac{-d\pi_{PG}}{dV} = \dfrac{-d\pi_{PG}}{d\ln(V)}$ | $k_c = V \dfrac{dP_c}{dV} = \dfrac{dP_c}{d\ln(V)}$ |
| distensibility: $-\pi_{PG} \dfrac{dV}{d\pi_{PG}} = \dfrac{-dV}{d\ln(\pi_{PG})}$ | $T_c \dfrac{dV}{dP_c} = \dfrac{dV}{d\ln(P_c)}$ |
| "elasticity": $e_\pi = \dfrac{-d\ln(V)}{d\ln(\pi_{PG})} = \dfrac{-\pi_{PG}}{V} \dfrac{dV}{d\pi_{PG}}$ | $e_p = \dfrac{d\ln(V)}{d\ln(P_c)} = \dfrac{P_c}{V} \dfrac{dV}{dP_c}$ |

FIG. 18

METHOD FOR MEASURING MECHANICAL PROPERTIES OF THE COLLAGEN NETWORK IN CARTILAGE

This application claim benefit to provisional application No. 60/038,005 filed Feb. 14, 1997.

TECHNICAL FIELD

The present invention relates generally to assessing mechanical integrity of extracellular matrices such as cartilage and, more particularly, to a method for measuring the mechanical integrity of the collagen network in cartilage, and for modeling and assessing cartilage according to the measured collagen network mechanical properties.

BACKGROUND OF THE INVENTION

Since Ogston first proposed a model of connective tissue consisting of "a relatively coarse fibrous collagen network" that balances the osmotic pressure of a "molecular network of polysaccharide fibers trapped within it", surprisingly little work has been done to use it to study the behavior of cartilage. (Ogston, A. G. (1970) in Chemistry and Molecular Biology of the Intracellular Matrix: The biological functions of the glycosaminoglycans Eds. (13alazs, E. A., Eds.), pp. 1231–1240, Academic Press, London).

Subsequent studies have been performed to measure the proteoglycan (PG) osmotic pressure, $\pi_{PG}$, in normal and osteoarthritic (OA) cartilage specimens, yet, no comparable quantitative methods have been developed to characterize the integrity of the collagen network per se, such as its ability to "restrain" the PGs from swelling. See, Maroudas, A., Bayliss, M. T., and Venn, M. F. (1980) Ann Rheum Dis 39, 514–23; Grushko, G., Schneiderman, R., and Maroudas, A. (1989) Connective Tissue Research 19, 149–176; and Maroudas, A., Ziv, I., Weisman, N., and Venn, M. (1985) Biorheology 22, 159–69, which are herein incorporated by reference. Consequently, no methods are available to characterize the PG and collagen network phases in situ.

Being able to characterize the PGs and the collagen network together, however, is particularly important in understanding the etiology of OA. Although there has been indirect evidence presented that suggests that the collagen network loses mechanical integrity early in OA whereas PG content and composition may not change appreciably, it has not possible to demonstrate this definitively since heretofore no methodology for characterizing both the state of the PGs and of the collagen network phases in situ in the same tissue specimen has been developed. See, Maroudas, A. and Venn, M. (1977) Ann Rheum Dis 36, 399–406. Maroudas, A. (1976) Nature 260, 808–9. Maroudas, A., Evans, H., and Almeida, L. (1973) Ann. Rheum. Dis. 32, 1–9.

More generally, experimental and theoretical tools to determine collagen network integrity are also needed to understand the functional consequences of a) endogenous structural changes in cartilage (e.g., that occur normally in normal and abnormal development, aging, degeneration, and disease), b) exogenous changes (e.g., following the addition of biochemical agents such as proteinases, or resulting from genetic manipulations), and c) inherent differences between cartilage tissues (e.g., between species; as well as between different joints, different locations on the same joint, and young and old individuals of the same species). In addition, there is a need to understand how environmental (chemical, mechanical, or electrical) stresses affect connective tissue structure and function. These stresses may be endogenous (e.g., occurring during locomotion), or exogenous (e.g., applied externally to tissue cultures in vitro or during a clinical evaluation).

Further, it is becoming increasingly important to evaluate the growth and viability of the collagen network within tissue-engineered connective tissues, both in vitro (e.g., in drug efficacy studies), and in vivo prior to and following their implantation. Without a quantitative measure of collagen network integrity together with the swelling characteristics of the PGs, the relationship between collagen network structure and tissue function cannot be established.

There is, therefore, a need for a quantitative methodology for determining the mechanical integrity of the collagen network in cartilage and of other extracellular matrices.

SUMMARY OF THE INVENTION

It is, therefore, an object of the present invention to measure the mechanical properties of a collagen network in cartilage.

Another object of the present invention is to model the mechanical properties of cartridge according to separate phases for the collagen network and for the proteoglycan constituents.

A further object is to assess the condition of cartilage according to the mechanical properties of the collagen network in the cartilage.

Yet a further object of the present invention is to assess the mechano-chemical state of both the proteoglycan and collagen network phases in cartilage.

Still another object is to identify cartilage pathology according to the mechanical properties of the collagen network in the cartilage.

Yet another object of the present invention is to measure the mechanical properties of a collagen network in cartilage according to an in vitro mechano-osmotic technique.

Still a further object is to measure the hydrostatic pressure caused by tensile stresses developed within the collagen network as a function of tissue hydration.

Another object is to provide measures of mechanical integrity of the collagen and proteoglycan phases from data acquired in the osmotic titration measurements.

The present invention achieves these and other objects, and overcomes limitations of the background art and the prior art, by providing a method for measuring the mechanical integrity of a collagen network in cartilage and of other extracellular matrices according to applying a known mechanical stress to the sample; measuring a quantity representing hydration of the sample; and providing the extracellular network recoil pressure according to the known applied mechanical stress and the independently determined proteoglycan osmotic pressure corresponding to the hydration.

In accordance with an embodiment of the present invention, an in vitro mechano-osmotic titration method for determining the collagen network tension (i.e., recoil pressure) for a given collagen network hydration is used. Collagen samples are equilibrated in a saline solution and weighed. Some of these samples are compressed with various known applied osmotic pressures values by dialyzing them against different polyethylene glycol (PEG) concentrations, and then are again weighed. Other samples are first swelled by immersing them in a hypotonic saline solution, then compressed using a PEG concentration sufficient to restore their original volume in physiological saline. Collagen network hydration is based on the measured volumes of the water, PG, and non-collagenous protein phases compared with the measured volume of collagen network phase. The proteoglycan osmotic pressure corresponding to the measured hydrations is independently determined according to proteoglycan osmotic pressure versus proteoglycan fixed charge density measurements, intrafibrillar and extra-fibrillar water content determined from x-ray diffraction, and collagen content measurements. For each hydration, the collagen network recoil pressure is then calculated according to the independently determined proteoglycan osmotic pressure and to the known applied osmotic pressure. By determining the collagen network tension for a range of hydrations, the mechanical recoil pressure of the collagen network may be represented.

In accordance with a further embodiment of the present invention, the method may be used for diagnosing and/or monitoring the progression of diseases, such as osteoarthritis, preferably according to the collagen network stiffness, which for example, is shown to be reduced in osteoarthritic cartilage compared with normal cartilage. In accordance with a further embodiment of the present invention, the method may be used for assessing changes that occur normally in aging, which for example, is shown to increase collagen network stiffness. In accordance with yet a further embodiment of the present invention, the measured mechano-chemical properties of the collagen network in cartilage are incorporated into a mechanical model of cartilage in which the collagen network and proteoglycans are mathematically represented as separate phases in mechano-chemical equilibrium.

BRIEF DESCRIPTION OF THE DRAWINGS

Additional aspects, features, objects, and advantages of the invention will be understood and will become more readily apparent when the invention is considered in the light of the following description made in conjunction with the accompanying drawings, wherein:

FIG. 11 is a table of equilibrium parameters characterizing the composition and state of various cartilage tissue specimens;

FIG. 12 is a table showing changes in hydration, PG osmotic pressure, and collagen tension during osmotic loading;

FIG. 13 is a table showing relationships and material constants used to compute PG, collagen and specimen properties.

FIG. 18 is a table showing several possible measures or indices for the collagen network and polymer solution which may be generated in accordance with the methods and modeling, such as a supply and demand model analogous to economics, according to the present invention;

DETAILED DESCRIPTION OF THE PREFERRED EMBODIMENT

Figure 1:
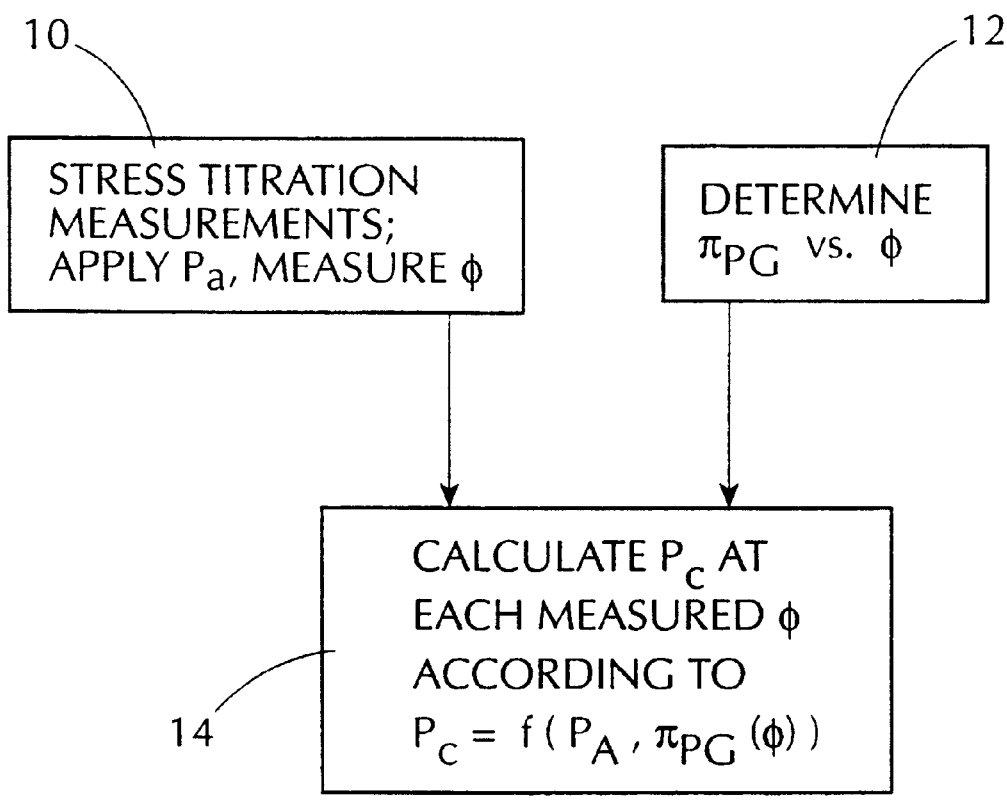
FIG. 1 is a flow diagram illustrating steps including an embodiment of the present invention.

Referring to FIG. 1, there is shown a flow diagram illustrating steps involved in measuring the mechanical properties of the collagen network in cartilage in accordance with an embodiment of the present invention. In step 10, a mechanical titration measurement is performed such that a cartilage sample is subject to various applied mechanical loading pressures, and for each applied pressure measurements are made from which the collagen network hydration may be determined. For instance, the mass of the cartilage sample at each applied pressure may be measured, and compared with the mass of the cartilage sample when desiccated. In step 12, the osmotic pressure of proteoglycans for each hydration is determined based on the proteoglycan concentration in the cartilage samples, and on separate measurements of proteoglycan osmotic pressure in solution. As discussed further below, the determination of proteoglycan concentration preferably accounts for the partitioning of the water between intra-fibrillar (i.e., within the collagen fibrils) and extra-fibrillar compartments and its dependence on the osmotic pressure applied to the collagen fibrils. Then, in step 14, based on the equilibrium relationship among the applied pressure, collagen network stress, and proteoglycan osmotic pressure for the experimental apparatus, the collagen network stress is calculated for each hydration corresponding to each applied pressure.

Figure 2:
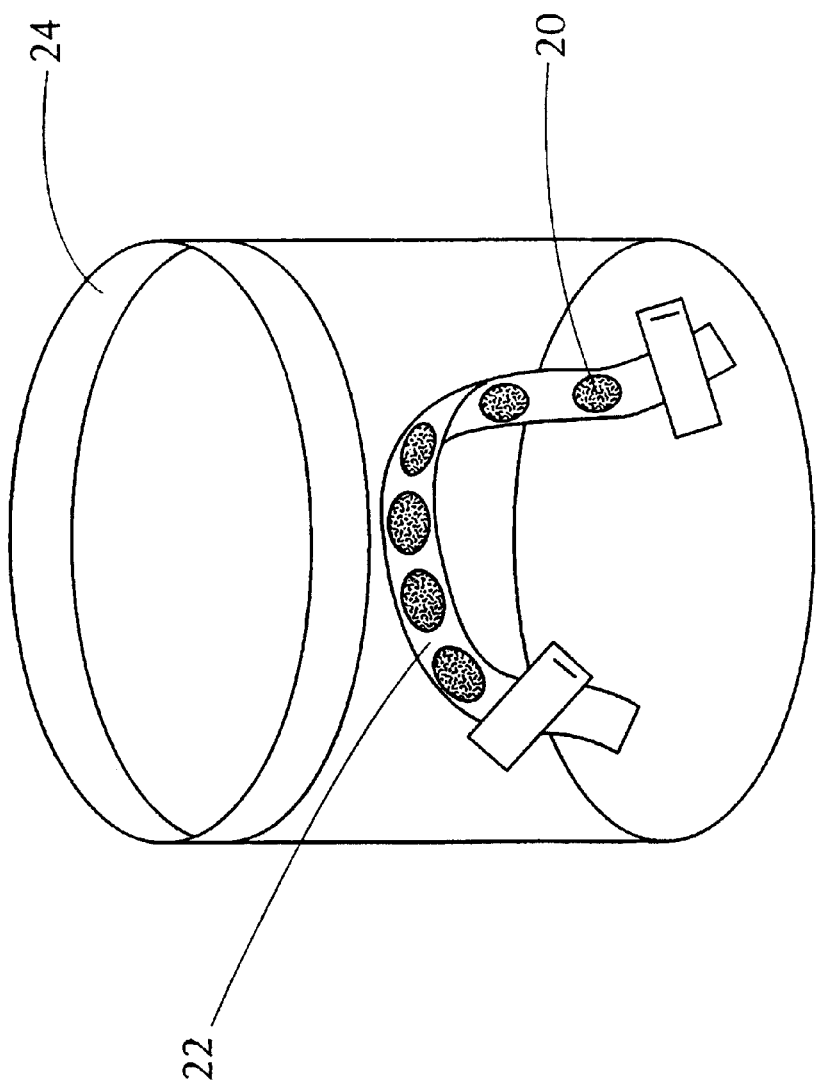
FIG. 2 schematically depicts a cartilage specimen confined in a semi permeable dialysis membrane that excludes the polyethylene glycol (PEG) molecules in the external bath, in accordance with an embodiment of the present invention, and as adapted from Grushko, G. (1987) Age-related variations in some physical and chemical properties of articular cartilage, Master's Thesis, Technion, Haifa.

In accordance with an embodiment of the present invention, a mechano-osmotic pressure titration apparatus and methodology is employed to apply an isotropic stress to collagen samples. Referring to FIG. 2, there is schematically depicted a dialysis sack 24 for use in applying the mechanoosmotic pressure titration methodology. A cartilage sample 20 is inserted into a dialysis bag 22 which is surrounded by a solution (e.g., saline solution) containing moieties (e.g., polyethylene glycol (PEG) molecules) which do not permeate the dialysis bag and give rise to a known osmotic pressure ($\pi_{PEG}$). The osmotic pressure may be controlled according to the concentration of osmotically active PEG in the external bath. It may also be appreciated that the stress to which the collagen network is subjected in situ may be augmented or diminished by changing the ionic strength of the interstitial fluid (thus changing the osmotic pressure exerted by the PG) or by changing the concentration of the osmotically active PEG in the external bath (thus altering the osmotic stress acting on the tissue sample across a dialysis membrane). Preferably, prior to dialysis, the collagen sample is equilibrated with a saline solution having the same concentration as the saline solution of the bath during dialysis, and is weighed before and after dialysis. In some experiments, it is contemplated that PEG could also be added to the solution within the dialysis bag, in which case it could penetrate the cartilage sample, and exert an osmotic pressure on the collagen fibrils, which it cannot penetrate. In addition, after weighing subsequent to dialysis, the collagen sample is preferably re-equilibrated with the saline solution and then weighed to ensure that the original, pre-dialysis weight is restored.

It is understood that with no external stress applied on the cartilage matrix, there is a balance between the osmotic pressure exerted by the proteoglycans (PGs), $\pi_{PG}^{eq}$ (which acts to imbibe fluid), and the collagen network restraining pressure Pc (which acts to express fluid). See, Maroudas, A. (1976) Nature 260, 808–9. When there is an applied isotropic compressive stress, mechano-chemical equilibrium is achieved when the sum of $Pc^{eq}$ and the applied isotropic compressive stress (both of which act to express interstitial fluid) equals $\pi_{PG}$ (that tend to express interstitial fluid). In the mechano-osmotic titration apparatus schematically represented in FIG. 2, the applied isotropic compressive stress corresponds to the osmotic stress, $\pi_{PEG}^{eq}$, on the cartilage specimen across the dialysis bag, due to the polyethylene glycol (PEG) in the external bath. Accordingly:

$$Pc^{eq} + \pi_{PEG}^{eq} = \pi_{PG}^{eq} \quad (1)$$

In accordance with this embodiment of the present invention, for each applied osmotic stress, the equilibrium hydrostatic pressure developed by the collagen network while restrain ng the entrapped proteoglycans, $Pc^{eq}$, is inferred from measurements of the PG osmotic pressure $\pi_{PG}^{eq}$, and the applied osmotic stress as generally described previously by Basser, P. J., Schneiderman, R., Bank, R., and Maroudas, A., (1996) in Transactions of the 42nd Annual Meeting, Orthopaedic Research Society, Atlanta, 736, which is herein incorporated by reference.

It is understood that alternative techniques may be used for applying an external pressure to the cartilage sample, and that the balance of forces equation may be modified to reflect the physical configuration. An example of an alternative implementation is to use a confined compression apparatus, which limits cartilage deformation to be uni-axial, along which a mechanical probe (e.g., piston) applies pressure to the collagen, and which permits fluid uptake and discharge by the collagen (e.g., by using porous materials to confine the collagen sample) as equilibrium conditions are reached. Another example of an alternative implementation is an unconfined compression apparatus, in which the cartilage is loaded in a single direction, but is allowed to deform in the radial direction.

In accordance with the present embodiment, a method for determining the PG osmotic pressure for a given hydration is based on determining the PG concentration in the extrafibrillar region of the collagen samples, and on independently determined osmotic pressure measurements for PGs in solution. More particularly, accurate means have been devised to measure the osmotic pressure of the PGs trapped within the fibrous collagen network. These means are based on the assumption that $\pi_{PG}^{eq}$ in situ equals $\pi_{PG}^{eq}$ in a PG solution (with the same PG composition) whose concentration equals that in the extrafibrillar space of cartilage. The PG concentration in the extrafibrillar space is determined by measuring the fixed charge density (FCD) of the PGs in the collagen, and by determining for each total hydration the extrafibrillar water content. In accordance with an embodiment of the present invention, FCD may be obtained by means of the Tracer Cation Method using $Na^{+22}$ in hypotonic saline (0.015M NaCl) as described in Maroudas, A. and Thomas, H. (1970) Biochimica et Biophysica Acta 215, 214–216, which is herein incorporated by reference, whereas the extrafibrillar water content is determined based on the total hydration and on x-ray measurements of intiafibrillar water content at different osmotic pressures applied to the collagen network.

That is, since not only must mechano-chemical equilibrium eventually be achieved between the cartilage tissue matrix and the surrounding bath, it must also be achieved between the PG and collagen network phases that constitute the cartilage tissue matrix, there is a intrafibrillar and extrafibrillar water partitioning which is dependent on the osmotic pressure exerted on the collagen fibrils. In particular, the collagen network is itself osmotically active so its fibrils and the PGs that they exclude compete for interstitial water. In equilibrium, the chemical potential of water must be the same in these intra and extrafibrillar compartments. The osmotic behavior of the intrafibrillar compartment can be characterized by a relationship that has been previously measured between the applied stress acting on it and the collagen network hydration. See, Maroudas, A., Wachtel, E., Grushko, G., Katz, E. P., and Weinberg, P. (1991) Biochim Biophys Acta 1073, 285–94, which is herein incorporated by reference.

In particular, an equation relating $\pi_{PG}^{eq}$ and $FCD_{eff}^{eq}$, where $FCD_{eff}^{eq}$ is the fixed-charge density (in milli Eqs per gm of extrafibrillar water) in the cartilage sample and $\pi_{PG}^{eq}$ is the PG osmotic pressure, may be obtained from osmotic pressure measurements of PGs extracted from human articular cartilage. A quadratic function that fits the data adequately may be obtained by non-linear regression and, in accordance with experiments described hereinbelow, may for example be accurately represented by a second order polynomial:

$$\pi_{PG}^{eq} = A_0 + A_1 FCD^{eq} + A_2 (FCD^{eq})^2 \quad (2a)$$

where $A_0$, $A_1$, and $A_2$ are viral coefficients. As described, the PG osmotic pressure in situ is preferably based on PG concentration in the extrafibrillar space (i.e., based on the effective FCD), not in the tissue as a whole, so for clarity, Eq. (2a) may be rewritten as:

$$\pi_{PG}^{eq} = A_0 + A_1 \, FCD_{eff}^{eq} + A_2 \, (FCD_{eff}^{eq})^2 \quad (2b)$$

Figure 3:
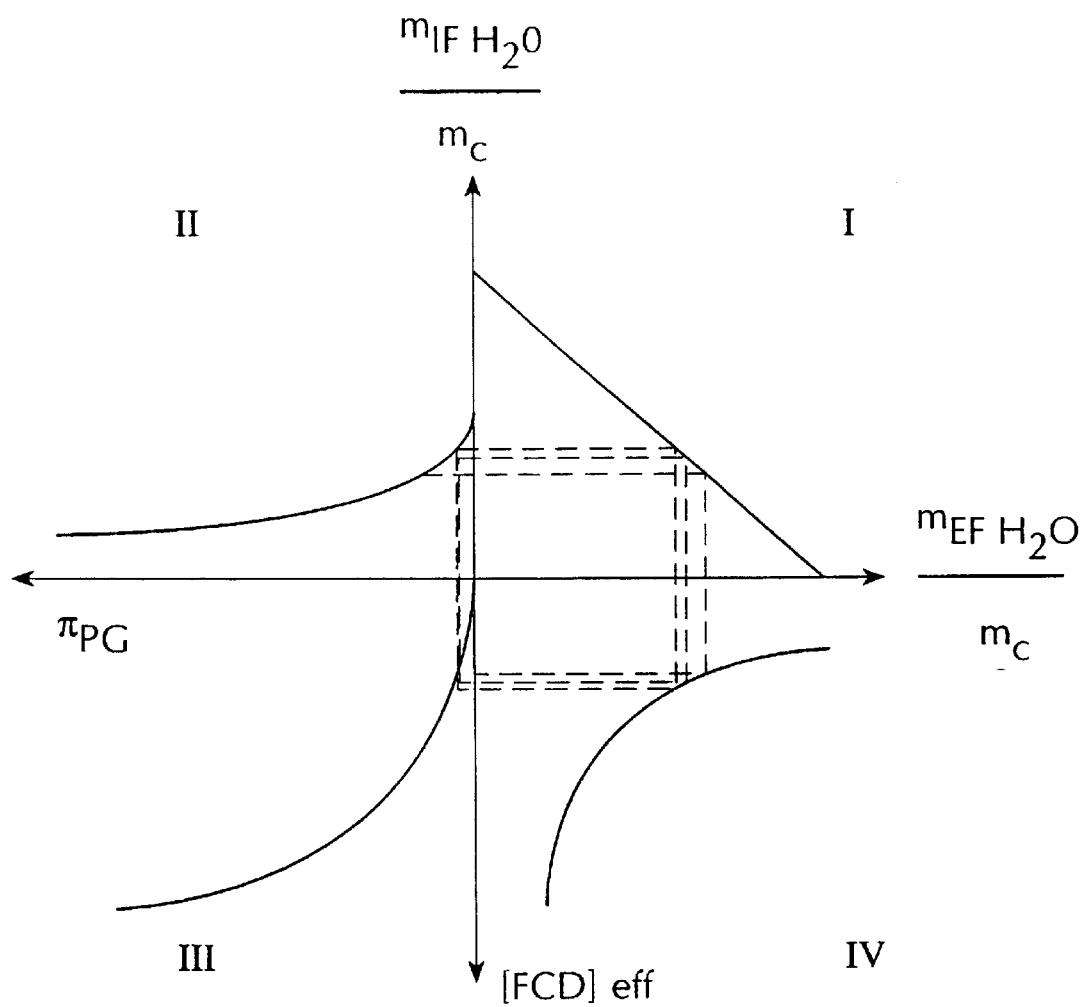
FIG. 3 shows a four quadrant model, in accordance with the present invention, and its graphical solution.

The curve is illustratively displayed as a parabolic function in Quadrant III of FIG. 3. It may be appreciated that this relation does not have to be specifically of this form. For example, a polynomial of higher order can be used. Moreover, this is a phenomenological equation to which parameters are fit using measured data. An equivalent relationship between the molar concentrations of the individual charged groups on the PGs (such as carboxylic acid ([COO$^-$]) and sulfonic acid ([SO$_3^-$])) as well as charged groups on the non-collagenous proteins (such as carboxylic acid ([COO$^-$]) and amine groups ([NH$_3^+$])) could be used in place FCD in Eq. 2b. In general, what is required is a relationship between the swelling pressure and the molecular constitutuents of cartilage excluding the collagen network. Moreover, it is understood that there are alternative methods for determining the molecular constituents in the cartilage. For instance, the distribution and charge of these species could be determined non-invasively or semi-invasively using a combination of spectroscopic techniques, such as magnetization transfer MRI (to measure collagen), Na+ MRI as described by Gray et al. (to measure FCD) (Burstein, D., Gray, M. L., Hartman, A. L., Gipe, R. and Foy, B. D. (1993) J Orthop Res 11, 465–78), electromechanical spectroscopy, as described by Grodzinsky et al. (to measure FCD) (U.S. Pat. No. 5,246,013), proton density MRI (to measure total water content).

It may be appreciated that since the $FCD_{eff}$eq is defined with respect to extrafibrillar water mass and that no net charge is lost or gained during tissue compression or swelling, $FCD_{eff}$eq is related to $[FCD]_{Tissue}$—the fixed charge density in mEq per gm of total water in the unloaded cartilage—according to:

$$FCD_{eff}eq \, m_{EFH2O}^{eq} = FCD_{TotalH2O} * (m_{IFH2O} + m_{EFH2O}) = FCD_{Tissue} M_{wet0} \quad (3)$$

where $FCD_{Tissue}$ is the fixed charge density in mEq per gram of unloaded tissue in isotonic saline, $FCD_{TotalH2O}$ is the fixed charge density given in milliEq per gram total tissue water, and $M_{wet0}$ is the weight of the tissue in isotonic saline. Equation (3), which simply reflects charge conservation, is plotted as a hyperbolic function $FCD_{eff}$eq vs $m_{EFH2O}^{eq}$ in Quadrant IV of FIG. 3.

In accordance with an embodiment of the present invention, the equation relating the intrafibrillar water fraction (defined as the mass of intrafibrillar water, $m_{IFH2O}^{eq}$, divided by the mass of dry collagen, $m_c$) and the net applied pressure acting on the collagen fibrils, which in ative cartilage specimens is $\pi_{PG}^{eq}$ may be represented by the following exponentially decaying function:

$$\frac{m_{IFH2O}^{eq}}{m_c} = r + s \cdot e^{-\Pi_{PG}^{eq}} \quad (4)$$

which has been shown to fit x-ray measurements of intrafibrillar water content for various osmotic pressures on the collagen fibrils. See, Maroudas, A., Wachtel, E., Grushko, G., Katz, E. P., and Weinberg, P. (1991) *Biochim Biophys Acta* 1073, 285–94, which is herein incorported by reference. The shape of the exponential function is shown in Quadrant II of FIG. 3.

In addition to the foregoing relationships, it is convenient to express the conservation of mass of the tissue's macromolecular constituents. Since no PGs or collagen are lost or added during tissue compression or swelling, tissue mass can only change by expressing or imbibing water. Therefore the total mass of water must be given by the difference of the wet and dry mass of the tissue:

$$m_{EFH2O}^{eq} + m_{IFH2O}^{eq} = M_{wet} - M_{dry} \quad (5a)$$

where $M_{wet}$ is the total mass of the wet tissue, $M_{dry}$ is the total mass of the dry tissue. The former is measured by weighing the specimens at equilibrium; the latter by desiccating the specimens and then weighing them. It is useful to recast Eq (5a) in the following equivalent form:

$$\frac{m_{IFH2O}^{eq}}{m_c} = -\frac{m_{EFH2O}^{eq}}{m_c} + \left[\frac{M_{wet} - M_{dry}}{m_c}\right] \quad (5b)$$

Eq. (5b) is displayed as a linear function in Quadrant I of FIG. 3. Eq. (5b) suggests one measure of cartilage tissue hydration as $(M_{wet} - M_{dry})/fc$. This quantity measures the mass of water within the tissue per unit mass of collagen. Another measure of tissue hydration is its dilatation, defined as the fractional change in the equilibrium volume of the tissue, $(V^{eq} - V^{eq})/V^{eq}$.

An appropriate measure of collagen network swelling should be a dimensionless number that only depends on the collagen network characteristics and its state of deformation. In particular, we do not wish to use $M_{wet}$ or $V^{eq}$ in determining the reference configuration of the collagen network since they are affected by the pH and ionic strength of the solvent, the GAG composition and content, and the mechanical properties and mass of the collagen network. One quantity that has been widely used in the polymer gel literature is the hydration parameter, $\theta$, which is the ratio of the polymer volume to the interstitial solvent volume, $V_p/V_w$. See, Flory, P. J. (1953) Principles of Polymer Chemistry, Cornell University Press, Ithaca, N.Y. Unlike a simple polymer gel, which consists of a polymeric network and an interstitial solvent, cartilage is a complex composite medium, consisting of a collagen network that contains intrafibrillar water, and an extrafibrlllar compartment that contains interstitial solvent and proteoglycans (PG). Therefore, we must modify this definition of hydration in a meaningful way to account for the presence of GAGs and non-specific proteins present in the extrafibrillar space.

One measure of collagen network hydration, $\phi = 1/\theta$, is the ratio of the total tissue volume outside the dry collagen (i.e., the volume of the fluid encompassed by the network) divided by the volume of dry collagen:

$$\phi_1 = \frac{m_{TOTALH2O} v_{H2O} + m_{GAG} v_{GAG} + m_{NCP} v_{NCP}}{m_c v_c} \quad (6a)$$

Another definition of collagen network hydration is the ratio of the wet-volume of the tissue to the wet volume of the collagen fibrils:

$$\phi_2 = \frac{m_{TOTALH2O} v_{H2O} + m_{GAG} v_{GAG} + m_{NCP} v_{NCP} + m_c v_c}{m_c v_c + m_{IFH2O} v_{H2O}} \quad (6b)$$

A third definition is the total tissue water volume divided by the volume of the wet collagen fibrils.

$$\phi_3 = \frac{m_{TOTALH2O} v_{H2O}}{m_c v_c + m_{IFH2O} v_{H2O}} \quad (6c)$$

In these definitions, $v_{H2O}$, $v_{NCP}$, $v_{GAG}$, $v_c$ are the specific volumes of water, non-collageneous protein, glycosaminoglycans, and collagen, respectively, and $m_{H2O}$, $m_{NCP}$, $m_{GAG}$, $m_c$ are the specific volumes of water, non-collageneous protein, glycosaminoglycans, and collagen, respectively,. Each definition has strength and weaknesses. Which one is used is determined also by considerations such as ease of measurement, robustness, and the physical insight it provides.

Accordingly, it is understood that four quantities may be used to characterize the equilibrium state of a cartilage sample to which an arbitrary isotropic pressure is applied: $m_{EFH2O}^{eq}$, $m_{IFH2O}^{eq}$, $FCD_{eff}^{eq}$, and $\pi_{PG}^{eq}$, where $m_{EFH2O}^{eq}$ and $m_{IFH2O}^{eq}$ are the respective masses of the extra- and intra-fibrillar water; $FCD_{eff}$eq is the fixed-charge density (in milli Eqs per gm of extrafibrillar water), and $\pi_{PG}^{eq}$ is the PG osmotic pressure. See, Maroudas, A. and Grushko, G. (1990) in Methods in Cartilage Research: Measurement of Swelling Pressure of Cartilage (Maroudas, A. and Kuettner, K. E., Eds.), pp. 298–301, Academic Press, San Diego, which is herein incorporated by reference.

The four governing equations (i.e., equations 2b, 3, 4b, 5) above are transcendental; no closed-form solution can been found for the equilibrium values of the four dependent variables. However, in accordance with the present invention, $\pi_{PG}^{eq}$, $FCD_{eff}$eq, $m_{EFH2O}^{eq}$, and $m_{IFH2O}^{eq}$ can be determined (and were determined, as described hereinbelow) by solving these equations numerically once the experimental quantities $m_c$, $M_{wet}$, $M_{dry}$, and $FCD_{Tissue}$ are determined, and the fitting parameters r,s, and t, and $A_0$, $A_1$, and $A_2$ are provided. After $\pi_{PEG}$ is specified, and $\pi_{PG}^{eq}$ is calculated numerically, $Pc^{eq}$ can then be calculated using Equation (1) at the current equilibrium network hydration, $\phi^{eq}$, defined in Eq. 6a. Then, by varying $\pi_{PEG}$ systematically, a data set of $Pc^{eq}$ vs $\phi^{eq}$ may be obtained.

It is also instructive to solve the four simultaneous equilibrium equations graphically. Referring again to FIG. 3, wherein the first quadrant (I) contains the equation of conservation of mass, the fourth quadrant (IV) contains the equation of conservation of charge, the third quadrant (III) contains the empirical relationship between the effective fixed charge density, $FCD_{eff}$, and the total equilibrium osmotic pressure, $\pi_{PG}$, exerted by the PGs, and the second quadrant (II) contains the empirical equilibrium relationship between the applied stress acting on collagen network (which in this experiment is $\pi_{PG}$) and the collagen fibril hydration, a stable solution results when a closed rectangular orbit evolves as shown. More particularly, as illustrated in FIG. 3, such a solution can be found by guessing an initial value of one of the dependent variables (i.e., choosing a starting point lying on any of the four curves), and then moving either in a clockwise or counterclockwise direction from that point, alternately constructing vertical and horizontal line segments that intersect curves in adjacent quadrants (as shown in FIG. 3). A solution exists when the trajectory iterates to a closed, stable, rectangular orbit whose edges intersect the four coordinate axes at their respective equilibrium values.

Figure 4:
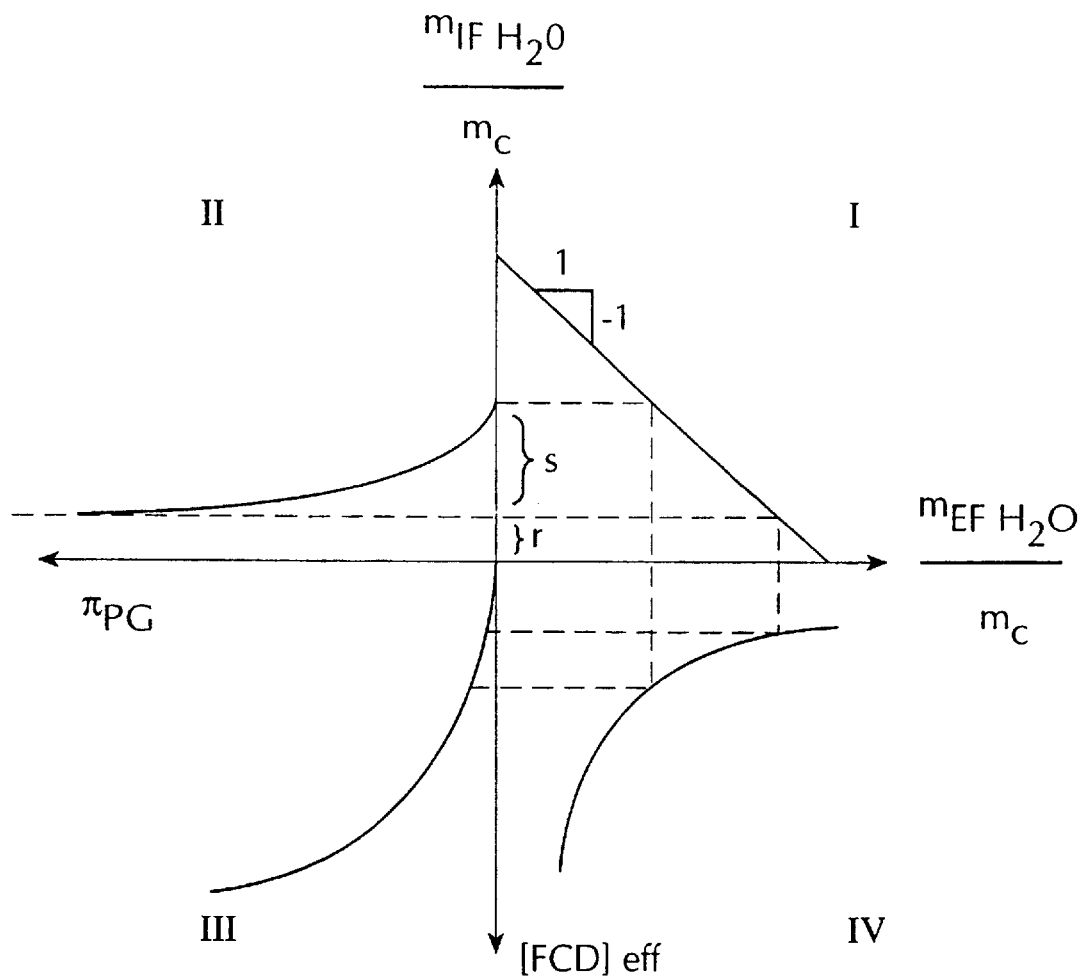
FIG. 4 illustrates, by way of the four quadrant model of FIG. 3, limits on possible equilibrium values of the dependent variables.

It can be clearly seen that there are values of the dependent variables for which no equilibrium solution exists. Referring to FIG. 4, it is seen that because the equilibrium collagen hydration is required to lie between r and r+s, for a stable equilibrium solution to exist, the values of the three other depedent variables are also constrained. More particularly, it is seen that in Quadrant II, $r<m_{IFH2O}^{eq}/mc<r+s$, where r and s are defined in Equation (4). These limits on $m_{IFH2O}^{eq}$ also limit the range of the other dependent variables. In Quadrant I, the range of admissible values of $m_{EFH2O}^{eq}/mc$ lies within: $(M_{wet}-M_{dry})/m_c-(r+s)<m_{EFH2O}^{eq}/m_c<(M_{wet}-M_{dry})/m_c-r$. This, in turn, limits the range of admissible values assumed by $FCD_{eff}^{eq}$: $FCD_{eff}^{eq}{}_{min}=(FCD_{Tissue}M_{wet0})((M_{wet}-M_{dry})-m_cr)$ $<FCD_{eff}^{eq}<(FCD_{Tissue}M_{wet0})/((M_{wet}-M_{dry})-m_c(r+s))=FCD_{eff}^{eq}$. Finally, these restrictions on $FCD_{eff}^{eq}$ limits the range of admissible values of the PG osmotic pressure, $\pi_{PG}^{eq}$ from Eq. 2(b): $A_0+A_1 \ FCD_{eff}^{eq}{}_{min}+A_2 \ FCD_{eff}^{eq}{}_{min}^2<\pi_{PG}^{eq}<A_0+A_1 \ FCD_{eff}^{eq}{}_{max}+A_2 \ FCD_{eff}^{eq}{}_{max}^2$. This information is also important in arriving at a robust numerical solution to the four simulataneous equations displayed in FIGS. 3 and 4, since not all initial guesses will lead to a stable equilibrium solution.

While this graphical approach does not provide accurate quantitative solutions for $m_{EFH2O}^{eq}$, $m_{IFPH2O}^{eq}$, $\pi_{PG}^{eq}$, and $FCD_{eff}^{eq}$, it is also useful in exploring the qualitative behavior of the cartilage specimen in experiments, particularly how changes in one or more independent variables or parameters affect all of the dependent variables. For example, decreasing ionic strength of the external bath causes the slope of $\pi_{PG}^{eq}$ vs $FCD_{eff}^{eq}$ to increase for each value of $FCD_{eff}^{eq}$. This results in the following changes at equilibrium: $m_{EFH2O}^{eq}$ increases, $m_{IFH2O}^{eq}$ increases, $\pi_{PG}^{eq}$ increases, and $FCD_{eff}^{eq}$ increases. In contrast, adding trypsin to reduce total fixed charge, (i.e., $FCD_{Tissue}$ decreases) shifts $FCD_{eff}^{eq}$ vs. $m_{EFH2O}^{eq}/m_c$ closer to the origin, without affecting the other three curves, resulting in: $m_{EFH2O}^{eq}$ decreasing, $m_{IFH2O}^{eq}$ decreasing, $\pi_{PG}^{eq}$ decreasing, and $FCD_{eff}^{eq}$ decreasing.

It may be appreciated that since the relationship between Pc and collagen network hydration ($\phi$) may be measured according to the present invention, that a further aspect of the present invention is that equilibrium cartilage free swelling and isotropic loading may be modeled accordingly. Such a model, which explicitly accounts for the collagen network mechanical properties, facilitates understanding cartilage behavior from a chemiphysical standpoint, as well as a answering biologically relevant questions about cartilage behavior such as: What values will $\pi_{PG}^{eq}$, $Pc^{eq}$, $FCD_{eff}^{eq}$, $m_{EFH2O}^{eq}$, and $m_{IFH2O}^{eq}$ assume in equilibrium for an isotropic cartilage specimen that is unloaded or isotropically loaded? What values of tissue and network hydration does it assume then? Why $\pi_{PG}^{eq}$ are and $Pc^{eq}$ approximately 4 atm in normal unloaded cartilage specimens? If we were to apply an infinitesimal isotropic load, perturbing the specimen from its unloaded equilibrium state, what would be the new values of $m_{EFH2O}^{eq}$, $m_{IFH2O}^{eq}$, $\pi_{PG}^{eq}$, $FCD_{eff}^{eq}$, and $Pc^{eq}$ in the specimen? In that case, what volume of interstitial water expressed by the tissue would come from the intrafibrillar and extrafibrillar compartments?

Providing such a model to answer these questions requires additional information about the cartilage specimen that is not embodied in Eqs. 2–5 alone. In general, to characterize the behavior of the tissue in free swelling or isotropic loading requires augmenting and ammending the model described above so that $M_{wet}-M_{dry}$ no longer constrains the values of $m_{EFH2O}^{eq}$, and $m_{IFH2O}^{eq}$, as it does in Equation (5b), and $_{Pc}^{eq}$ is now treated as a new dependent variable whose value must be determined along with the other four: $m_{EFH2O}^{eq}$, $m_{IFH2O}^{eq}$, $\pi_{PG}^{eq}$, and $FCDC_{eff}^{eq}$. In this case, Equation (1) must now be used explicitly since $\pi_{PG}^{eq}$ is not measured directly (as in the experiment above) or specified a priori. However, since it is known how to determine $P_c^{eq}$ vs $\phi^{eq}$ using the osmotic stress titration experiment, this relationship can be presumed to be known. Since Eq. (6) relates $\phi^{eq}$ to $m_{EFH2O}^{eq}$ and $m_{IFH2O}^{eq}$, the new relationship is of the form:

$$Pc^{eq}=f(\phi^{eq})=f(m_{EFH2O}^{eq}, m_{IFH2O}^{eq}) \quad (6.5)$$

It would appear that there are now six equations and five unknowns; however, this is not the case since $M_{wet}-M_{dry}$ is no longer measured or specified as it is in measuring Equation (6.5), so that the conservation of mass equation, i.e., Equation (5a) or Equation (5b), provides no additional information.

These five non-linear equations can also be solved numerically for the equilibrium values of their five unknowns using similar root finding methods described above. For instance, the Newton Raphson technique (e.g., as provided in Mathematica) may be used to solve these equations because of its stability and ease of implementation. However, with five equations and five unknowns, it is no longer possible to solve this system of equations graphically using the four coordinate axes displayed in FIGS. 3 and 4.

As stated, to characterize the behavior of the tissue in free swelling or isotropic loading requires augmenting and amending the model given in Maroudas, A. and Grushko, G. (1990) in Methods in Cartilage Research: Measurement of Swelling Pressure of Cartilage (Maroudas, A. and Kuettner, K. E., Eds.), pp. 298–301, Academic Press, San Diego. First, we no longer constrain $M_{wet}-M_{dry}$ or $m_{EFH2O}^{eq}+m_{IFH2O}^{eq}$, as in Equation (5). Second, $P_c^{eq}$ must be treated as a new dependent variable whose value is determined along the $m_{EFH2O}^{eq}$, $m_{IFH2O}^{eq}$, $\pi_{PG}^{eq}$ and $FCD_{eff}^{eq}$. However, we can presume to have determined $Pc^{eq}$ vs $\phi^{eq}$ (using the osmotic stress titration experiment described above), and since Eq. (6) relates $\phi^{eq}$ to $m_{EFH2O}^{eq}$ and $M_{IFH2O}^{eq}$, we can include in our model a new relationship of the form of equation 6.5. Third, Eq. (1) must be satisfied explicity since $\pi_{PG}^{eq}$ and $P_c^{eq}$ are now two dependent variables whose Eq. (1) constrains.

It may also be understood with reference to the Table in FIG. 18 that there are many possible measures or indices for characterizing the cartilage and/or collagen network mechanical properties which may be generated in accordance with the methods and modeling according to the present invention, and further that these indices may be used as a basis for diagnosing tissue pathology.

It is appropriate to view the cartilage tissue matrix as a network of mechanically coupled, macromolecular-scale, sealed elastic collagenous dialysis sacks that contain PGs. Picturing cartilage as "GAGs in Bags" allows us to explain mechano-chemical phenomena exhibited by cartilage, and to construct more realistic constitutive laws of the cartilage tissue matrix.

We would expect the network of dialysis sacks to possess an non-zero unstressed volume, and become increasingly stiff as its volume increases. Moreover, we would expect that as volume increases, $\pi_{PG}^{eq}$ would decrease, as the PGs become more dilute. Additionally, one can see how normal surface traction arising from the tensile stresses that develop within the membrane would balance the osmotic pressure exerted by the PGs.

It is also possible to use this picture of cartilage to understand how we infer $Pc^{eq}$. By using PEG solutions of different concentrations to apply different levels of osmotic stress, and by calculating the osmotic pressure of the PGs at each corresponding level of compression, we calculate the restraining pressure exerted by the sacks by requiring that in mechanical and chemical equilibrium, the restraining pressure must equal the difference of the calculated PG osmotic pressure and the applied osmotic stress.

This model even helps us understand experiments we performed (described hereinbelow in connection with the Example) to achieve equilibrium tissue hydrations larger or smaller than those developed when the specimens were unloaded in physiological saline. When equilibrated in a solution with a lower ionic strength, PG osmotic pressure in the sacks increases, and so does the restraining stress required to oppose it at equilibrium. At the new equilibrium, the sacks expands to a larger volume, while their membranes exert a larger restraining pressure to balance the higher osmotic pressure exerted at each volume. Conversely, we the PGs are partially digested by adding trypsin, the reduced PG osmotic pressure in each sack will exert a lower osmotic stress, and each sack then assumes a smaller equilibrium volume and exerts a smaller restraining pressure.

In addition, this model even helps us picture what appears to occur in early stages of OA. As the dialysis membrane looses elasticity, it expands to a larger volume but exerts a smaller restraining pressure required to equalize the osmotic pressure of the trapped PGs.

This picture of cartilage subsumes a useful but more naive model of cartilage that describes it as an air-filled latex balloon, where the gas filling the balloon is like the PG phase, and the balloon's membrane is like the collagen network. This analogy breaks down in several important respects. First, $\pi_{PG}^{eq}$ in cartilage is affected by the hydration state of the collagen fibrils since the PGs and collagen fibrils both compete for interstitial water. However, in an ideal balloon, the form of Boyle's law is not affected by the balloon's membrane. Second, when one pops a balloon, its air escapes. When cartilage is scored, PGs do not all leach out and "deflate" the tissue. Clearly, as in the Ogston picture, the "balloons" in cartilage must exist on a macromolecular, not a macroscopic length scale. Third, the PG and collagen content in cartilage is known to vary with position (i.e., it is heterogeneous). There is also evidence that the collagen network properties are anisotropic in some regions, and that the principal fiber directions change with position within the tissue. The single balloon model of cartilage cannot adequately describe spatial or orientational variations, whereas the "GAGs in Bags" model allows us to incorporate anisotropy of the collagen network, as well as heterogeneity in PG and collagen distribution and composition.

Another useful analogy that we can exploit to facilitate the qualitative analysis of cartilage behavior in equilibrium is to view PG swelling and collagen network restraint as mutually competitive processes that result in an equilibrium "compromise" between the two phases. In doing so, we see a striking similarity between the equilibrium Pc–V and $\pi_{PG}$–V and curves, and the equilibrium "supply" and "demand" curves, respectively. See, e.g., Marshall, A. (1890) Principles in Economics, Cambridge University Press,. Specifically, the $\pi_{PG}$–V curve is analogous to the demand function relating market price (in $/unit) and units desired, while the collagen network Pc–V curve is analogous to the supply function relating market price (in $/unit) and units supplied. Just as in mechanical equilibrium, osmotic swelling pressure equals network restraining pressure, in market equilibrium, supply equals demand.

Figure 5A:
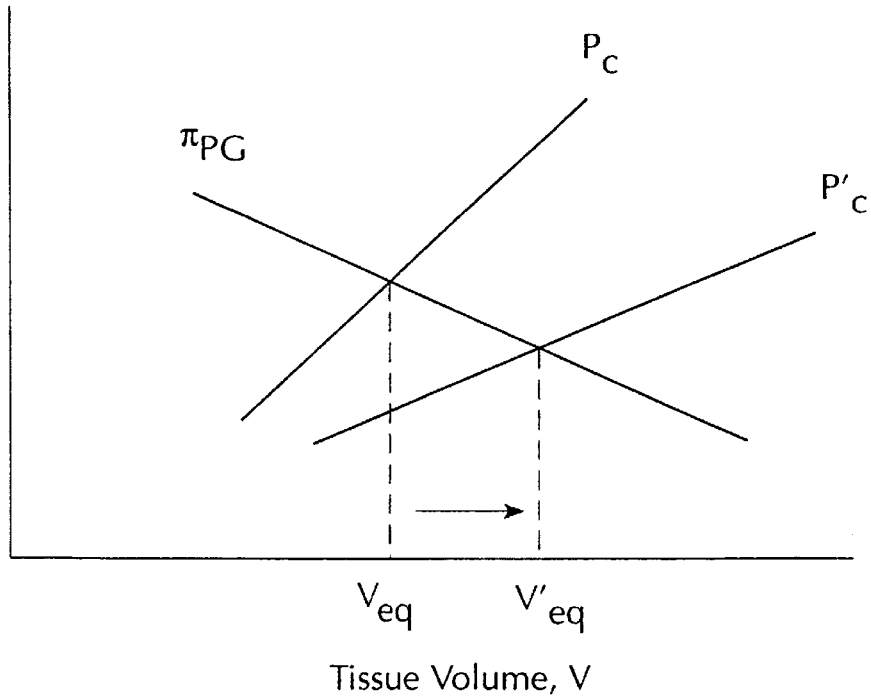
FIG. 5a and FIG. 5b illustrate the use of a "supply and demand" framework to analyze the qualitative equilibrium behavior of cartilage.
Figure 5B:
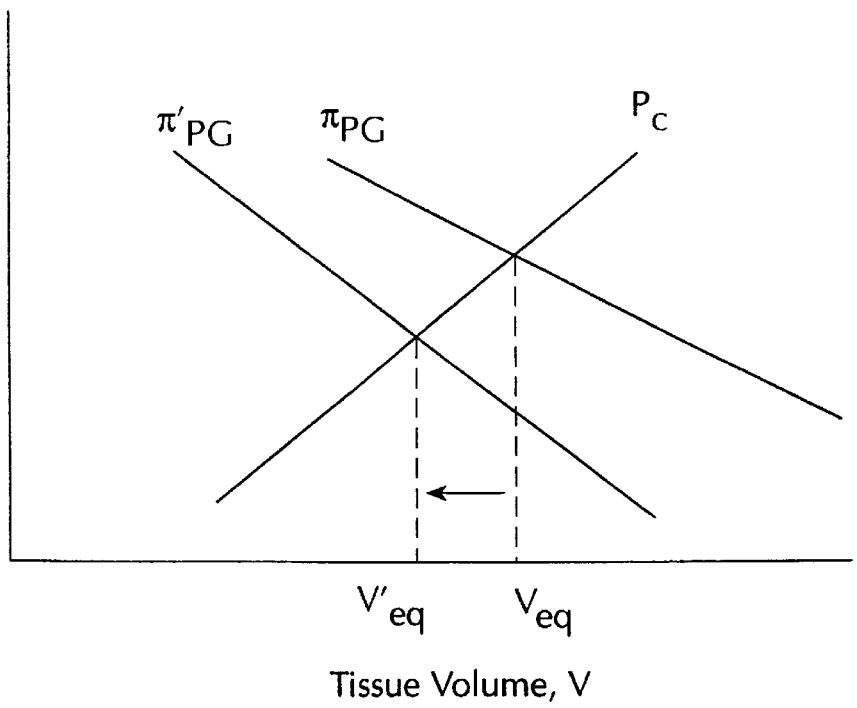

FIGS. 5a and 5b illustrate the use of the "supply and demand" framework to analyze the qualitative equilibrium behavior of cartilage. Linear relations between variables are used for simplicity, but formally can be thought of as linearized curves about the equilibrium point. FIG. 5a illustrates the effect of shifting the slope and/or intercept of the Pc vs V curve while leaving the $\pi_{PG}$ vs V curve unchanged. Shifting the Pc vs V curve to the right is what would occur if the hydration or volume at zero network tension were increased, but network stiffness were left unchanged. Changing the slope effectively changes the stiffness of the collagen network. Increasing the unstressed hydration or decreasing the slope will have the effect of increasing the equilibrium tissue volume or hydration, while decreasing the unstressed hydration or increasing stiffness has the effect of decreasing equilibrium tissue hydration. Similar effects are seen in the $\pi_{PG}$ vs V curve shown in FIG. 5b. Here, increasing the steepness of the curve or shifting it to the left decreases equilibrium volume; making the curve more shallow or shifting it to the right increases equilibrium hydration.

As an example, consider equilibrating the cartilage specimen in hypotonic solution (e.g. 0.015M NaCl) after having previously equilibrated it in isotonic saline. The collagen network has effectively no net charge in physiological saline, and its physical-chemical properties are largely insensitive to perturbations in ionic strength in this state. However, small perturbations in ionic strength do have a profound effect on the PGs' osmotic pressure resulting primarily from mutual electrostatic repulsion. This would effectively leave Pc and V curves unchanged, but would significantly increase the slope of $\pi_{PG}$ vs. V. Thus, the equilibrium PG osmotic pressure and collagen network tensile stress would increase (i.e., $\pi_{PG}^{eq}=Pc^{eq}$ increases), and the equilibrium volume would increase as well (i.e., $V^{eq}$ increases).

As another example, the supply and demand model may be used to predict the qualitative behavior of the tissue in response to trypsin treatment of normal cartilage specimen. Trypsin addition digests the PGs, without affecting collagen network properties. This would lower $\pi_{PG}$ vs. V and/or reduce its slope. Thus, the equilibrium PG osmotic pressure and collagen network tensile stress would decrease (i.e., $\pi_{PG}^{eq}=Pc^{eq}$ decreases), but the equilibrium volume would decrease as well (i.e., $V^{eq}$ decreases). In this scenario, this simplified perturbation analysis using the equilibrium model predicts that the tissue will be more shrunken than the untreated tissue under the same conditions, as we saw in our experiments.

The supply and demand model can also be used to predict the qualitative behavior of the tissue in response to an applied load. Here, we use the model to predict the change in equilibrium hydration for an increase in PEG concentration, in two tissue specimens with different $\pi_{PG}$ vs V and Pc vs V curves. For the equilibrium condition to be satisfied, Equation (1), then $\pi_{PEG}$ must equal the difference between $\pi_{PG}$ and Pc. Graphically, this difference is represented by a vertical line segment whose height equals $\pi_{PEG}$ drawn to the left of the point of intersection between $\pi_{PG}$ vs V and Pc vs V. For the tissue with a steep $\pi_{PG}$ vs V and Pc vs V curves, the change in volume, $\Delta V=V'^{eq}-V^{eq}$, is small whereas for the tissue with a shallow $\pi_{PG}$ vs V and Pc vs V curves $\Delta V=V'^{eq}-V^{eq}$, is large for the same $\pi_{PEG}$.

A particularly powerful application of the supply and demand model is in examining the hypotheses about whether the loss of PG content or collagen network integrity occurs in the early stages of OA. In osteoarthritic cartilage, if one expects that collagen network integrity is reduced first, this would result in either a reduction of the slope of the Pc–V curve or a shift downward (We see that there is a difference between shifting a curve such as the pressure-volume relation (i.e., adding an offset) and changing its shape. The former does not affect the slope of the curve, i.e., the compressibility, but does affect the absolute pressure, while the latter affects both). This implies that in unloaded equilibrium, $\pi_{PG}^{eq}=Pc^{eq}$ decreases and $V^{eq}$ increases. The tissue will therefore be more swollen than normal tissue under the same conditions. If we suppose instead that PG to collagen ratio is reduced first, then the $\pi_{PG}$-V curve slope is reduced and/or the curve is shifted downward. Therefore $\pi_{PG}^{eq}=Pc^{eq}$ decreases (as before), but V decreases. Now the tissue will be more shrunken than a normal tissue under the same conditions. The observation that tissue swelling is an early manifestation of OA supports the former rather than the latter scenario.

In accordance with the method and model of the present invention, it is possible to assess the contributions of the collagen network and PG to bulk properties of the cartilage tissue matrix. For instance, it is possible to derive a simple approximate relationship between the differences of the slopes of $\pi_{PG}$ vs V and Pc vs V at the unloaded equilibrium volume, $V^{eq}$, and the resultant change in tissue equilibrium volume, $V'^{eq}-V^{eq}$, produced by a small applied isotropic load, which according to the hereinabove described mechano-osmotic titration embodiment is $\delta\pi_{PEG}$:

$$\left(\delta\pi_{PEG} = \left[\frac{d\pi_{PG}}{dV}\bigg|_{V^{eq}} - \frac{dP_c}{dV}\bigg|_{V^{eq}}\right]\right)[V'^{eq} - V^{eq}] \tag{7}$$

Figure 6:
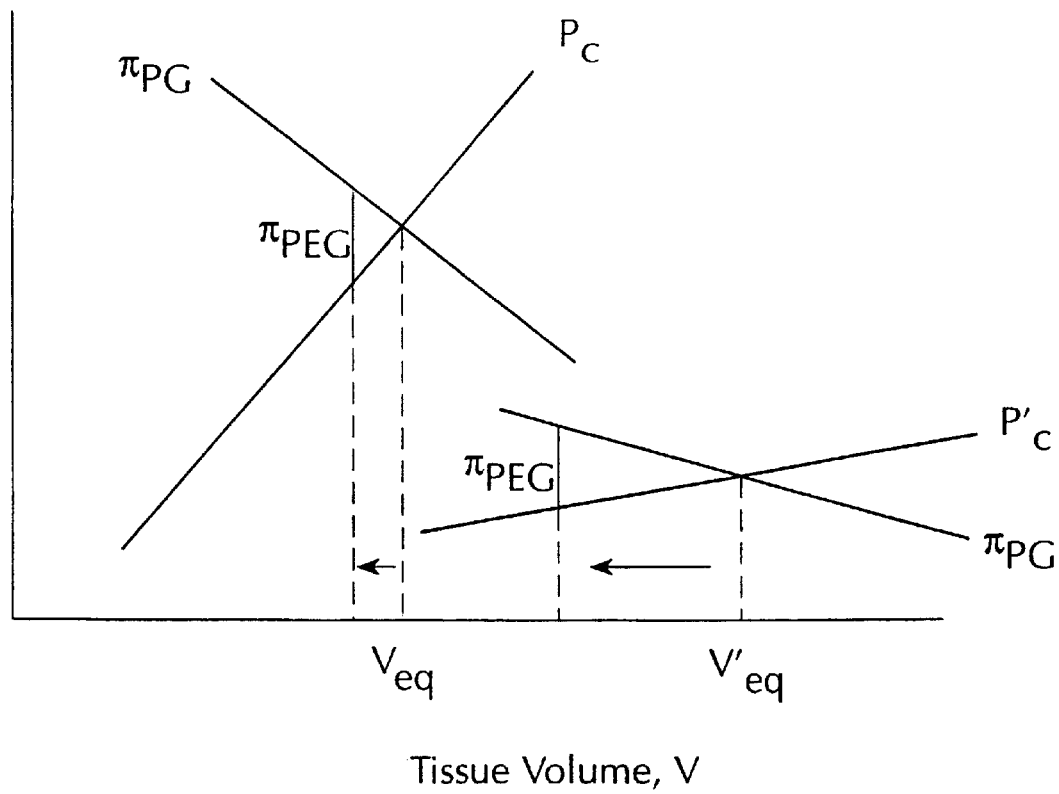
FIG. 6 illustrates applying the "supply and demand" model as a means to predict the equilibrium response of the cartilage specimens under an isotropic mechanical or osmotic load.

This expression is derived in the hereinbelow Appendix which follows the Example. We can extract a great deal of useful information about cartilage behavior from Eq. (7). First, for a given $\delta\pi_{PEG}$, the difference in the slopes is inversely proportional to the volume change. Since the difference in slopes is always negative, and since $\delta\pi_{PEG}$ is positive for a compressive osmotic load on the cartilage, the volume change, $(V'^{eq}-V^{eq})$, must be negative. So, as one expects, the equilibrium tissue volume decreases when a isotropic compressive load is applied. However, because of the inverse relationship between the difference in slopes and the difference in volumes, for a given applied osmotic stress, a small decrease in equilibrium tissue volume is associated with a large difference in slopes, while a large decrease in tissue volume is associated with a small difference in slopes. This is situation illustrated in FIG. 6. As we will see below, the difference in slopes can be related to a continuum mechanical measure of cartilage tissue matrix stiffness.

This finding can be applied to explain the difference in response of normal and OA tissue to isotropic loading. Normal adult cartilage specimens exhibit large difference of slopes and low hydration, as depicted schematically by the crossing lines in the upper left portion of the x-y axes in FIG. 6. OA adult cartilage specimens show smaller difference of slopes and a higher hydration, as depicted schematically by the crossing lines in the lower right hand portion of the x-y axes in FIG. 6. Using the arguments given above, the same applied PEG pressure at equilibrium, will produce a greater change in tissue volume or hydration in the OA specimen than in the normal specimen.

Features and advantages of the present invention may be further appreciated by comparison with models that aggregate PG and collagen phases. Existing biomechanical models of cartilage treat the cartilage tissue matrix as a single "solid-like" phase rather than as two distinct PG and collagen network phases. See, Lai, W. M., Hou, J. S., and Mow, V. C. (1991) *J. Biomech. Eng.* 113, 245–258; McCutchen, C. W. (1962) *Wear* 5, 1–17 Eisenberg, S. R. and Grodzinsky, A. J. (1985) *J. Orthop. Res.* 3, 148–159; and Mow, V. C., Kuei, S. C., Lai, W. M., and Armstrong, C. G. (1980) *J. Biomech. Engng.* 102, 73–84. The consequences of aggregating these phases vs separating them is elucidated by considering the response of the tissue to isotropic loading. Specifically, we examine the "tri-phasic" theory (Lai, W. M., Hou, J. S., and Mow, V. C. (1991) *J. Biomech. Eng.* 113, 245–258) of using it to predict the equilibrium free-swelling behavior of an isotropic, homogeneous cartilage specimen, since in this model, aggregation is viewed as a desirable and useful underlying principle.

We see that the total tissue stress for the aggregate tissue matrix (collagen+PGs+interstitial water) in thermodynamic equilibrium is given by combining the constitutive laws of the "fluid" and the "solid" phases (See, Eisenberg, S. R. and Grodzinsky, A. J. (1985) *J. Orthop. Res.* 3, 148–159):

$$T_{ij}(c) = \underbrace{2G_A(c)\epsilon_{ij} + [\lambda_A(c)\epsilon_{kk} - \beta_A(c)]\delta_{ij}}_{\text{solid part}} - \underbrace{P\delta_{ij}}_{\text{fluid part}} \tag{8}$$

where $T_{ij}$ is the total tissue matrix stress tensor, $\epsilon_{ij}$ is the tissue matrix strain tensor, $\epsilon_{kk}$ is the tissue matrix dilatation, $G_A(c)$ is the aggregate shear modulus of the tissue, $\lambda_A(c)$ is the aggregate Lamé constant of the tissue, $\beta_A(c)$ is the aggregate chemical stress, P is the hydrostatic pressure, and $\delta_{ij}$ is the identity tensor.

In equilibrium isotropic loading of the tissue in normal physiological saline, we can set P=0, and $\beta_A(c)$=0 by choosing physiological saline as the reference solution.

With no applied normal or shear stresses, or body force on the tissue:

$$T_{ij}=0 \text{ and } \epsilon_{ij}^{eq}=0 \text{ for all i and j} \tag{9}$$

Thus, the aggregate model of cartilage tells us that tissue matrix is free of stress and is unstrained. This result is true for any isotropic cartilage specimen although each may possess different material constants. Although the tissue matrix is free of stress, the collagen network is not. According to the present invention, we have seen that in normal human cartilage specimens the PGs exert an osmotic pressure of approximately 4 atm, and the collagen network is restraining them with a pressure of approximately 4 atm (as shown in the.Example provided hereinbelow). Moreover, with the cartilage tissue matrix "unstrained" in unloaded equilibrium, (i.e., $\epsilon_{ij}$=0), the collagen network is "inflated" to about 120% of its resting volume (the volume at which $Pc^{eq}$=0). We see, therefore, how aggregation of the two distinct cartilage matrix phases into a single solid-like tissue phase has masked internal stresses and strains that develop within tissue's individual constituents.

Our data from normal, OA, and trypsin-treated cartilage samples (described in the Example hereinbelow) also show that changes in the PGs, and collagen network or both can significantly affect the equilibrium tissue volume and hydration at which $P_{PG}^{eq} = Pc^{eq}$. The use of this equilibrium state as the reference state of cartilage can thus obfuscate comparisons between different tissue specimens, since their collagen networks are not in similar states of dilatation or deformation. A successful biomechanical model of tissues should facilitate comparisons of cartilage specimens (e.g., between different regions, between young and old, between load bearing an non-load bearing, etc.)

In addition, features and advantages of the present invention may be further appreciated by comparison with models that aggregate PG and collagen phases in "Free-swelling" in hypotonic saline. Suppose we were to perturb the ionic strength of the solvent, and allow the cartilage tissue to reach a new equilibrium state. Then $\beta_A(c)$ is longer zero. Summing the diagonal elements of the stress tensor in Eq. (8) we obtain:

$$0 = T_{ij}\delta_{ij} = 2G_A(c)\epsilon_{ij} + [\lambda_A(c)\epsilon_{kk} - \beta_A(c)]\delta_{ij}\delta_{ij} \tag{10a}$$

Realizing that $\epsilon_{ij}\delta_{ij} = \epsilon_{jj} = \epsilon_{kk}$, and $\delta_{ij}\delta_{ij} = 3$, this reduces to:

$$0 = (2G_A(c) + 3\lambda_A(c))\epsilon_{kk}^{eq} - 3\beta_A(c) \tag{10b}$$

Solving for the equilibrium tissue matrix dilatation, $\epsilon_{kk}$, we obtain:

$$\epsilon_{kk}^{eq}(c) = \frac{\beta_A(c)}{\frac{2}{3}G_A(c) + \lambda_A(c)} \tag{11}$$

The dilatation is thus the ratio of the chemical stress and a new equilibrium "aggregate" bulk or swelling modulus, $K_A(c)$, defined as:

$$K_A(c) = \frac{2}{3}G_A(c) + \lambda_A(c) \tag{12}$$

This quantity should not be confused with the "aggregate modulus", $H_A(C) = 2 G(c) + \lambda(c)$ most recently used by Mow et al. See, Mow, V. C., Kuei, S. C., Lai, W. M., and Armstrong, C. G. (1980) *J. Biomech. Engng.* 102, 73–84; Biot, M. A. (1941) *J. Appl Phys.* 12, 155–164; and Biot, M. A. (1955) *J. Appl. Phys.* 26, 182–185.

Suppose we now view tissue swelling in hypotonic solution with the two compartment model of the cartilage tissue matrix. Owing to differences in the type, composition, and distribution of charged groups within PGs and collagens, they respond differently to changes in ionic strength at physiological pH. The collagen network is largely uncharged in physiological saline, and its properties are largely insensitive to small perturbations of ionic strength. The PGs have a high concentration of fixed charged groups that are deprotonated in physiological saline. Therefore, small changes in ionic strength have a profound affect on their osmotic swelling pressure (primarily by affecting their mutual electrostatic repulsion, and secondarily, their entropic interactions). In our model, decreasing solvent ionic strength increases the first and second virial coefficients of the Eq. (2b). One does not gain this physical insight by examining Equation (11). In general, homogenizing the PG and collagen phases masks such selective or differential effects that a physical-chemical or biochemical perturbations have on the collagen and PGs. This claim also applies to understanding the changes in tissue behavior in response to changes in temperature, pH, solvent composition, and enzymatic treatment.

We can now relate our two-compartment model of the cartilage matrix in isotropic loading to models that aggregate the cartilage matrix into a single solid phase. From Equation (7) above, we show in the Example 2 that we can obtain an expression for the change in the applied isotropic stress divided by its fractional change in equilibrium volume:

$$\frac{\delta\pi_{PEG}}{\frac{V'^{eq} - V^{eq}}{V^{eq}}} \approx V^{eq}\left[\frac{d\pi_{PG}}{dV}\bigg|_{V^{eq}} - \frac{dP_c}{dV}\bigg|_{V^{eq}}\right] \tag{13}$$

The applied stress on the cartilage tissue is a compressive osmotic stress given by:

$$T_{ij} = -\delta\pi_{PEG}\delta_{ij} \quad (14)$$

Contracting the stress tensor results in a scalar which is three times the applied stress on the tissue specimen:

$$T_{ij}\delta_{ij} = -\delta\pi_{PEG}\delta_{ij}\delta_{ij} = -3\delta\pi_{PEG} \quad (15)$$

Again, we use the constitutive law in Equation (8) to describe this isotropic loading regime, and again P=0 and β(c)=0. Performing the same contraction on the right hand side of Eq. (8), and substituting the result of Eq. (15) produces:

$$-3\delta\pi_{PEG} = 2G_A(c)\epsilon_{ij}\delta_{ij} + \lambda_A(c)\epsilon_{kk}\delta_{ij}\delta_{ij} = [2G_A(c)+3\lambda_A(c)]\epsilon_{kk} \quad (16)$$

Now, we can solve for the ratio of the osmotic pressure and the tissue matrix dilatation:

$$-\frac{\delta\pi_{PEG}}{\epsilon_{kk}(c)} = \frac{2}{3}G_A(c) + \lambda_A(c) = K_A(c) \quad (17)$$

which equals the same the equilibrium "aggregate" bulk modulus in Equation (12).

In an equilibrium experiment in which the tissue matrix is loaded by an infinitesimally small isotropic stress, $\delta\pi_{PEG}$, the tissue dilatation, $\epsilon_{kk}^{eq}(c)$ can be approximated adequately by:

$$\epsilon_{kk}^{eq}(c) = \frac{V'^{eq} - V^{eq}}{V^{eq}} \quad (18)$$

Therefore, by comparing Equations (17) and (13), we now have derived two independent expressions for $K_A(c)$:

$$\frac{2}{3}G_A(c) + \lambda_A(c) = K_A(c) \approx V^{eq}\left[\frac{d\pi_{PG}}{dV}\bigg|_{V^{eq}} - \frac{dP_c}{dV}\bigg|_{V^{eq}}\right] \quad (19)$$

Equation (19) thus establishes a formal relationship between previous models that aggregate the PG and collagen network into a solid-like tissue matrix, and our model in which they are treated as distinct phases. Specifically, it relates the bulk modulus in the constitutive law of bi-phasic, and poroelastic models of isotropic cartilage specimens to the difference in the bulk moduli of the PG and collagen network phases at the (unloaded) equilibrium tissue volume, $V^{eq}$. In accordance with a further aspect of the present invention, therefore, it may be understood that the bulk moduli as determined according to the present invention may be used as the basis for the bulk modulus in the bi-phasic and poroelastic models.

Examining the form of Eq. (19) helps us see that the moduli or "material constants", G(c) and λ(c), that appear in previous continuum mechanical models of cartilage are not constants at all. Since in normal tissue, $\pi_{PG}$ vs V and Pc vs V are non-linear functions whose slopes change rapidly near the equilibrium volume, these moduli must depend on deformation and equilibrium volume. Thus, we must now view G(c) and λ(e) as "instantaneous equilibrium moduli" whose values apply meaningfully only in the unloaded equilibrium state of the tissue and for infinitesimally small perturbations around it.

It may therefore be appreciated that by separating individual contributions of the collagen network and PG phases, in accordance with the present invention, we are, for the first time, able to predict behaviors that cannot be explained using aggregate models of cartilage. For example, we can now determine the tissue's unstressed volume, the collagen network's hydration in equilibrium, its dilatation with respect to its unstressed state, and the collagen network and PG osmotic pressures when the tissue is unloaded or isotropically loaded in equilibrium. This information is not derivable from "biphasic" and subsequent "triphasic" models that aggregate the contributions of the collagen network and GAGs into a single "solid-like" elastic tissue, nor, more generally, can these models predict the state of stress and strain of the tissue's PG and collagen constituents.

By separating individual contributions of the collagen network and PG phases, we are also able to explain physiological phenomena that cannot be explained using models that aggregate these phases. For example, because the slope of Pc vs V drops in OA (as shown in the Example hereinbelow), the difference of the slopes of Pc vs V and $\pi_{PG}$ vs V and is much larger in normal tissues than in OA tissue. Therefore, we can immediately see why normal cartilage is dimensionally more stable than OA cartilage, as further described hereinbelow, and as described in connection with FIG. 6 hereinabove.

Aggregation of collagen and GAG phases, e.g., as in the tri-phasic theory, also prevents one from predicting how changes in collagen or GAG structure affect overall tissue function. These changes may be endogenous (e.g., associated with development, aging, or disease), exogenous (e.g., caused by a biochemical agent such as collagenase or trypsin or even by a genetic modification) or inherent (e.g., due to intra and interspecies variations among normal cartilage tissues).

Although equilibrium free-swelling represents the simplest mechanical loading regimen one could conceive of applying to cartilage, it nonetheless exposes crucial deficiencies in some existing biomechanical models of cartilage behavior, while concomitantly highlighting features and advantages of the present invention.

While in mechano-chemical equilibrium, the importance of the contributions of the PG and collagen constituents is immediately apparent, in other biologically relevant steady and unsteady loading regimens, such as in locomotion, characterizing cartilage dynamics adequately will ultimately require treating the PGs and collagen as separate phases rather than aggregating them. This is not only so because transient or time varying models of cartilage must exhibit the correct steady-state or equilibrium behaviors, (i.e., these models should still reduce to the proper time-independent or equilibrium form as a special or limiting case) but because the constitutive laws that are used to describe the relationships between stress and strain in the tissue matrix, and the hydrostatic pressure gradient and interstitial fluid flow, must now be modified. Specifically, the constitutive law used in Equation (7) does not correctly predict the form of the isotropic stress that is developed as a function of tissue volume or hydration or the tensile pressure exerted by the collagen network. This causes one to miscalculate the driving pressure used in Darcy's law. This affects predictions of interstitial velocity field for a given applied load, and thus the fluid expressed from the tissue during lubrication, as well as the transport of macromolecules and the ions connected within it. It also indirectly affects the prediction of the tissue's load bearing ability, and as well as alters predictions of electromechanical events, such as streaming potentials and stress generated potentials.

This equilibrium swelling model of cartilage also can be used to gain insight into the behavior of other connective tissues, such as intervertebral disk as well as tissues that are not strictly in equilibrium. For example, it is known that when the disk is removed from the bone, and placed in normal or hypotonic saline it first swells dramatically, and then shrinks. A plausible explanation of this phenomenon is that once the tissue is no longer constrained by the bone, the collagen network and elastin stiffness are not sufficient to match the osmotic pressure of the PGs initially, and the tissue must swell to a new larger network volume, where Pc is higher (because the network is more distended), but $\pi_{PG}$ is lower (because the PGs are now more dilute). However, the increased network hydration now increases the diffusivity of the PGs within the tissue, allowing them to diffuse out over the course of days. This loss of PGs from the tissue eventually lowers the $\pi_{PG}$ curve at each volume. In time, a new equilibrium ($\pi_{PG}$=Pc) is achieved at a lower pressure and a lower tissue volume or hydration. Even though these swelling and the diffusion processes are not strictly equilibrium processes, because their time scales are dramatically different, they be viewed into two quasi-equilibrium events, and easily represented using "Supply and demand" diagrams.

By separating individual contributions of the collagen network and PG phases we can also predict the aggregate effects of changing the physico-chemical environment of cartilage, such as its ionic strength or pH by assessing these effects on the individual phases. We can also consider the effects of biochemical or molecular modifications of adding proteases such as chondroitinase, stromolysin, hyaluronidase, etc. that may degrade the collagen network, the PG constituents or both, or proenzymes such as IGF-1 that might upregulate collagen or GAG content, composition, structure, and distribution.

The clinical potential of such a model will be further realized when all of its independent parameters can be measured or inferred non-invasively or semi-invasively. Then, it should be possible to determine the state of the cartilage locally in a manner that has not been possible to date both for diagnostic and therapeutic purposes. However, the herein described collagen network strength measuring methods and modeling approach should immediately be applicable in in vitro and drug effectiveness studies as there presently is no method available to assess the state of the collagen network and PG phases in tandem, in tissue specimens or in tissue constructs. With the development of novel tissue engineered extracellular matrix and cartilage constructs, this experimental and modeling approaches may be used to monitor tissue viability and mechanical integrity as they grow in culture or in vivo.

The following examples are presented to illustrate features and characteristics of the present invention, which is not to be construed as being limited thereto. For purposes of clarity of exposition and accuracy, and to ensure a complete disclosure, example 3 substantially corresponds to Example 1 in substance, and refers to the same set of experiments carried out in Example 1. Example 3, however, is intended to supplement example 1, and to ensure that all relationships and techniques are completely described. All references listed in example 3 are herein incorporated by reference, and the figures for Example 3 correspond to those referenced for Example 1.

EXAMPLE 1

The following experiments were performed in accordance with an equilibrium osmotic stress titration technique in which tissue specimens are exposed to a range of known osmotic stress by using calibrated solutions of osmotically active polyethylene glycol (PEG). Curves of equilibrium collagen network pressure vs. hydration were obtained by allowing cartilage specimens to come to mechano-chemical equilibrium at each different level of osmotic stress, that result in different degrees of collagen network hydration.

Figure 7:
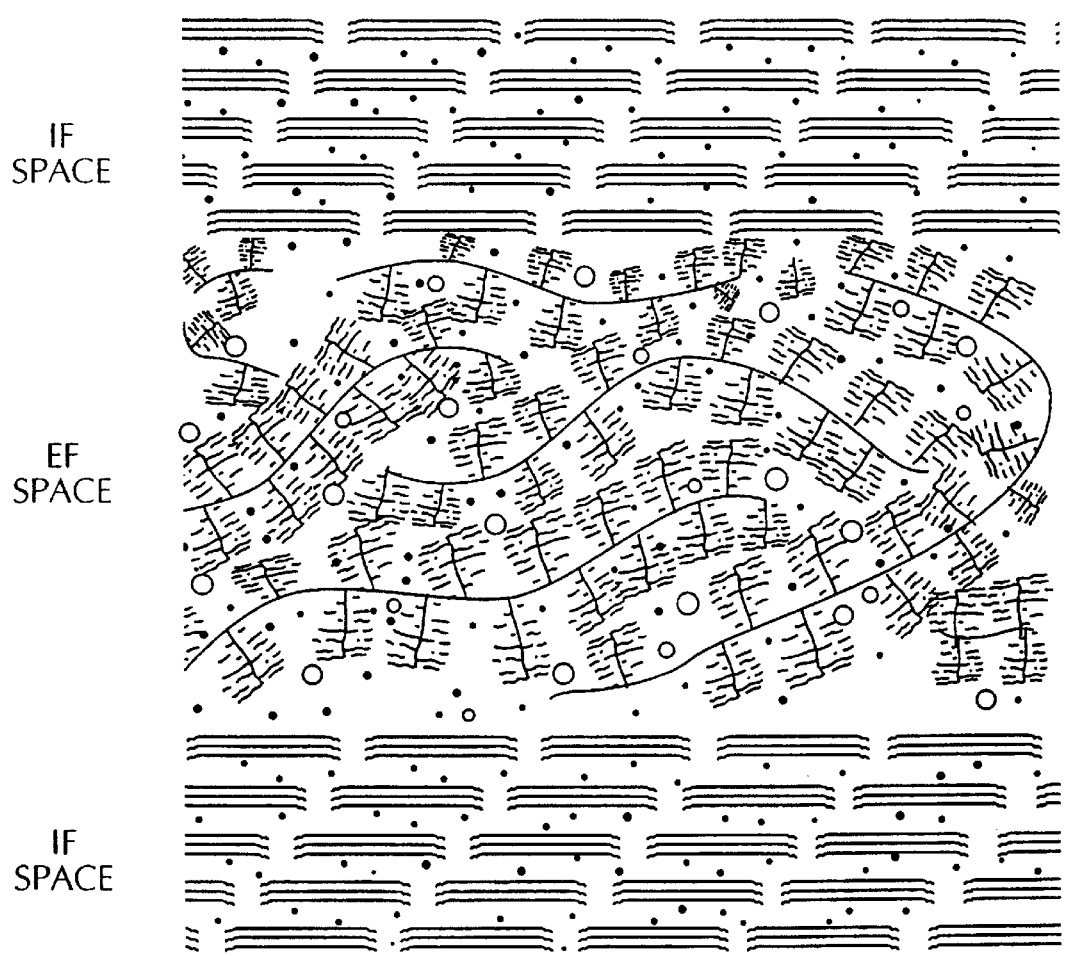
FIG. 7 illustrates the two-compartment model of the cartilage matrix structure.

More particularly, in accordance with the hereinabove mechano-osmotic embodiment of the present invention, $\pi_{PG}$ in the tissue can be determined from independent measurements of $\pi_{PG}$ vs PG concentration (or fixed-charge density, FCD) obtained using solutions of PGs extracted from cartilage. To infer $\pi_{PG}$ in cartilage from these data, the calculation of PG concentration must be based on the volume of fluid outside the collagen fibrils to which the PGs are confined. FIG. 7 illustrates the two-compartment model of the cartilage matrix structure. In particular, FIG. 7 schematically illustrates that the cartilage matrix consists of collagen fibrils—the E intrafibrillar (IF) compartment—from which proteoglycans (PGs) are excluded, and a space outside the collagen fibrils—the extrafibrillar (EF) compartment—where PGs exist as a concentrated solution. See, e.g., Lai, W. M., Hou, J. S., and Mow, V. C. (1991) *J. Biomech. Eng.* 113, 245–258.

We also need to know both the total water content of the tissue, and the water content within the fibrils. The former is determined from the difference between wet and dry tissue weights. The latter can be determined from collagen spacing measurements obtained by x-ray diffraction. However, intrafibrillar water content of the collagen fibers is not constant, but depends upon the osmotic stress acting on them. See, Maroudas, A., Wachtel, E., Grushko, G., Katz, E. P., and Weinberg, P. (1991) *Biochim Biophys Acta* 1073, 285–94, which is herein incorporated by reference.

The stress to which the collagen network is subjected in situ is augmented or diminished by changing the ionic strength of the interstitial fluid (thus changing the osmotic pressure exerted by the PG) or by changing the concentration of the osmotically active PEG in the external bath (thus altering the osmotic stress acting on the tissue sample across a dialysis membrane).

Since one of our aims is to compare different cartilage samples (e.g., healthy vs. diseased, old vs. young, etc.) whose composition may vary, we need to devise objective ways to compare them. Since the rate of turnover of collagen in cartilage is known to be extremely low and therefore, its quantity in a given joint remains relatively constant throughout adult life, we normalize mass in relation to collagen dry mass, and normalize volume in relation to collagen dry volume. See, Maroudas, A. (1980) in Studies in Joint Diseases: Metabolism of cartilagenous tissues: a quantitative approach (Maroudas, A. and Holborow, E. J., Eds.), pp. 59–86, Pitman Medical, London, which is herein incorporated by reference, and see also Libby, W. F., Berger, R., Mead, J. F., Alexander, G. V., and Ross, J. I. (1964) *Science* 146, 1170.

Tissue Sources

Femoral heads (ages 40, 55, and 90 years) were obtained at operations for femoral neck fractures or at post mortem. Two femoral condyles were obtained at an operation for total joint replacement. Joints were immediately placed in plastic bags, sealed, and then kept frozen at −20° C. Before handling, joints were soaked in physiological saline at 4° C. for one to two hours. This freezing and thawing protocol has been shown to preserve structural and mechanical properties of the tissue. See, Kempson, G. E. (1980) in The Joints and Synovial Fluid: The mechanical properties of articular cartilage (5okoloff, L., Eds.), pp. 177–237, Academic Press, New York.

Mild enzymatic treatment of the cartilage specimens was performed by incubating them in 1 mg trypsin solution (1:250) per ml 0.15M NaCl for approximately five hours at room temperature, with subsequent washings in 0.15M NaCl containing enzyme inhibitors. This mild treatment results in partial removal of the PG, and a concomitant decrease of PCD of approximately 40% (present data). Treatments with trypsin carried out for longer periods of time and at higher temperatures, though they removed almost all the PG, were shown not to affect collagen fibril structure, composition, or uniaxial tension response of the tissue. See, Maroudas, A., Wachtel, E., Grushko, G., Katz, E. P., and Weinberg, P. (1991) *Biochim Biophys Acta* 1073, 285–94; Schmidt, M. B., Mow, V. C., Chun, L. E., and Eyre, D. R. (1990) *J Orthop Res* 8, 353–363; Chun, L. E., Koob, T. J., and Eyre, D., (1986) in Transactions of the 32nd Annual Meeting of the ORS, New Orleans, 96; and Volpe, M. and Katz, E. P. (1991) *J. Biomech.* 28, 67–77.

Specimen Preparation

Full-depth cartilage plugs, approximately 7 mm in diameter, were cored from the superior surface of the normal femoral head. The cartilage showed no sign of fibrillation as assessed by the methods of Byers et al. and Indian ink staining. See Byers, P., Contemponi, C. A., and Farkas, T. A. (1970) *Ann. Rheum. Dis.* 29, 15–21; and Meachim, G. (1972) *Ann. Rheum. Dis.* 31, 457464. Similar plugs were obtained from osteoarthritic (OA) knees, the surfaces of which were carefully characterized by the same procedures as above. In the case of OA specimens, the surface appearance ranged from nearly intact to severely fibrillated. See, Bayliss, M. T., Venn, M., Maroudas, A., and Ali, S. Y. (1983) *Biochem J* 209, 387–400, which is herein incorporated by reference. Plugs were sliced on a freezing microtome (Leitz), and approximately 1 mm thick sections from the "middle" zone were used in the present series of experiments. Slices from the middle zone were used because in normal cartilage, the PG contents and fixed-charge densities are known to be relatively uniform in this region. See, Maroudas, A., Evans, H., and Almeida, L. (1973) *Ann. Rheum. Dis.* 32, 1–9; Maroudas, A. and Venn, M. (1977) *Ann Rheum Dis* 36, 399–406; and Maroudas, A., Muir, H., and Wingham, J. (1969) *Biochem. Biophys. Acta* 177, 492–500. We weighed the sections as cut, and then soaked them in 0.15M NaCl (physiological saline) overnight, and again measured their equilibrium weight.

Materials

Polyethylene glycol (PEG) 20,000 DA was obtained from Fluka (Switzerland), and purified by ultrafiltration through a 3,000 DA membrane. Trypsin and proteinase inhibitors were obtained from Sigma Chemicals (St. Louis). Radioactively labeled $Na^{+22}$ was obtained from Amersham International (UK). Spectrapor dialysis tubing (MWCO 1,000 DA) was obtained from Spectrum Medical (CA).

Methods

Both tissue swelling pressure and the osmotic pressure of the proteoglycan solutions were measured by equilibrium dialysis against calibrated PEG solutions. In the experiments modeled here, the cartilage specimens are either equilibrated in physiological saline (0.15M NaCl) with no load applied, equilibrated in hypotonic saline (0.015M NaCl) with no load applied, or equilibrated in physiological saline (0.15M NaCl) with an isotropic osmotic stress applied by dialysing them in PEG solutions of known osmotic pressure. See, Urban, J. P., Holm, S., Maroudas, A., and Nachemson, A. (1977) *Clin Orthop*, 101–14; and Maroudas, A. and Urban, J. (1983) in Skeletal Research: An Experimental Approach: In vitro methods for studying articular cartilage and intervertebral disc (Kunin, A. S. and Simmons, D. J., Eds.), pp. Academic Press, Inc., New York, which are herein incorporated by reference. FIG. 2 shows a schematic diagram of the experimental system used to load the cartilage specimens isotropically with a dialysis sack.

Calibration of PEG Solutions

Figure 8:
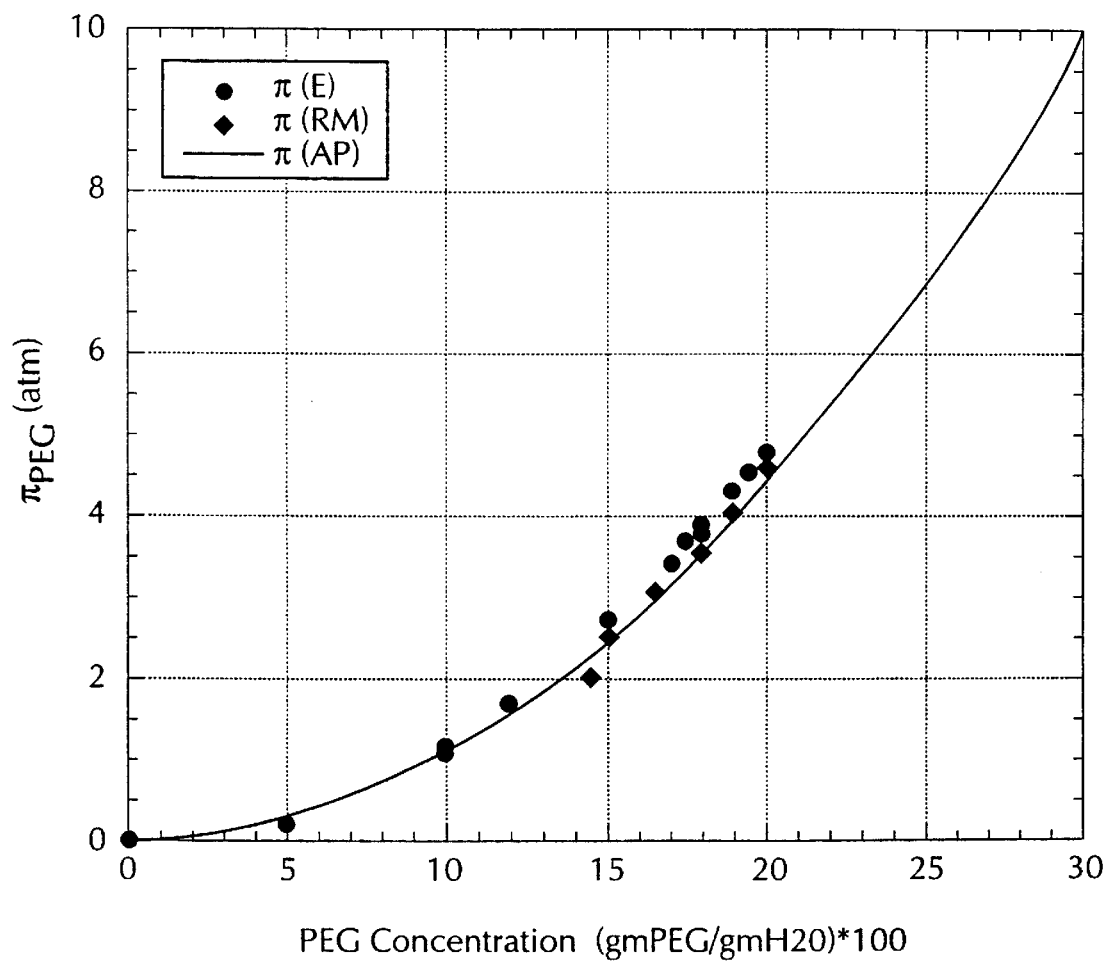
FIG. 8 shows the osmotic pressure of PEG (20,000 MW) vs PEG concentration, wherein data points are pooled from Ramon and Maroudas (RM) and Erlich (E) (both at 4° C.), and the solid line shows an empirical relationship given by Parsegian et al. (AP) (at 7° C. in pure water); See: Erlich, S. (1994) The influence of age and degeneration on changes in the osmotic pressure of the proteoglycans in the intervertral disc, 66; and Parsegian, V. A., Rand, R. P., Fuller, N. L., and Rau, D. C. (1986) Methods of Enzymology 127, 400416.

FIG. 8 shows calibration curves of PEG osmotic pressure vs. PEG concentration at 4° C., obtained from measurements in our laboratory as well as published data of Parsegian (Parsegian, V. A., Rand, R. P., Fuller, N. L., and Rau, D. C. (1986) *Methods of Enzymology* 127, 400–416) with which our data show good agreement. The apparatus used for measuring the osmotic pressure of PEG consisted of a specially adapted stirred ultrafiltration cell fitted with a semi-permeable membrane. The solution osmotic pressure was balanced by applied Nitrogen pressure. The cell was capable of withstanding applied pressures of up to 5 atm.

Equilibrium Dialysis of Cartilage Specimens Against PEG Solutions

For compressing cartilage specimens, PEG solutions were prepared in 0.15M and 0.015M NaCl, ranging from 3 gm PEG in 100 gm solvent ($\pi_{PEG}$ approximately equal to 0.1 atm) to 27.5 gm PEG in 100 gm solvent ($\pi_{PEG}$ approximately equal to 10 atm). The $\pi_{PEG}$ vs. PEG concentration data in 0.015 M and in 0.15 M NaCl were found to coincide (authors' unpublished data).

Since PEG has been found to penetrate cartilage, the tissue samples were not placed directly in the PEG solution, but were separated from it by dialysis tubing (Spectrapor 1,000 MWCO), which minimizes PEG penetration although does not entirely eliminate it. See, Urban, J. P., Maroudas, A., Bayliss, M. T., and Dillon, J. (1979) *Biorheology* 16, 447–64, which is herein incorporated by reference. Control experiments were performed (showing that differences between dry tissue weight determined before and after dialysis against PEG were negligible), to ensure that under our experimental conditions, there was no significant PEG penetration.

Cartilage slices were equilibrated in each solution for approximately 48 hours at 4° C. as this has been found to be sufficient to achieve mechano-chemical equilibrium, while at the same time minimizes PEG penetration. At the end of each test, slices were removed, from the dialysis tubing and weighed immediately. They, were then reequilibrated in 0.15M NaCl and reweighed to ensure that they returned to their baseline weight. At this stage, the slices were ready for reequilibration in another PEG solution. In this way, curves of swelling pressure versus cartilage weight were obtained in a manner described below. Note that all weighings were carried out as previously described. See, Schneiderman, R. and Maroudas, A. (1995) *Archives of Biochemistry and Biophysics* 324, -172, which is herein incorporated by reference. Tissue samples, placed in pre-weighed stoppered vials, were weighed using an analytical balance to five decimal places. Reproducibility was between 0.2–0.3%. All solutions contained 0.01% (wt./vol.) $NaN_3$. We periodically weighed the specimens in 0.15M NaCl to ensure that there were no significant changes in tissue weight during the experiment, and periodically measured FCD to ensure that no PG was lost. We discarded samples from the study that exhibited significant changes in weight and/or FCD.

To obtain dry weights, the specimens were dried until reaching a constant weight in a freeze drier. This usually took 24 to 36 hours, depending on the initial tissue weight. The specimens were weighed in stoppered vials that had been pre-weighed. Sometimes the samples were freeze-dried several times during a series of experiments (e.g., to check for PEG penetration) and subsequently rehydrated. This treatment was found not to alter any of the tissue properties that we were testing.

The experimental procedure is straightforward but success depends on extremely careful, accurate and reproducible weight determinations, both wet and dry. For wet weight it is essential—before one weighs the sample—to blot both surfaces to remove all extraneous liquid; blot gently so as not to express the interstitial fluid, yet swiftly so as not to allow loss of water through evaporation.

FCD Determination

Measurements of cartilage's total fixed-charge (mEq per gm total tissue) were obtained by means of the Tracer Cation Method using $Na^{+22}$ in hypotonic saline (0.015M NaCl). See, Maroudas, A. and Thomas, H. (1970) *Biochimica et Biophysica Acta* 215, 214–216.

Osmotic Pressure of PG Solutions

Figure 9:
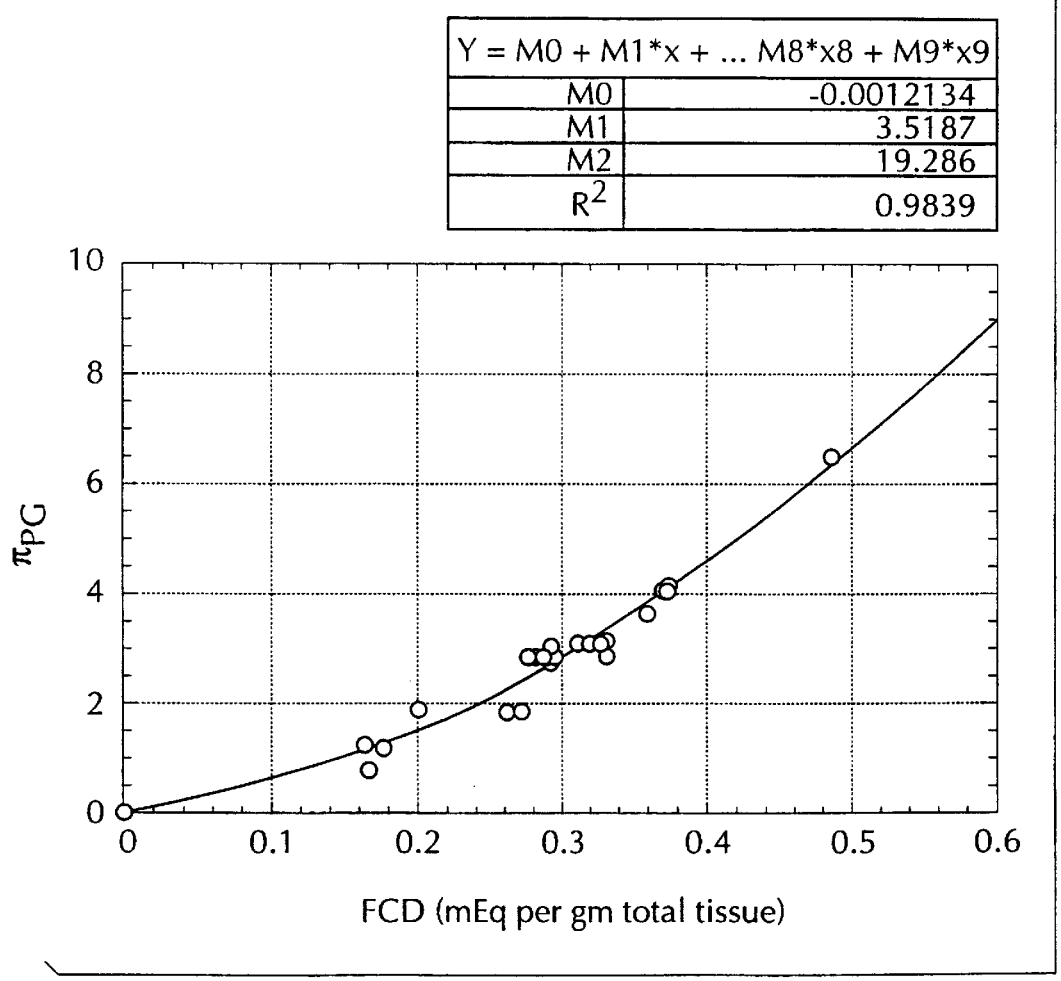
FIG. 9 depicts a polynomial least-squares fit to data points for proteoglycan osmotic pressure vs. fixed charge density for solutions of proteoglycans extracted from human articular cartilage (ages 50–80)

In the herein described experiments, we did not carry out these experiments, but have used previous experimental results: Data of Urban et al. for $\pi_{PG}$ vs FCD in PG solutions, which have been recently recalculated, and new experimental data from our lab were combined, and then fit with a quadratic function, in accordance with equation (2a) described hereinabove, by using non-linear regression to obtain the virial coefficients: M0, M1, and M2. The data set and the fitted quadratic function are shown in FIG. 9. Note that this empirical relationship includes both electrostatic and entropic contributions. See, Urban, J. P., Holm, S., Maroudas, A., and Nachemson, A. (1977) *Clin Orthop*, 101–14.; Maroudas, A. and Grushko, G. (1990) in Methods in Cartilage Research: Measurement of Swelling Pressure of Cartilage (Maroudas, A. and Kuettner, K. E., Eds.), pp. 298–301, Academic Press, San Diego; and Erlich, S. (1994) The influence of age and degeneration on changes in the osmotic pressure of the proteoglycans in the intervertral disc, , 66.

More particularly, for the data of Urban et al., osmotic pressures of PG solutions were obtained by using equilibrium dialysis against PEG solutions. Urban et al. calculated the osmotic pressures of these PEG solutions using virial coefficients reported for 25° C. by Edmond and Ogston who assumed that the virial coefficients did not vary with temperature. Subsequently, direct measurements of PEG osmotic pressure at lower temperatures were performed by Parsegian et al., and independently in our laboratory. The assumption of constant virial coefficients was shown to be incorrect. We recalculated the data of Urban et al. using new experimental calibrations of PEG solutions. See, Urban, J. P., Maroudas, A., Bayliss, M. T., and Dillon, J. (1979) *Biorheology* 16, 447–64.; Edmond, E. and Ogston, A. G. (1968) *Biochem J.* 109, 569–576; Parsegian, V. A., Rand, R. P., Fuller, N. L., and Rau, D. C. (1986) *Methods of Enzymology* 127, 400–416.

Collagen Analysis

Cartilage samples were hydrolyzed in 6M HCl at 110° C. for 20–24 hours, dried overnight in a Speed Vac (Savant, Farmingdale), and dissolved in 0.1 M sodium borate buffer (pH 8.0). A 200 mL aliquot containing 0.76 mg tissue (dry weight) was derivatized with 200 mL 6 mM g-fluorenylmethyl chloroformate (Fluka, Switzerland) in acetone for 5 min. at room temperature. Termination of the reaction was performed by extraction with pentane. Amino acid analysis was performed according to Miller et al. See, Miller, E. J., Narkates, A. J., and Niemann, M. A. (1990) *Anal. Biochem.* 190, 92–97. The amount of collagen (in mg) was determined by the amount of hydroxyproline, assuming 300 residues per triple helical molecule with a molecular weight of 300,000 DA.

Intrafibrillar Water Determination

It was shown by Katz et al. and Maroudas et al. that, as described hereinabove, collagen fibril hydration is not constant (defined as the mass of intrafibrillar water, $m_{IFH2O}$, divided by the mass of dry collagen, $m_c$) is not a constant, but is a function of the external stress acting on the collagen fibrils. See, Katz, E. P., Wachtel, E. J., and Maroudas, A. (1986) *Biochim Biophys Acta* 882, 136–9; and Maroudas, A., Wachtel, E., Grushko, G., Katz, E. P., and Weinberg, P. (1991) *Biochim Biophys Acta* 1073, 285–94.

We determined the relationship between intrafibrillar water and extrafibrillar osmotic pressure from previous experimental data. Intrafibrillar water content was calculated from collagen spacing data for human articular cartilage as measured by low-angle equatorial x-ray scattering at varying levels of osmotic stress. Note that the data include both native specimens, in which the osmotic stress is due to the osmotic pressure of the extrafibrillar PGs, and PG-free specimens in which the osmotic stress is provided by PEG. See, Maroudas, A., Wachtel, E., Grushko, G., Katz, E. P., and Weinberg, P. (1991) *Biochim Biophys Acta* 1073, 285–94; Katz, E. P., Wachtel, E. J., and Maroudas, A. (1986) *Biochim Biophys Acta* 882, 136–9; and Wachtel, E., Maroudas, A., and Schneiderman, R. (1995) *Biochim Biophys Acta* 1243, 239–43, which are herein incorporated by reference.

Figure 10:
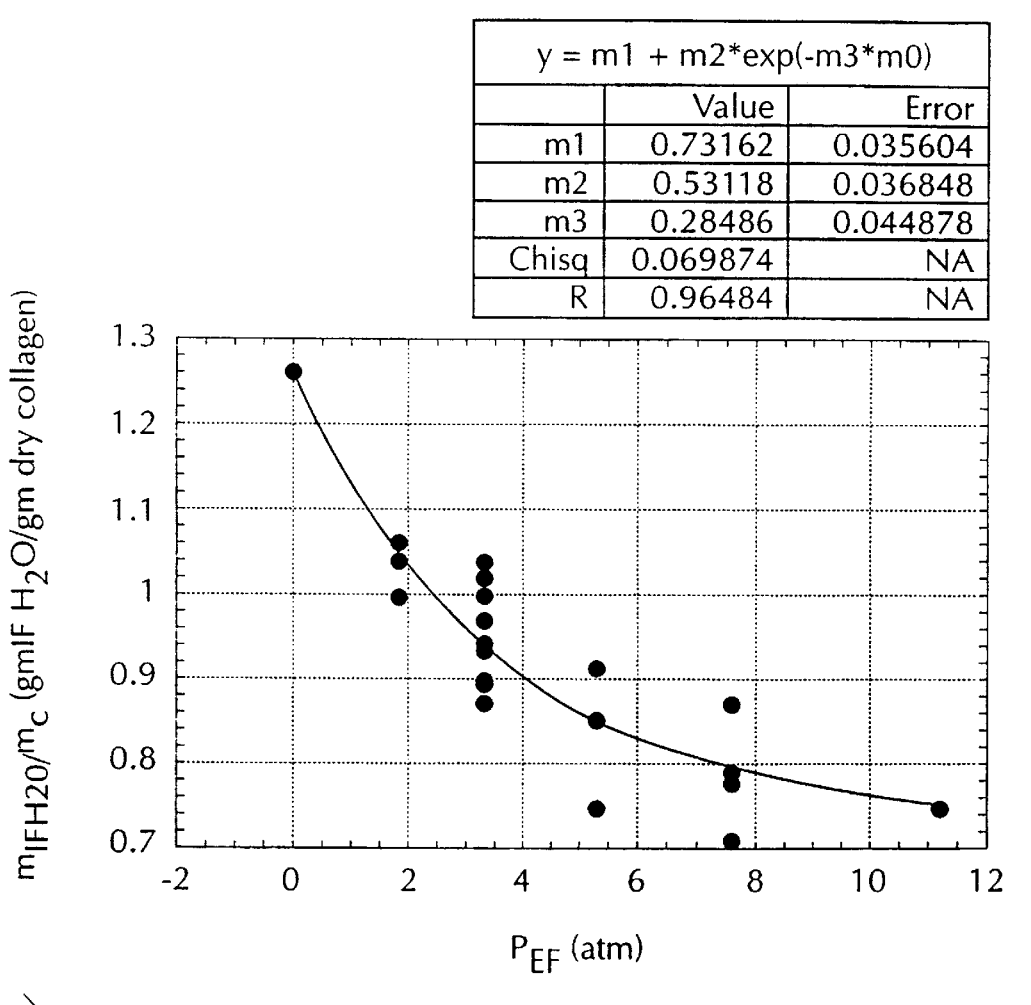
FIG. 10 shows intrafibrillar (IF) water content (measured by the ratio of mass of intrafibrillar water and the mass of dry collagen) vs osmotic stress in the extrafibrillar (EF) compartment.

We fit the intrafibrillar water content to an exponentially decaying function of the osmotic pressure in the extrafibrillar compartment, $\pi_{EF}$, using non-linear regression in accordance with equation (4) described hereinabove. Both the data and the fitted function are shown in FIG. 10. The use of an exponentially decaying function in this regime of intermolecular spacing is consistent with recent findings of Leikin et al. See, Leikin, S., Rau, D. C., and Parsegian, V. A. (1994) *Proc. Natl. Acad. Sci. USA* 91, 276–280.

Inferring Pc vs Collagen Network Hydration

Our analysis is based on several simplifying assumptions, including the following enumerated assumptions. 1) The matrix consists of two compartments, each with uniform composition, material properties, and structure on the scale of the specimen: See, Venm, M. and Maroudas, A. (1977) *Ann Rheum Dis* 36, 121–9.

2) The PG osmotic pressure, $\pi_{PG}$ within the tissue is the same as the osmotic pressure of isolated PGs when the PG concentration is expressed on the basis of extrafibrillar water: See, Maroudas, A., Wachtel, E., Grushko, G., Katz, E. P., and Weinberg, P. (1991) *Biochim Biophys Acta* 1073, 285–94; Grushko, G., Schneiderman, R., and Maroudas, A. (1989) *Connective Tissue Research* 19, 149–176; and Maroudas, A. and Grushko, G. (1990) in Methods in Cartilage Research: Measurement of Swelling Pressure of Cartilage (Maroudas, A. and Kuettner, K. E., Eds.), pp. 298–301, Academic Press, San Diego.

3) The relationship between $_{PG}$ and FCD based on pooled data for PG extracted from normal aged adult human femoral heads (age 50–80) applies to all of our specimens. See, Erlich, S. (1994) The influence of age and degeneration on changes in the osmotic pressure of the proteoglycans in the intervertral disc, Masters Thesis, (as cited herein) 66,; and Urban, J. P., Maroudas, A., Bayliss, M. T., and Dillon, J. (1979) *Biorheology* 16, 447–64.

4) Intrafibrillar water content does not explicitly depend on Pc.

5) The collagen network within the specimen is isotropic and homogeneous. In this pilot study, we have deliberately chosen cartilage specimens from the middle zone, in which the proteoglycan content is substantially uniform, and in which the collagen network does not have a well-defined orientation. See, Venn, M. and Maroudas, A. (1977) *Ann Rheun Dis* 36, 121–9.

The four equations relating $\pi_{PG}$, $m_{EFH2O}$, $m_{IFH2O}$, and $FCD_{eff}$ (where $m_{EFH2O}$ and $m_{IFH2O}$ are the respective masses of the extra- and intrafibrillar water; and $FCD_{eff}$ is the fixed charge density in mEq per gm of extrafibrillar water), which are detailed hereinabove, have been presented previously in: Maroudas, A. and Grushko, G. (1990) in Methods in Cartilage Research: Measurement of Swelling Pressure of Cartilage (Maroudas, A. and Kuettner, K. E., Eds.), pp. 298–301, Academic Press, San Diego. Here, they are used with Eq. (1b) to solve for $m_{EFH2O}^{eq}$, $m_{IFH2O}^{eq}$, $\pi_{PG}^{eq}$, $FCD_{eff}^{eq}$, and $Pc^{eq}$ to characterize the equilibrium state of cartilage in isotropic loading.

To determine $\pi_{PG}$ vs $FCD_{eff}$ in cartilage we used the relationship for extracted proteoglycans (Equation 2) and the relationship representing conservation of charge of the PGs (since in our experiments, no charge is lost or gained during tissue compression or swelling) in order to relate $FCD_{eff}$ to the measured $FCD_{TOTALH2O}$—the fixed charge density in mEq per gm of total water in the unloaded cartilage.

In addition, we applied the equation of conservation of mass (equation (5a) or equation (5b) hereinabove) of the tissue constituents, which reflects the physical situation that during swelling or compressing cartilage specimens, no PG or collagen mass is gained or lost, tissue mass can only change by expressing or imbibing water.

Once all independent parameters ($\pi_{PEG}$, $FCD_{TOTALH2O}$, $m_c$, $m_{dry}$, and M (i.e., Mwet)) were determined for each specimen (using representative calculations given in the Table of FIG. 11), then the values of the four dependent variables ($m_{EFH2O}$, $m_{IFH2O}$, $\pi_{PG}$, and $FCD_{eff}$) are completely specified at each equilibrium state by the four non-linear independent equations described hereinabove (i.e., equations 2b, 3, 4, and 5b).

These simultaneous equations were solved here by guessing initial equilibrium values and iterating until final equilibrium values of $m_{IFH2O}^{eq}$, $m_{EFH2O}^{eq}$, $\pi_{PG}^{eq}$, and $FCD_{eff}^{eq}$ were obtained, as illustrated in the Table of FIG. 12. Then, using $\pi_{PEG}$ and $\pi_{PG}^{eq}$ in Equation (1b), we calculate $Pc^{eq}$. More specifically, for each value of applied stress, $\pi_{PEG}$, the first step in calculating $P_c$ is to determine F. This is done by trial and error as follows: we guess F, calculate $m_{IFH2O}$ ($m_{EFH2O}=m_{totalH2O}-m_{IFH2O}$); we then calculate $FCD_{eff}$ based on $m_{EFH2O}$, obtain $\pi_{PG}$ from Eq. (2b) (FIG. 9) and check whether the value of F we guessed corresponds to the calculated value of $\pi_{PG}$ using Eq. (4) (FIG. 10). If not, a new value is chosen and the cycle is repeated until subsequent values of F coincide. We then proceed to the definitive calculation of $FCD_{eff}$ and hence $\pi_{PG}$ and $P_c$.

In this experiment we defined a collagen network hydration parameter as (Vt−Vc)/Vc according to equation (6a) hereinabove in order to describe the degree of collagen network inflation. In a simple polymer gel, network hydration is usually defined as the volume of the fluid encompassed by the network divided by the volume of the polymer. Since cartilage tissue is a composite medium, this concept must be extended in a meaningful way. To compare different states of deformation of different tissues, we should measure tissue volume in relation to a volume that is assumed to be constant in all of our specimens. Therefore, in this experiment, we defined the equilibrium tissue hydration as the ratio of the total tissue volume outside the dry collagen divided by the volume of dry collagen. The quantity (Vt−Vc)/Vc of equation 6a represents the volume of the tissue, less the dry collagen volume divided by the dry collagen volume, wherein $v_{H2O}=1$ cm$^3$/gm, $v_P=0.74$ cm$^3$/gm, $v_{GAG}=0.54$ cm$^3$/gm, and $v_c=0.74$ cm$^3$/gm are the partial specific volumes of water, non-collageneous protein, glycosaminoglycans, and collagen, respectively. See, Fasman, G. D. (1975) Handbook of Biochemistry and Molecular Biology: Physical and Chemical Data, CRC Press, Boca Raton; Ogston, A. G., Preston, B. N., and Wells, J. D. (1972) *Proc. R. Soc. Lond.* 333, 297–316; (40) Noda, H. (1972) *J. Biochem.* (Japan) 71, 699–703.

For non-collagenous proteins we have assumed the same density as for collagen (see the Table of FIG. 13). Note, however, that there are many possible variations in expressing the degree of "hydration" in a physically and quantitatively meaningful and satisfying manner in addition to those expressed in equations 6a–c.

Most of the experiments were carried out in 0.15 M NaCl. However, to extend the range of Pc to higher hydrations, some specimens were also equilibrated in 0.015 M NaCl. Without PEG, the equilibrium in 0.015 M NaCl is described by:

$$Pc_{(SW)}^{(0.015M)}=\pi_{PG(SW)}^{(0.015M)}$$

where $Pc_{(SW)}^{(0.015M)}$ and $\pi_{PG(SW)}^{(0.015M)}$ represent respectively the collagen restraining pressure and PG osmotic pressure in the swollen state in 0.015M NaCl. Clearly, to determine Pc we need to know the corresponding $\pi_{PG}$.

Unfortunately, when these experiments were conducted we had no data on the osmotic pressure of extracted PG in hypotonic solutions. Therefore, an indirect procedure was used, which is described as follows.

Procedure for Determining Pc in Cartilage in Hypotonic Solutions

In essence, the method consists in finding, by trial and error, the PEG concentration in 0.015M NaCl (and hence $\pi_{PEG}$) which was just sufficient to shrink a given cartilage specimen to the same water content as it had in 0.15M NaCl, without PEG. The equilibrium in the swollen state in the presence of PEG is described by the equation:

$$Pc_{(o)}^{(0.015M)}+\pi_{PEG(o)}^{(0.015M)}=\pi_{PG(o)}^{(0.015M)}$$

If we assume Pc is a function of tissue volume alone, $Pc_{(o)}^{(0.015M)}=Pc_{(o)}^{(0.15M)}$, the latter quantity having already been determined. We also found that the osmotic pressures of PEG solution in 0.015M NaCl are the same as in 0.15 M NaCl (unpublished data), therefore, we know $\pi_{PEG(o)}^{(0.015M)}$ from data in FIG. 8. Thus, we calculate $\pi_{PEG(o)}^{(0.015M)}$ from the previous equation.

For normal specimens, the increase in water content due to swelling in 0.015 M NaCl is of the order of only 1% to 2%, so that the change in $FCD_{EFF}$ and hence in $\pi_{PG}$ from the unswollen state is very small and can be neglected: thus, we can assume that $\pi_{PG(SW)}^{(0.015M)}$ is approximately equal to $\pi_{PG(o)}^{(0.015M)}$ and substitute the latter value into the previous equation to obtain $Pc_{(SW)}^{(0.015M)}$ corresponding to the increase in the tissue volume.

In the case of OA specimens, where the increase in hydration due to swelling in 0.015 M NaCl can reach 10%, one cannot assume that $\pi_{PG(SW)}^{(0.015M)}$ is approximately equal to $\pi_{PG(o)}^{(0.015M)}$. To estimate $\pi_{PG(o)}^{(0.015M)}$ we assume a linear relationship of $\pi_{PG}^{(0.015M)}$ vs hydration over the range of swelling in question and calculate $\pi_{PG(SW)}^{(0.015M)}$ from $\pi_{PG(o)}^{(0.015M)}$ in this manner.

Results

When cartilage specimens were excised from the joint, and equilibrated in 0.15M NaCl they swelled by less than 1% (by tissue weight). On the other hand, initial swelling of the OA cartilage specimens in 0.15M NaCl was as high as 7%. Normal specimens transferred from 0.15M NaCl to 0.015M NaCl swelled by 1% to 2%, while OA specimens swelled up to 10%. This agrees with previous findings. See, Maroudas, A. and Venn, M. (1977) *Ann Rheum Dis* 36, 399–406; Maroudas, A. (1976) *Nature* 260, 808–9.

Figure 14:
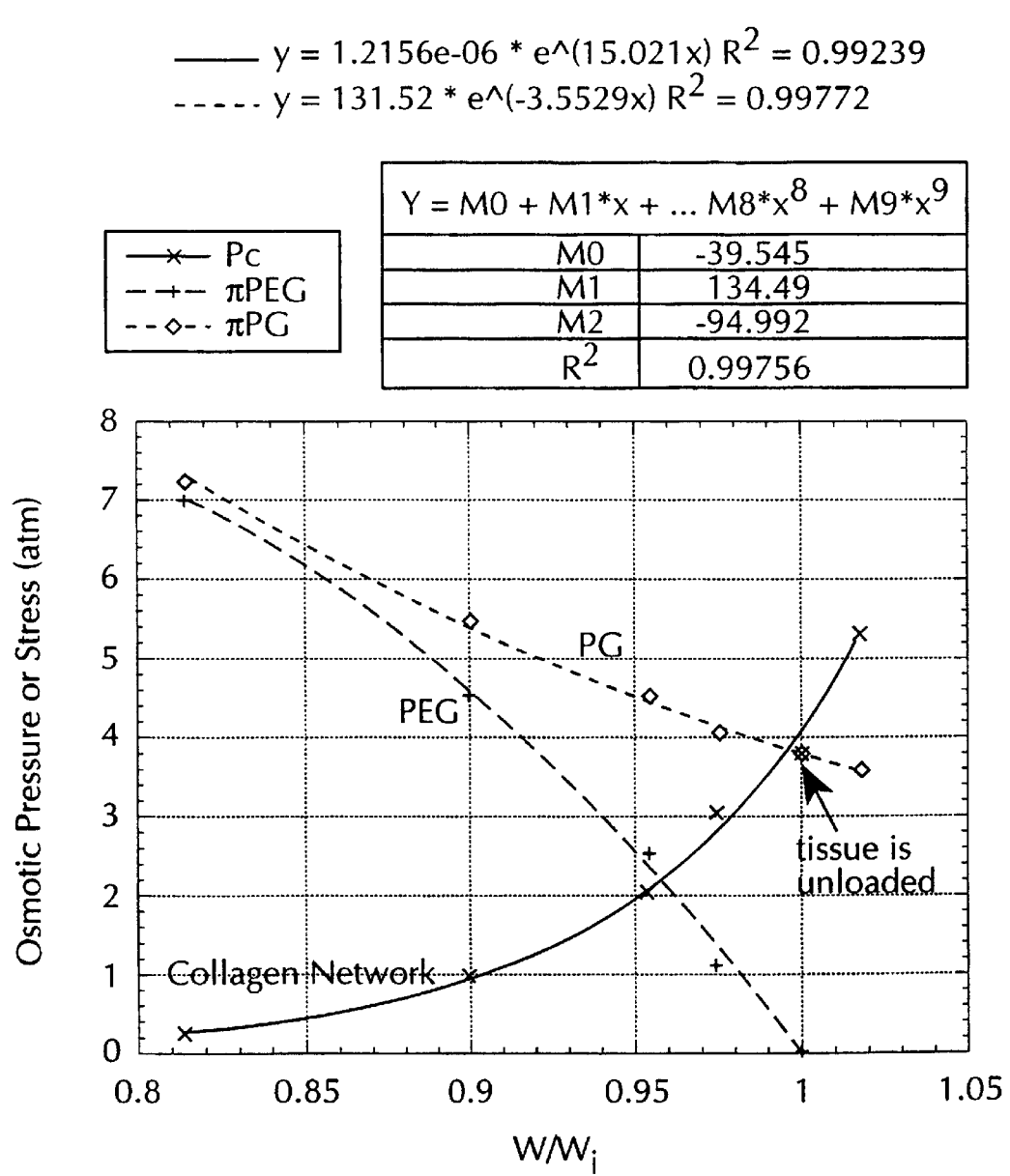
FIG. 14 shows collagen network restraining stress, proteoglycan osmotic pressure, and PEG osmotic pressure vs. the ratio of tissue wet weight and initial tissue wet weight $(W/W_i)$ for a typical normal 55 year old cartilage specimen in mechano-chemical equilibrium with different levels of osmotic loading (For $W/W_i>1$ swelling was achieved by immersion in 0.015 M NaCl, while for $W/W_i<1$, deswelling was achieved by equilibrium dialysis against PEG solutions)

FIG. 14 shows the measured equilibrium pressures Pc, $\pi_{PG}$, and $\pi_{PEG}$ vs. normalized tissue wet weight, W/W$_i$, for a typical normal cartilage specimen. (Note that W/W$_i$ denotes the same quantity as M/M$_o$—the equilibrium tissue wet weight divided by the equilibrium tissue wet weight measured in physiological saline without any applied load). The point of intersection of the Pc and $\pi_{PG}$ curves represents the state of unloaded equilibrium, (i.e., for no applied pressure) where $\pi_{PEG}$=0. This state corresponds to a hydration W/W$_i$=1. Although the tissue is unstrained, the collagen network is in tension—Pc=$\pi_{PG}$≈3.9 atm. As we increase $\pi_{PEG}$ from 0 atm, Pc decreases and $\pi_{PG}$ increases. Pc approaches 0 atm after a decrease in W/W$_i$ of about 20% (i.e., a decrease in hydration of about 30%). As we increase $\pi_{PEG}$ further, $\pi_{PG}$ is close to $\pi_{PEG}$, and consequently, Pc remains close to zero. The coincidence of $\pi_{PG}$ and $\pi_{PEG}$ vs hydration has been previously observed at low tissue hydrations and is consistent with the Ogston picture of cartilage that its collagen matrix can exert tension to restrain PGs, but not support compression. See, Maroudas, A., Wachtel, E., Grushko, G., Katz, E. P., and Weinberg, P. (1991) *Biochim Biophys Acta* 1073, 285–94; Grushko, G., Schneiderman, R., and Maroudas, A. (1989) *Connective Tissue Research* 19, 149–176.

The shape of the equilibrium Pc-W/W$_i$ curve reveals several remarkable properties of the collagen network. First, the Pc-W/W$_i$ curve is highly non-linear and monotonically increasing in the regime in which the network is in tension— In the "inflated" state, the slope of Pc vs W/W$_i$ progressively increases. The network necessarily has a non-zero resting value of W/W$_i$—at which point the collagen network becomes "limp" or buckles.

Conversely, the equilibrium $\pi_{PG}$-W/W$_i$ curve is non-linear and monotonically decreasing. It shows that increasing tissue water content while keeping PG content fixed necessarily reduces PG osmotic pressure.

The shape of the $\pi_{PEG}$-W/W$_i$ curve represents the equilibrium response of the whole tissue (PG+collagen network) in response to the applied isotropic osmotic stress.

While for a single cartilage plug, it is illuminating to examine properties of the collagen network and PGs as a function of normalized tissue weight, it is difficult to use normalized tissue weight to make meaningful comparisons of tissue properties among different cartilage specimens. Therefore, in subsequent figures, we choose to plot Pc, $\pi_{PG}$ and other quantities of interest against tissue hydration, (Vt−Vc)/Vc, as defined in Equation (6a).

Figure 15:
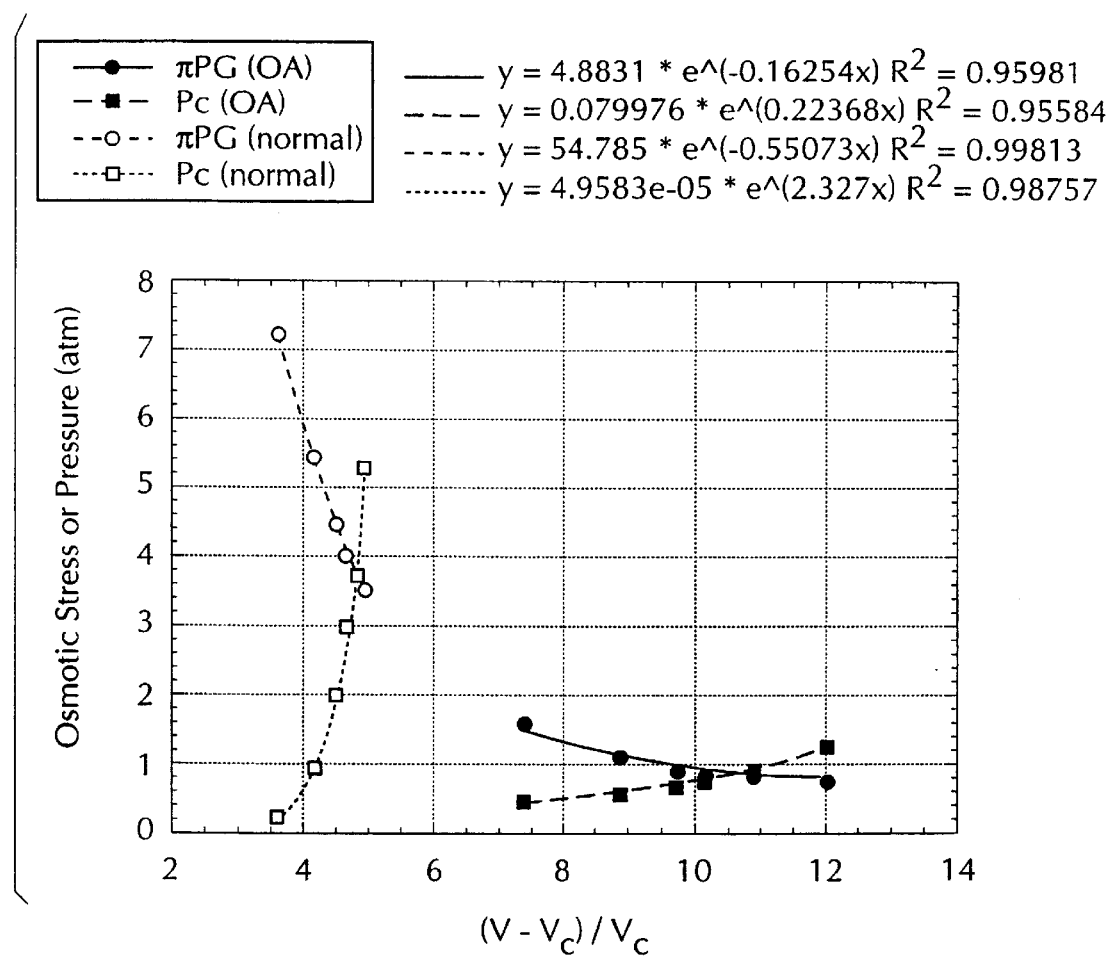
FIG. 15 shows a comparison of plots of Pc and $\pi_{PG}$ vs (Vt−Vc)/Vc for a normal 55 year old, shown in FIG. 14, and an OA specimen.

FIG. 15 shows a comparison of plots of Pc and $\pi_{PG}$ vs (Vt−Vc)/Vc for a normal 55 year old and an OA specimen. For the normal specimen, equilibrium in the absence of osmotic loading occurs at a low hydration, (Vt−Vc)/Vc=4.87, whereas for the OA specimen, equilibrium in the absence of loading occurs at the high hydration, (Vt−Vc)/Vc=10.92, which represents more than a two-fold increase in the ratio of total tissue water per dry weight in the OA specimen (see the Table of FIG. 11). In considering the relative equilibrium stiffness of unloaded normal and OA cartilage, it is useful to compute the differences in the slopes between Pc vs (Vt−Vc)/Vc and $\pi_{PG}$ vs (Vt−Vc)/Vc. For the normal specimen, this difference is 11.6 atm per percentage change in hydration, whereas for the OA specimen this difference is 0.34 atm per percentage change in hydration. Another observation relating to tissue stiffness is the relative response of tissue hydration to a change in the ionic strength of the surrounding medium: In the normal tissue specimen, a change of 1 atm in $\pi_{PG}$ produces a change in volume of approximately 1.8% whereas in the OA tissue specimen, a smaller change in 7$\pi_{PG}$ (0.5 atm) produces a larger change in tissue volume of 10%. While we have obtained data from only one OA joint in the present study, these results are qualitatively consistent our previous findings on hydration and swelling based on a large number of studies of OA cartilage. See, e.g., Maroudas, A. and Venn, M. (1977) *Ann Rheum Dis* 36, 399–406; Maroudas, A. (1976) *Nature* 260, 808–9; Grushko, G., Schneiderman, R., and Maroudas, A. (1989) *Connective Tissue Research* 19, 149–176; and Maroudas, A., Ziv, I., Weisman, N., and, Venn, M. (1985) *Biorheology* 22, 159–69.

Figure 16:
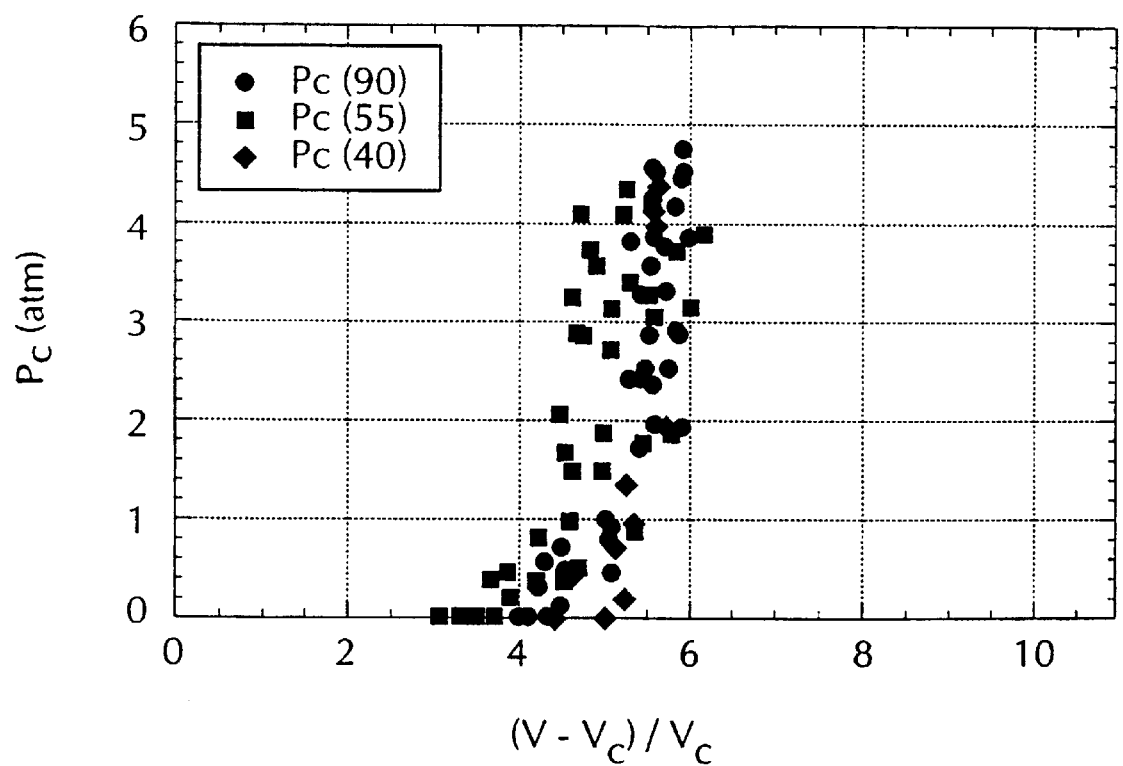
FIG. 16 shows curves of equilibrium collagen network restraining pressure vs. collagen network hydration, Pc vs (Vt−Vc)/Vc, measured in normal human cartilage specimens of ages 40, 55, and 90.

FIG. 16 shows curves of Pc vs (Vt−Vc)/Vc measured in normal cartilage specimens of different ages. The results for two to seven specimens from each joint are included in the figure. While the curves represent tissues from widely differing age groups, they are qualitatively similar, both in shape and extent. The Table of FIG. 11 shows a statistically significant trend toward an increased equilibrium value of Pc with age consistent with previous findings. See, Grushko, G., Schneiderman, R., and Maroudas, A. (1989) *Connective Tissue Research* 19, 149–176; and Grushko, G. (1987) Age-related variations in some physical and chemical properties of articular cartilage, Master's Thesis, Technion, Haifa, 138.

FIG. 16 shows that the collagen network does not become "limp" until approximately 25% of the initial tissue water has been expressed. Therefore, the hydration values over which the collagen network contribution cannot be ignored in the balance of forces, (i.e, that Pc>0), is significantly larger than was previously thought. See, e.g., Maroudas, A. and Bannon, C. (1981) *Biorheology* 18, 619–32; and Schneiderman, R., and Grushko, G. (1992) in Mechanics of Swelling: Swelling Pressure of Cartilage: Roles Played by Proteoglycans and Collagen (Karalis, T. K., Eds.), pp. Springer-Verlag, Berlin.

Figure 17:
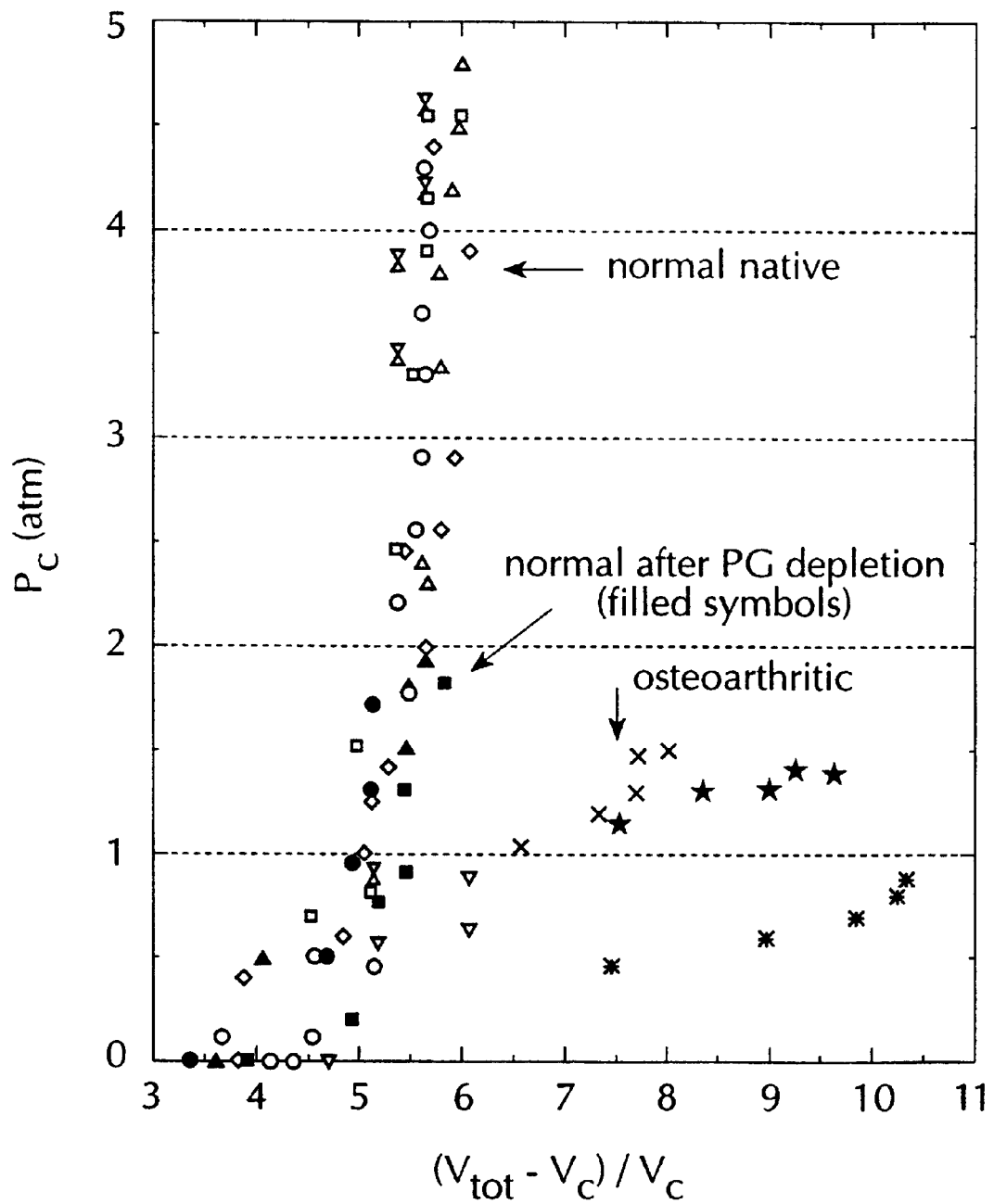
FIG. 17 shows Pc vs (Vt−Vc)/Vc curves for 1) a normal specimen (90 years), 2) a specimen from the same 90 year old normal joint but treated with trypsin, and 3) an OA specimen.

FIG. 17 shows Pc vs (Vt−Vc)/Vc curves for 1) a normal specimen (90 years), 2) a specimen from the same 90 year old normal joint but treated with trypsin, and 3) an OA specimen. The mild trypsin treatment was aimed at reducing the GAG content to the level found in some of the OA specimens, while not affecting the collagen network. This treatment lowered the FCD by approximately 30–40% and decreased tissue volume by approximately 5%. The treated and untreated normal specimens show a similar dependence of Pc on hydration: however, owing to the reduction in the PG content of the treated specimens, the hydration ranges over which the stress titration is performed begins at a lower value than in the untreated specimens. Where the hydration levels of the treated and untreated normal specimens do coincide, so do the values of Pc. The similarity in the Pc vs (Vt–Vc)/Vc curves of the treated and untreated specimens, differing widely in FCD, shows that neither the FCD, nor the GAG content per se influences the stiffness of the collagen network. In addition, since FCD is known to affect the intrafibrillar water content, it appears that differences in the latter also do not influence the Pc vs (Vt–Vc)/Vc curve.

In contrast to the normal specimens, Pc vs (Vt–Vc)/Vc curves for OA specimens in FIG. 17 show a marked reduction in slope and a rightward shift to higher hydrations. The OA specimen corresponding to the curve with the shallowest slope has an FCD per dry weight similar to that found in normal native samples (see the Table of FIG. 11). The OA specimen from a neighboring region on the joint, corresponding to the curve with a steeper slope, has a lower FCD per dry weight, similar to that of the samples that have been trypsin treated. There is thus no relation between the shape of the Pc vs (Vt–Vc)/Vc curve and the GAG-to-collagen ratio in the tissue. However, in a related preliminary study, aimed at determining the fraction of denatured collagen in normal and osteoarthritic cartilage, it was found that the same specimen showing the lowest slope of the Pc vs (Vt–Vc)/Vc curve contained the highest proportion of denatured collagen among a group of OA specimens. See, Bank, R., Krikken, M., Lafeber, F., and Te Koppele, J., (1996) in 42nd Annual Meeting of the ORS, Atlanta, 750. Our OA data do not extend to a sufficiently low level of hydration to show the collagen network behavior in this regime, so is difficult to ascertain at what hydration Pc reaches zero, but there is an indication that $\pi_{PG}$ and thus Pc are overestimated in the OA specimens.

The Table of FIG. 11 shows equilibrium parameters characterizing the composition and state of the tissue.

Discussion

In accordance with the present invention, we have developed a straightforward experimental methodology and a simple mathematical model for the determination of Pc, but it is essential to bear in mind that these experiments require considerable experience and care in handling the tissue specimens, especially in weighing them, as described in Methods.

Another cautionary reminder concerns calculating Pc by taking the difference of $\pi_{PG}$ and $\pi_{PEG}$ when these differences are small. It should be noted that pooled averaged data are used to calculate $\pi_{PG}$, in which small differences in KS/CS ratios were not taken into account. However, the age ranges of the cartilage used in the present study, and in the study in which the osmotic pressure of the isolated PGs was measured (ages 50–80), overlap to a large extent. (Variability in the middle zone in the CS-to-KS ratio in this age range does not exceed 20%).

In addition, for normal specimens, we have a reassuring indication that our calculated values of $\pi_{PG}$ are accurate, since, in the low hydration regime—where collagen tension should be close to zero—we find that the difference, $\pi_{PG}-\pi_{PEG}$, approaches zero as expected. This makes us feel more confident about the accuracy of our calculated values of Pc at higher hydrations, where collagen is in tension.

In the case of the OA specimens: we have at present no information about the specific characteristics of their $\pi_{PG}$ vs FCD curves, so we had to use PG data from normal tissue. However, we do know that KS/CS decreases in OA which should lead to a lowering of $\pi_{PG}$ for a given level of FCD as compared with PG from normal cartilage. See, Venn, M. and Maroudas, A. (1977) Ann Rheum Dis 36, 121–9; Mankin, H. J. and Lippiello, L. (1971) Journal of Clinical Investigation 50, 1712; and Erlich, S. (1994) The influence of age and degeneration on changes in the osmotic pressure of the proteoglycans in the intervertral disc, Master's Thesis, Department of Biomedical Engineering, Technion, Haifa, Israel, 66; and Urban, J. P., Maroudas, A., Bayliss, M. T., and Dillon, J. (1979) Biorheology 16, 447–64. As a result, we may be overestimating $\pi_{PG}$ in OA specimens.

One of our goals for refining this methodology is to use PG extracted from each joint rather than PG extracted from many specimens. The availability of such data would improve the accuracy of the relationship between PG composition and osmotic pressure.

Physiological Implications

Our experimental results show that for normal unloaded cartilage at physiological ionic strength, the slope of Pc vs (Vt–Vc)/Vc is significantly steeper than that of $\pi_{PG}$ vs (Vt–Vc)/Vc at their point of intersection. Thus, the collagen network effectively fixes or "clamps" the equilibrium hydration to lie within a very narrow range despite large changes in PG osmotic pressure. This result helps us understand three important phenomena: First, it explains why excised normal cartilage plugs immersed in 0.15 NaCl show little initial swelling although the osmotic pressure gradients are altered as a result of removal from the intact joint. See, Maroudas, A. (1976) Nature 260, 808–9. Second, we can similarly see why normal human cartilage swells by only 1%–2% when it is transferred from physiological saline into hypotonic solution. See, Maroudas, A., Ziv, I., Weisman, N., and Venn, M. (1985) Biorheology 22, 159–69. Third, the stiffness of the collagen network ensures that in vivo, normal human cartilage maintains dimensional stability when small changes in proteoglycan content occur (such as in normal turnover); and conversely, it follows that if collagen stiffness is decreased (as in OA), the same variations in PG osmotic pressure cause the cartilage to swell or shrink by a larger amount.

Moreover, it is important to note that the shape of the Pc vs (Vt–Vc)/Vc curve largely determines the PG concentration at equilibrium by controlling the volume of the hydrated tissue—and not vice versa: In normal specimens, high PG concentration, high FCD, and high $\pi_{PG}$ can be developed owing to high collagen network stiffness. This means that during load-bearing, because of the high GAG osmotic pressure, changes in tissue thickness and chondrocyte volume will remain relatively small.

On the other hand, in OA specimens, for the same FCD per dry weight, (Vt–Vc)/Vc at equilibrium is approximately twice as high as in normal specimens, and the equilibrium FCD (proteoglycan concentration), and hence $FCD_{eff}$ are halved (see FIG. 11). As a result, OA tissue cannot develop a high PG concentration: Even if PG quantity (i.e., the ratio of PG-to-dry collagen) were to increase, the tissue would simply imbibe more water, and swell to a larger volume, without increasing PG concentration significantly. Hence, load bearing capacity of the tissue would not increase.

The trypsin treatment, which reduced the FCD per dry weight (see FIG. 11) to the lowest level found among our OA specimens, did not result in any discernible change in Pc vs (Vt–Vc)/Vc at equilibrium. Hence there was no increase in hydration, and therefore, the $FCD_{eff}$ was considerably higher than in the OA specimens at equilibrium (see the Table of FIG. 11).

In this experiment, carried out in accordance with the present invention, we have confined a previous finding that the equilibrium values of Pc=$\pi_{PG}$ increase with age. See, Grushko, G., Schneiderman, R., and Maroudas, A. (1989) *Connective Tissue Research* 19, 149–176; and Grushko, G. (1987) Age-related variations in some physical and chemical properties of articular cartilage, Master's Thesis, Technion, Haifa, 138. This increase is likely due to an increase in the slope of Pc vs (Vt–Vc)/Vc with age, however, more data are required to assess adequately these trends and other characteristics of the collagen network with age.

Conversely, while a stiff collagen network is essential to the adequate function of cartilage, excessive rigidity of the collagen network could render it brittle and hence more prone to failure from long-term fatigue. Now that we can measure Pc vs (Vt–Vc)/Vc quantitatively, it is also possible to measure the level of stiffness in cartilage (or of synthetic cartilage substitutes), and relate it to the quality of load bearing and fatigue resistance.

So far, we have discussed some physiological consequences of the stiffness of the collagen network in human articular cartilage. However, this work also raises crucial biochemical and structural questions which, for the time being, must be left unanswered: What specific molecular and ultrastructural factors give rise to human articular cartilage's singularly high resistance to swelling? See, Maroudas, A. and Venn, M. (1977) *Ann Rheum Dis* 36, 399–406; Maroudas, A. (1976) *Nature* 260, 808–9; and Maroudas, A. and Venn, M. (1977) *Ann Rheum Dis* 36, 399–406. Also, how do these factors change during development, aging, and degeneration? We know that the "backbone" of the network consists of fibrillar assemblies of collagen II, with some collagen XI. See, Mankin, H. J. and Lippiello, L. (1971) *Journal of Clinical Investigation* 50, 1712; and Mendler, M., Eich-Bender, S. G., Vaughan, L., Winterhalter, K. H., and Bruckner, P. (1989) *J. Cell. Biol.* 108, 191–197. These molecules undergo post-translational changes with age, such as inter-molecular cross-links involving lysine and hydroxylysine residues and cross-links of the pentosidine type brought about by non-enzymatic glycation. See, Eyre, D., Wu, J. J., and Woods, P. (1992) in Articular Cartilage in Osteoarthritis: Cartilage-specific collagens: Structural studies (Kuettner, K. E., Schleyerbach, R., Peyron, J. G., and Hascall, V. C., Eds.), pp. Raven Press, New York. These assemblies contain, in addition, a number of other molecular constituents such as collagen IX, decorin and fibromodulin. See, Takahashi, M., Hoshino, H., Kushida, K., and Inoue, T. (1995) *Ann. Biochem.* 232, 158–162. Some of these molecules are bound to the surface of the fibrils, as putative non-covalent supra-molecular cross-bridges. See, Mendler, M., Eich-Bender, S. G., Vaughan, L., Winterhalter, K. H., and Bruckner, P. (1989) *J. Cell. Biol.* 108, 191–197; Takahashi, M., Hoshino, H., Kushida, K., and Inoue, T. (1995) *Ann. Biochem.* 232, 158–162. Some of their side-chain substituents that may be involved in collagen cross-liking, may change with age. See, Hedbom, E. and Heinegard, D. (1993) *J. Biol. Chem.* 268, 27307–27312. Ultimately, we would like to know what role these various constitutuents (and their interactions) play in determining the mechanical properties of the collagen network that we are now in a position to measure.

Another biological question worthy of further study is how the various enzymes affect the molecular organization and structure of the collagen network, and its gross mechanical properties? Since it is also possible by external treatment with specific enzymes or to modify specific network constituents by activating proteases, it is worthwhile to try to understand the mechanical consequences to the collagen network by these manipulations. We hope that our quantitative methodology will provide an effective tool for assessing the physiological implication of specific molecular changes of the above type, particularly in relation to the actual load-bearing function of the tissue.

Cartilage is not a Polyelectrolyte Gel

Because Pc vs (Vt–Vc)/Vc and $\pi_{PG}$ vs (Vt–Vc)/Vc are both monotonic functions of (Vt–Vc)/Vc, the equilibrium state of cartilage is a mechanically stable one—the tissue always returns to the equilibrium state after a departure from it. This property is crucial in order for cartilage to maintain its dimensional stability. Cartilage (as well as some man-made analogs such as an inflated tire) would be poorly adapted for load bearing if they could assume a multiplicity of equilibrium volumes when subjected to a static load, which is the case for many non-electrolyte and polyelectrolyte gels. The latter can assume a multiplicity of equilibrium network volumes under the same thermodynamic equilibrium conditions. One fundamental difference between the architecture of cartilage and simple cross-linked polyelectrolyte gels is that in cartilage, the PG constituents that produce the osmotic pressure and the collagen network that resists it are largely independent (compare response of normal and normal trypsin-treated specimens in FIG. 17), whereas in polyelectrolyte and polyelectrolyte gels, they are chemically cross-linked. By separating the polyelectrolytes and elastic network phases, Nature may have precluded the possibility that cartilage exhibits possibly deleterious phase transitions. See, Tanaka, T. and Fillmore, D. J. (1978) *J. Chem. Phys.* 70, 1214–1218.

Distinguishing Cartilage Matrix and Collagen Network Properties

It is important to contrast the behavior of the cartilage matrix and the collagen network under equilibrium isotropic loading. FIG. 14 shows the measured equilibrium curves Pc, $\pi_{PG}$, and $\pi_{PEG}$ vs W/$W_i$ for a normal cartilage specimen. $\pi_{PEG}$ vs W/$W_i$ represents the (isotropic) osmotic stress one would apply to deswell the tissue, whereas Pc vs W/$W_i$ represents the restraining pressure produced by the collagen network in tension at each W/$W_i$ in response to the applied load, and the PG swelling pressure. Additionally, though the relationship between $\pi_{PEG}$ VS W/$W_i$ is approximately linear for small tissue deformation about the unloaded equilibrium, this "aggregate" curve results from the balance of two highly non-linear stresses, the swelling stress of the PGs and the restraining stress exerted by the collagen network, neither of which is zero when the tissue is in an "unloaded" state.

Cartilage is not a Rock or a Soil

This distinction between the behavior of the aggregate tissue and its individual constituents, e.g., displayed in FIG. 14, shed light on existing biomechanical models of cartilage. Following McCutchen's seminal suggestion that when loaded, cartilage deforms by expressing or squeezing out water like a sponge or a soil, subsequent biomechanical models have treated cartilage literally as a soil, consisting of a "pore fluid" phase and a single "elastic network" phase. See, McCutchen, C. W. (1962) *Wear* 5, 1–17 Tanaka, T. and Fillmore, D. J. (1978) *J. Chem. Phys.* 70, 1214–1218. Moreover, they have characterized the material properties of the cartilage matrix by using a constitutive law that is identical in form to one used to describe settlement or consolidation of rocks and soils. See, Mow, V. C., Kuei, S.

C., Lai, W. M., and Armstrong, C. G. (1980) *J. Biomech. Engng.* 102, 73–84. As our present study demonstrates, to understand the equilibrium swelling behavior of cartilage (and other extracellular matrices) requires separating its "solid" matrix phase into at least two constituents: the PGs that exert an osmotic pressure, and the collagen network that restrains them. The PG and collagen components of cartilage are structurally and compositionally distinct, they possess distinct physicochemical properties, and perform distinct physiological functions. Their aggregation into a single "solid-like" phase can obscure these differences. A biologically sensible constitutive law of the cartilage matrix should express its total stress tensor as a sum of (at least) collagen network and PG stress tensors, however, this decomposition is not possible with previously proposed constitutive laws of the cartilage matrix.

Implications for the Unsteady State

Our findings have significant consequences for non-equilibrium loading regimes, paricularly since the collagen network acts to restrain the PGs over a relatively wide range of hydrations. For example, in static loading, both in confined and unconfined compression, initially, the driving pressure will be underestimated over the range in which the collagen network is in tension when using the D'Arcy equation as it is presently applied See, e.g., Maroudas, A. and Bannon, C. (1981) *Biorheology* 18, 619–32. In cyclic loading, both for small and large deformations, the non-linear collagen network contributions will be significant, both in compression and in recovery, particularly at small strains. These contributions are expected to be particularly relevant to load-bearing during locomotion, and will be affected by subsequent modifications in the collagen network associated with OA. The underestimation of the driving pressure also has significant implications to the dynamics of joint lubrication.

EXAMPLE 2

Around the intersection points of the $Pc^{eq}$ vs $V^{eq}$ and $\pi_{PG}$ vs $V^{eq}$ curves—the unloaded equilibrium state—we expand these functions $Pc^{eq}(V^{eq})$ and $\pi_{PG}(V^{eq})$ as a Taylor series in $V^{eq}$ to estimate the new equilibrium values of $Pc_{eq}(V'^{eq})$ and $\pi_{PG}(V'^{eq})$ in a new equilibrium state at $V'^{eq}$ in which the tissue is loaded by an infinitesimal isotropic stress, $\delta P_{PEG}$. First we expand the restraining pressure as a function of V:

$$P_c'^{eq} = P_c^{eq}(V'^{eq}) \approx P_c^{eq} + \frac{dP_c}{dV}\bigg|_{V^{eq}}(V'^{eq} - V^{eq}) \qquad \text{A.Ia}$$

and then we expand the PG osmotic pressure as a function of V:

$$\pi_{PG}'^{eq} = \pi_{PG}(V'^{eq}) \approx \pi_{PG}^{eq} + \frac{d\pi_{PG}}{dV}\bigg|_{V^{eq}}(V'^{eq} - V^{eq}) \qquad \text{A.Ib}$$

In the unloaded equilibrium state, we know that $$Pc^{eq} = \pi_{PG}^{eq}(V^{eq}), \qquad \text{A.II}$$

so that taking the difference of Eqs. A.Ib and A.Ia, and regrouping terms we obtain $$\pi_{PG}'^{eq} - P_c'^{eq} \approx \left[\frac{d\pi_{PG}}{dV}\bigg|_{V^{eq}} - \frac{dP_c}{dV}\bigg|_{V^{eq}}\right][V'^{eq} - V^{eq}] \qquad \text{A.III}$$

When the difference between the PG osmotic pressure and collagen network stress is caused by the application of a small osmotic stress, $\delta P_{PEG}$, Eq. 1b tells us that $$\pi_{PG}'^{eq} - P_c'^{eq} = \delta\pi_{PEG} \qquad \text{A.IV}$$

Then, substituting Eq. A.IV into A.III we obtain which is the equation given in Eq. (7) above.

$$\delta\pi_{PEG} \approx \left[\frac{d\pi_{PG}}{dV}\bigg|_{V^{eq}} - \frac{dP_c}{dV}\bigg|_{V^{eq}}\right][V'^{eq} - V^{eq}] \qquad \text{A.V}$$

To obtain an expression for the fractional change in applied isotropic stress divided by the fractional change in volume, simply divide Eq. A.V by $(V'^{eq} - V^{eq})/V^{eq}$ to obtain Eq. (13).

EXAMPLE 3

More than a quarter of a century has passed since Ogston (1) originally proposed the idea that in connective tissues, the collagen network resists the osmotic swelling pressure exerted by proteoglycans (PG):

"So we may arrive at a model of connective tissue, as consisting of a relatively coarse fibrous network capable of resisting tension (internal or external), but not compression, filled with a much finer, molecular network of polysaccharide fibres trapped within it."

Ogston also wrote that the high concentration of polysaccharides in cartilage must produce a high swelling pressure that keeps cartilage "inflated" (1).

At the same time, Maroudas found that early in osteoarthritis (OA), cartilage hydration increased despite a decrease in the concentration of glycosaminoglycans, the main hydrophilic component of connective tissues (2–4). Various explanations were advanced to resolve this apparent paradox, e.g., an increase in "bound collagen water" (5) and the increased osmotic pressure due to the "depolymerization" of the mucopolysaccharides (4). Maroudas carried out experiments disproving these various hypotheses, and proposed an explanation based on the Ogston "balance of forces" concept that the difference in water content between normal and OA cartilage is due to an impairment of the collagen network in OA. The decreased "elastic restraint" of the collagen network "allows the tissue to achieve a higher hydration in spite of the relatively low osmotic pressure of its decreased GAG content" (6).

It was also found that normal cartilage hardly swells when immersed in hypotonic solutions, despite a substantial increase in the osmotic stress (6, 7), suggesting that its collagen network is stiff when "inflated". However, osteoarthritic cartilage swells considerably more under these conditions, supporting the notion that its collagen network is more flaccid than that of normal tissue (6, 7): Maroudas (6, 7) suggested that swelling in hypotonic solution is a sensitive measure of matrix damage, and can therefore be used as a test for the latter, a suggestion that is increasingly being taken up by other cartilage researchers (8, 9)(10).

In spite of the fact that this qualitative information has been available for a long time, there has been no quantitative methodology to determine the mechanical integrity of the collagen network in cartilage. One measure of its integrity is the ability of the network to develop a hydrostatic stress in response to the proteoglycan swelling pressure. The purpose of this work is to propose a new methodology to measure this hydrostatic pressure, Pc, (caused by tensile stresses developed within the collagen network) as a function of tissue hydration.

The data that we can obtain using this approach are potentially significant in relation to understanding the etiology of osteoarthritis. In addition, a measure of collagen network integrity may throw light on the changes in cartilage that occur in normal development, aging, and degeneration, as well as to help quantify intrinsic differences between species, between different joints, or different locations on the same joint. There is also a need to quantify how applied loads affect the state of the collagen network, during locomotion, in experimental studies, or during a clinical evaluation. Finally, it is increasingly important to identify methods to evaluate collagen network integrity in tissue-engineered cartilage specimens.

In this present pilot study, we have used our new methodology to measure Pc as a function of hydration in some normal human cartilage specimens, in normal specimens following treatment with trypsin, and in specimens from an osteoarthritic joint.

Experimental Design

The physiological role of the collagen network is to resist swelling or stretching of the tissue. Our primary experimental tool to characterize this behavior employs an equilibrium osmotic stress titration technique in which tissue specimens are exposed to a range of known osmotic stress by using calibrated solutions of osmotically active polyethylene glycol (PEG). Curves of equilibrium collagen network pressure vs. hydration are obtie by allowing cartilage specimens to come to mechano-chemical equilibrium at eah different level of osmotic stress, that result in different degrees of collagen network hydration.

When there is no externally applied stress, cartilage matrix hydration is governed by a balance between the osmotic pressure due to the PGs, $\pi_{PG}$ (that acts to imbibe fluid), and the restraining pressure exerted by the collagen network in tension, P. (that acts to express fluid from the tissue) (7):

$$P_c = \pi_{PG} \quad (1)$$

However, when there is an externally applied isotropic stress, mechano-chemical equilibrium is achieved when $P_c$ exerted by the collagen network and the applied stress (both of which now act to express fluid) are balanced by the osmotic pressure of the PGs. When the applied stress results from the osmotic pressure of a PEG solution, $\pi_{PEG}$, then $$P_c + \pi_{PEG} = \pi_{PG} \text{ or } P_c = \pi_{PG} - \pi_{PEG} \quad (2)$$

$\pi_{PG}$ in the tissue can be determined from independent measurements of $\pi_{PG}$ vs PG concentration (or fixed-charge density, FCD) obtained using solutions of PGs extracted from cartilage. To infer $\pi_{PG}$ in cartilage from these data, the calculation of PG concentration must be based on the volume of fluid outside the collagen fibrils to which the PGs are confined. (FIG. 7 illustrates the two-compartment model of the cartilage matrix structure). We also need to know both the total water content of the tissue, and the water content within the fibrils. The former is determined from the difference between wet and dry tissue weights. The latter can be determined from collagen spacing measurements obtained by x-ray diffraction (11). However, intrafibrillar water content of the collagen fibers is not constant, but depends upon the osmotic stress acting on them (11).

The stress to which the collagen network is subjected in situ is augmented or diminished by changing the ionic strength of the interstitial fluid (thus changing the osmotic pressure exerted by the PG) or by changing the concentration of the osmotically active PEG in the external bath (thus altering the osmotic stress acting on the tissue sample across a dialysis membrane).

Since one of our aims is to compare different cartilage samples (e.g., healthy vs. diseased, old vs. young, etc.) whose composition may vary, we need to devise objective ways to compare them. Since the rate of turnover of collagen in cartilage is known to be extremely low (12, 13) and therefore, its quantity in a given joint remains relatively constant throughout adult life, we normalize mass in relation to collagen dry mass, and normalize volume in relation to collagen dry volume.

Tissue Sources

Femoral heads (ages 40, 55, and 90 years) were obtained at operations for femoral neck fractures or at post monem. Two femoral condyles were obtained at an operation for total joint replacement. Joints were immediately placed in plastic bags, sealed, and then kept frozen at −20° C. Before handling, joints were soaked in physiological saline at 4° C. for one to two hours. This freezing and thawing protocol has been shown to preserve structural and mechanical properties of the tissue (14).

Mild enzymatic treatment of the cartilage specimens is performed by incubating them in 1 mg trypsin solution (1:250) per ml 0.15M NaCl for approximately five hours at room temperature, with subsequent washings in 0.15M NaCl containing enzyme inhibitors. This mild treatment results in partial removal of the PG, and a concomitant decrease of FCD of approximately 40% (present data). Treatments with trypsin carried out for longer periods of time and at higher temperatures, though they removed almost all the PG, were shown not to affect collagen fibril structure, composition, or uniaxial tension response of the tissue (11, 15–17).

Specimen Preparation

Full-depth cartilage plugs, approximately 7 mm in diameter, were cored from the superior surface of the normal femoral head. The cartilage showed no sign of fibrillation as assessed by the methods of Byers et al. (18) and Indian ink staining (19). Similar plugs were obtained from osteoarthritic (OA) knees, the surfaces of which were carefully characterized by the same procedures as above. In the case of OA specimens, the surface appearance ranged from nearly intact to severely fibrillated (20). Plugs were sliced on a freezing microtome (Lzitz), and approximately 1 mm thick sections from the "middle" zone were used in the present series of experiments. Slices from the middle zone were used because in normal cartilage, the PG contents and fixed-charge densities are known to be relatively uniform in this region (2, 6, 21). We weighed the sections as cut, and then soaked them in 0.15M NaCl (physiological saline) overnight, and again measured their equilibrium weight.

Materials

Polyethylene glycol (PEG) 20,000 DA was obtained from Fluka (Switzerland), and purified by ultrafiltration through a 3,000 DA membrane. Trypsin and proteinase inhibitors were obtained from Sigma Chemicals (St. Louis). Radioactively labeled $Na^{+22}$ as obtained from-Amersham International (UK). Spectrapor dialysis tubing (MWCO 1,000 DA) was obtained from Spectrum Medical (CA).

METHODS

Both tissue swelling pressure and the osmotic pressure of the proteoglycan solutions were measured by equilibrium dialysis against calibrated PEG solutions.

Calibration of PEG Solutions

FIG. 8 shows calibration curves of PEG osmotic pressure vs. PEG concentration at 4° C., obtained from measurements in our laboratory (22, 23) as well as published data of Parsegian with which our data show good agreement (22). The apparatus used for measuring the osmotic pressure of PEG consisted of a specially adapted stirred ultrafiltration cell fitted with a semi-permeable membrane. The solution osmotic pressure was balanced by applied Nitrogen pressure. The cell was capable of withstanding applied pressures of up to 5 atm. The apparatus and the procedure are described in more detail elsewhere (24, 26).

Equilibrium Dialysis of Cartilage Specimens Against PEG Solutions

For compressing cartilage specimens, PEG solutions were prepared in 0.15M and 0.015M NaCl, ranging from 3 gm PEG in 100 gm solvent ($\pi_{PEG} \approx 0.1$ atm) to 27.5 gm PEG in 100 gm solvent ($\pi_{PEG} \approx 10$ atm). The $\pi_{PEG}$ vs. PEG concentration datain 0.015 M and in 0.15 M NaCl were found to coincide (authors' unpublished data).

Since PEG has been found to penetrate cartilage, the tissue samples were not placed directly in the PEG solution, but were separated from it by dialysis tubing (Spectrapor 1,000 MWCO), which minimizes PEG penetration although does not entirely eliminate it (27). Control experiments were performed (showing that differences between dry tissue weight determined before and after dialysis against PEG were negligible), to ensure that under our experimental conditions, there was no significant PEG penetration.

Cartilage slices were equilibrated in each solution for approximately 48 hours at 4° C. as this has been found to be sufficient to achieve mechano-chemical equilibrium, while at the same time minimizes PEG penetration. At the end of each test, slices were removed from the dialysis tubing and weighed immediately. They were then reequilibrated in 0.15M NaCl and reweighed to ensure that they returned to their baseline weight. At this stage, the slices were ready for reequilibration in another PEG solution. In this way, curvs of swelling pressure versus cartilage weight were obtained in a manner described below. Note that all weighings were carried out as previously described (28). Tissue samples, placed in pre-weighed stoppered vials, were weighed using an analytical balance to five decimal places. Reproducibility was between 0.2–0.3%. All solutions contained 0.01% (wt./vol.) $NaN_3$. We periodically weighed the specimens in 0.15M NaCl to ensure that there were no significant changes in tissue weight during the experiment, and periodically measured FCD to ensure that no PG was lost. We discarded samples from the study that exhibited significant changes in weight and/or FCD.

To obtain dry weights, the specimens were dried until reaching a constant weight in a freeze drier. This usually took 24 to 36 hours, depending on the initial tissue weight. The specimens were weighed in stoppered vials that had been pre-weighed. Sometimes the samples were freeze-dried several times during a series of experiments (e.g., to check for PEG penetration) and subsequently rehydrated. This treatment was found not to alter any of the tissue properties that we were testing.

The experimental procedure is straightforward but success depends on extremely careful, accurate and reproducible weight determinations, both wet and dry. For wet weight it is essential—before one weighs the sample—to blot both surfaces to remove all extraneous liquid; blot gently so as not to express the interstitial fluid, yet swiftly so as not to allow loss of water through evaporation.

FCD Determination

Measurements of cartilage's total fixed-charge (mEq per gm total tissue) were obtained by means of the Tracer Cation Method using $Na^{+22}$ in hypotonic saline (0.015M NaCl) (29).

Osmotic Pressure of PG Solutions

In the present study, we have not carried out these experiments, but have used previous experimental results: Data of Urban et al. (30) for $\pi_{PG}$ vs FCD in PG solutions, which have been recently recalculated (Osmotic pressures of PG solutions were obtained by using equilibrium dialysis against PEG solutions. Urban et al. (30) calculated the osmotic pressures of these PEG solutions using virial coefficients reported for 25° C. by Edmond and Ogston (31) who assumed that the virial coefficients did not vary with temperature. Subsequently, direct measurements of PEG osmotic pressure at lower temperatures were performed by Parsegian et al. (25), and independently in our laboratory (24, 26). The assumption of constant virial coefficients was shown to be incorrect. We recalculated the data of Urban et al. (27) using new experimental calibrations of PEG solutions. PG osmotic pressures were obtained by dialysis against PEG solutions of known concentrations), and new experimental data (22, 23) were combined, and then fit with a quadratic function:

$$\pi_{PG} = M0 + M1*FCD + M2*FCD^2 \quad (3)$$

by using non-linear regression to obtain the virial coefficients: M0, M1, and M2. The data set and the fitted quadratic function are shown in FIG. 9. Note that this empirical relationship includes both electrostatic and entropic contributions.

Collagen Analysis

Cartilage samples were hydrolyzed in 6M HCl at 110° C. for 20–24 hours, dried overnight in a Speed Vac (Savant, Farmingdale), and dissolved in 0.1 M sodium borate buffer (pH 8.0). A 200 mL aliquot containing 0.76 mg tissue (dry weight) was derivatized with 200 mL 6mM g-fluorenylmethyl chloroformate (Fluka, Switzerland) in acetone for 5 min. at room temperature. Termination of the reaction was performed by extraction with pentane. Amino acid analysis was performed according to Miller et al. (32). The amount of collagen (in mg) was determined by the amount of hydroxyproline, assuming 300 residues per triple helical molecule with a molecular weight of 300,000 DA.

Intrafibrillar Water Deternidnation

It was shown by Katz et al. (33) and Maroudas et al. (11) that collagen fibril hydration is not constant (defined as the mass of intrafibrillar water, mIAFO, divided by the mass of dry collagen, $m_c$) is not a constant, but is a function of the external stress acting on the collagen fibrils.

We determined the relationship between intrafibrillar water and extrafibrillar osmotic pressure from previous experimental data. Intrafibrillar water content was calculated from collagen spacing data for human articular cartilage (11, 33, 34) as measured by low-angle equatorial x-ray scattering (33), at varying levels of osmotic stress. Note that the data include both native specimens, in which the osmotic stress is due to the osmotic pressure of the extrafibrillar PGs, and PG-free specimens in which the osmotic stress is provided by PEG.

We fit the intrafibrillar water content to an exponentially decaying function of the osmotic pressure in the extrafibrillar compartment, $\pi_{EF}$, using non-linear regression:

$$\frac{m_{IFH2O}}{m_c} = m1 + m2 * e^{-m3*\pi_{EF}} \qquad (4)$$

Both the data and the fitted function are shown in FIG. 10. The use of an exponentially decaying function in this regime of intermolecular spacing is consistent with recent findings of Leikin et al. (35).

Inferring Pc Vs Collagen Network Hydration

Our analysis is based on several simplifying assumptions. 1) The matrix consists of two compartments, each with uniform composition, material properties, and structure on the scale of the specimen (36). 2) The PG osmotic pressure, 7PG within the tissue is the same as the osmotic pressure of isolated PGs when the PG concentration is expressed on the basis of extrafibrillar water (11, 37)(22). 3) The relationship between xTv and FCD based on pooled data for PG extracted from normal aged adult human femoral heads (age 50–80) (23, 27) applies to all of our specimens. 4) Intrafibrillar water content does not explicitly depend on Pc. 5) The collagen network within the specimen is isotropic and homogeneous. In this pilot study, we have deliberately chosen cartilage specimens from the middle zone, in which the proteoglycan content is substantially uniform (36), and in which the collagen network does not have a well-defined orientation.

Four equations relating $\pi_{PG}$, $m_{EFH2O}$, $m_{IFH2O}$, and $FCD_{eff}$ (where $m_{EFH2O}$ and $m_{IFH2O}$ are the respective masses of the extra- and intrafibrillar water; and $FCD_{eff}$ is the fixed charge density in mEq per gm of extrafibrillar water) have been presented previously (22). Here, they are used with Eq. (2) to solve for $m_{EFH2O}{}^{eq}$, $m_{IFH2O}{}^{eq}$, $\pi_{PG}{}^{eq}$, $FCD_{eff}{}^{eq}$, and $Pc^{eq}$ to characterize the equilibrium state of cartilage in isotropic loading.

To determine $\pi_{PG}$ vs $FCD_{eff}$ in cartilage we use the relationship for extracted proteoglycans (Eq. 3). Using conservation of charge of the PGs (since in our experiments, no charge is lost or gained during tissue compression or swelling), we relate $FCD_{eff}$ to the measured $FCD_{TOTALH2O}$—the fixed charge density in mEq per gm of total water in the unloaded cartilage—according to:

$$FCD_{eff} = FCD_{TOTALH2O}\left[\frac{m_{TOTALH2O}}{m_{EFH2O}}\right] \qquad (5)$$

$$= FCD_{TOTALH2O}\left[\frac{m_{EFH2O}}{m_{EFH2O} + m_{IFH2O}}\right]^{-1}$$

where $m_{EFH2O}$ is the mass of extrafibrillar water, $m_{IFH2O}$ is the mass of intrafibrillar water, and $m_{TOTALH2O}$ is their sum.

An additional relation we apply is the equation of conservation of mass of the tissue constituents. During swelling or compressing cartilage specimens, no PG or collagen mass is gained or lost, tissue mass can only change by expressing or imbibing water. Therefore, $$m_{EFH2O} = M - m_{IFH2O} - m_{dry}, \qquad (6)$$

where M is the total wet tissue mass, and $m_{dry}$ is the total dry tissue mass, both of which we measure.

Once all independent parameters ($\pi_{PEG}$, $FCD_{TOTALH2O}$, $m_c$, $m_{dry}$, and M) have been determined for each specimen (using representative calculations given in the Table of FIG. 11), then the values of the four dependent variables ($m_{EFH2O}$, $m_{IFH2O}$, $\pi_{PG}$, and $FCD_{eff}$) are completely specified at each equilibrium state by four non-linear independent equations, (3), (4), (5) and (6).

These simultaneous equations are solved here by guessing initial equilibrium values and iterating until final equilibrium values of $m_{FH2O}{}^{eq}$, $m_{EFH2O}{}^{eq}$, $\pi_{PG}{}^{eq}$, and $FCD_{eff}{}^{eq}$ are obtained, as illustrated in the Table of FIG. 12. Then, using $\pi_{PEG}$ and $\pi_{PG}{}^{eq}$ in Eq. (2), we calculate $P_c{}^{eq}$.

We define a collagen network hydration parameter, (Vt−Vc)/Vc, that describes the degree of collagen network inflation. In a simple polymer gel, network hydration is usually defined as the volume of the fluid encompassed by the network divided by the volume of the polymer. Since cartilage tissue is a composite medium, this concept must be extended in a meaningful way. To compare different states of deformation of different tissues, we should measure tissue volume in relation to a volume that is assumed to be constant in all of our specimens. Therefore, we define the equilibrium tissue hydration as the ratio of the total tissue volume outside the dry collagen divided by the volume of dry collagen. The quantity (Vt−Vc)/Vc represents the volume of the tissue, less the dry collagen volume divided by the dry collagen volume:

$$\frac{(V_I - V_C)}{V_C} = \frac{m_{TOTALH2O}v_{H2O} + m_{GAG}v_{GAG} + m_P v_P}{m_c v_c} \qquad (8)$$

where $v_{H2O}=1$ cm$^3$/gm, $v_P=0.74$ cm$^3$/gm (38), $v_{GAG}=0.54$ cm$^3$/gm (39), and $v_c=0.74$ cm$^3$/gm (40) are the partial specific volumes of water, non-collageneous protein, glycosaminoglycans, and collagen, respectively. For non-collagenous proteins we have assumed the same density as for collagen (see the Table of FIG. 13).

Most of the experiments were carried out in 0.15 M NaCl. However, to extend the range of Pc to higher hydrations, some specimens were also equilibrated in 0.015 M NaCl. Without PEG, the equilibrium in 0.015 M NaCl is described by:

$$Pc_{(SW)}{}^{(0.015M)} = \pi_{PG(SW)}{}^{(0.015M)} \qquad (9)$$

where $Pc_{(SW)}{}^{(0.015M)}$ and $\pi_{PG(SW)}{}^{(0.015M)}$ represent respectively the collagen tensile stress and PG osmotic pressure in the swollen state in 0.015M NaCl. Clearly, to determine Pc we need to know the corresponding $\pi_{PG}$.

Unfortunately, at present we have no data on the osmotic pressure of extracted PG in hypotonic solutions. Therefore, an indirect procedure was used, which is described in Appendix 1.

RESULTS

When cartilage specimens were excised from the joint, and equilibrated in 0.15M NaCl they swelled by less than 1% (by tissue weight). On the other hand, initial swelling of the OA cartilage specimens in 0.15M NaCl was as high as 7%. Normal specimens transferred from 0.15M NaCl to 0.015M NaCl swelled by 1% to 2%, while OA specimens swelled up to 10%. This agrees with previous findings (6, 7).

FIG. 14 shows the measured equilibrium pressures: Pc, $\pi_{PG}$, and $\pi_{PEG}$ vs. normalized tissue wet weight, $W/W_i$, for a typical normal cartilage specimen. The point of intersection of the Pc and $\pi_{PG}$ curves represents the state of unloaded equilibrium, (i.e., for no applied pressure) where $\pi_{PEG}=0$. This state corresponds to a hydration $W/W_i=1$. Although the tissue is unstrained, the collagen network is in tension—Pc=$\pi_{PG}\approx3.9$ atm. As we increase $\pi_{PEG}$ from 0 atm, Pc decreases and $\pi_{PG}$ increases. Pc approaches 0 atm after a decrease in $W/W_i$ of about 20% (i.e., a decrease in hydration of about 30%). As we increase $\pi_{PEG}$ further, $\pi_{PG}$ is close to $\pi_{PEG}$, and consequently, Pc remains close to zero. The coincidence of $\pi_{PG}$ and $\pi_{PEG}$ vs hydration has been previously observed at low tissue hydrations (11, 37) and is consistent with the Ogston picture of cartilage that its collagen matrix can exert tension to restrain PGs, but not support compression.

The shape of the equilibrium Pc-$W/W_i$ curve reveals several remarkable properties of the collagen network. First, the Pc-$W/W_i$ curve is highly non-linear and monotonically increasing in the regime in which the network is in tension— In the "inflated" state, the slope of Pc vs $W/W_i$ progressively increases. The network necessarily has a non-zero resting value of $W/W_i$—at which point the collagen network becomes "limp" or buckles.

Conversely, the equilibrium $\pi_{PG}$-$W/W_i$ curve is non-linear and monotonically decreasing. It shows that increasing tissue water content while keeping PG content fixed necessarily reduces PG osmotic pressure.

The shape of the $\pi_{PEG}\pi W/W_i$ curve represents the equilibrium response of the whole tissue (PG+collagen network) in response to the applied isotropic osmotic stress.

While for a single cartilage plug, it is illuminating to examine properties of the collagen network and PGs as a function of normalized tissue weight, it is difficult to use normalized tissue weight to make meaningful comparisons of tissue properties among different cartilage specimens. Therefore, in subsequent figures, we choose to plot Pc, $\pi_{PG}$ and other quantities of interest against tissue hydration, (Vt-Vc)/Vc, as defined in Eq. (8).

FIG. 15 shows a comparison of plots of Pc and $\pi_{PG}$ vs (Vt-Vc)/Vc for a normal 55 year old and an OA specimen. For the normal specimen, equilibrium in the absence of osmotic loading occurs at a low hydration, (Vt-Vc)/Vc= 4.87, whereas for the OA specimen, equilibrium in the absence of loading occurs at the high hydration, (Vt-Vc)/ Vc=10.92, which represents more than a two-fold increase in the ratio of total tissue water per dry weight in the OA specimen (see Table of FIG. 11). In considering the relative equilibrium stiffness of unloaded normal and OA cartilage, it is useful to compute the differences in the slopes between Pc vs (Vt-Vc)/Vc and $\pi_{PG}$ vs (Vt-Vc)/Vc (41). For the normal specimen, this difference is 11.6 atm per percentage change in hydration, whereas for the OA specimen this difference is 0.34 atm per percentage change in hydration. Another observation relating to tissue stiffness is the relative response of tissue hydration to a change in the ionic strength of the surrounding medium: In the normal tissue specimen, a change of 1 atm in $\pi_{PG}$ produces a change in volume of approximately 1.8% whereas in the OA tissue specimen, a smaller change in $\pi_{PG}$ (0.5 atm) produces a larger change in tissue volume of 10%. While we have obtained data from only one OA joint in the present study, these results are qualitatively consistent our previous findings on hydration and swelling based on a large number of studies of OA cartilage (e.g., (6, 7, 37, 42)).

FIG. 16 shows curves of Pc vs (Vt-Vc)/Vc measured in normal cartilage specimens of different ages. The results for two to seven specimens from each joint are included in the figure. While the curves represent tissues from widely differing age groups, they are qualitatively similar, both in shape and extent. The Table of FIG. 11 shows a statistically significant trend toward an increased equilibrium value of Pc with age consistent with previous findings (37, 43).

FIG. 16 shows that the collagen network does not become "limp" until approximately 25% of the initial tissue water has been expressed. Therefore, the hydration values over which the collagen network contribution cannot be ignored in the balance of forces, (i.e, that Pc>0), is significantly larger than was previously thought (e.g., (44, 45)).

FIG. 17 shows Pc vs (Vt-Vc)/Vc curves for 1) a normal specimen (90 years), 2) a specimen from the same 90 year old normal joint but treated with trypsin, and 3) an OA specimen. The mild trypsin treatment was aimed at reducing the GAG content to the level found in some of the OA specimens, while not affecting the collagen network. This treatment lowered the FCD by approximately 30–40% and decreased tissue volume by approximately 5%. The treated and untreated normal specimens show a similar dependence of Pc on hydration: however, owing to the reduction in the PG content of the treated specimens, the hydration ranges over which the stress titration is performed begins at a lower value than in the untreated specimens. Where the hydration levels of the treated and untreated normal specimens do coincide, so do the values of Pc. The similarity in the Pc vs (Vt-Vc)/Vc curves of the treated and untreated specimens, differing widely in FCD, shows that neither the FCD, nor the GAG content per se influences the stiffness of the collagen network. In addition, since FCD is known to affect the intrafibrillar water content, it appears that differences in the latter also do not influence the Pc vs (Vt-Vc)/Vc curve.

In contrast to the normal specimens, Pc vs (Vt-Vc)/Vc curves for OA specimens in FIG. 17 show a marked reduction in slope and a rightward shift to higher hydrations. The OA specimen corresponding to the curve with the shallowest slope has an FCD per dry weight similar to that found in normal native samples (see FIG. 11). The OA specimen from a neighboring region on the joint, corresponding to the curve with a steeper slope, has a lower FCD per dry weight, similar to that of the samples that have been trypsin treated. There is thus no relation between the shape of the Pc vs (Vt-Vc)/ Vc curve and the GAG-to-collagen ratio in the tissue. However, in a related preliminary study, aimed at determining the fraction of denatured collagen in normal and osteoarthritic cartilage, it was found that the same specimen showing the lowest slope of the Pc vs (Vt-Vc)/Vc curve contained the highest proportion of denatured collagen among a group of OA specimens (10).

Our OA data do not extend to a sufficiently low level of hydration to show the collagen network behavior in this regime, so is difficult to ascertain at what hydration Pc reaches zero, but there is an indication that $\pi_{PG}$ and thus Pc are overestimated in the OA specimens.

FIG. 11 shows equilibrium parameters characterizing the composition and state of the tissue.

DISCUSSION

We have developed a straightforward experimental methodology and a simple mathematical model for the determination of Pc, but it is essential to bear in mind that these experiments require considerable experience and care in handling the tissue specimens, especially in weighing them, as described in Methods.

Another cautionary reminder concerns calculating Pc by taking the difference of $\pi_{PG}$ and $\pi_{PEG}$ when these differences are small. It should be noted that pooled averaged data are used to calculate $\pi_{PG}$, in which small differences in KS/CS ratios were not taken into account. However, the age ranges of the cartilage used in the present study, and in the study in which the osmotic pressure of the isolated PGs was measured (ages 50–80), overlap to a large extent (Variability in the middle zone in the CS-to-KS ratio in this age range does not exceed 20%). In addition, for normal specimens, we have a reassuring indication that our calculated values of PPG are accurate, since, in the low hydration regime— where collagen tension should be close to zero—we find that the difference, $\pi_{PG}-\pi_{PEG}$, approaches zero as expected. This makes us feel more confident about the accuracy of our calculated values of Pc at higher hydrations, where collagen is in tension.

In the case of the OA specimens: we have at present no information about the specific characteristics of their $\pi_{PG}$ vs FCD curves, so we had to use PG data from normal tissue. However, we do know that KS/CS decreases in OA (36, 46), which should lead to a lowering of $\pi_{PG}$ for a given level of FCD as compared with PG from normal cartilage (23, 27). As a result, we may be overestimating $\pi_{PG}$ in OA specimens.

One of our goals for refining this methodology is to use PG extracted from each joint rather than PG extracted from many specimens. The availability of such data would improve the accuracy of the relationship between PG composition and osmotic pressure.

Physiological Implications

Our experimental results show that for normal unloaded cartilage at physiological ionic strength, the slope of Pc vs (Vt–Vc)/Vc is significantly steeper than that of $\pi_{PG}$ vs (Vt–Vc)/Vc at their point of intersection. Thus, the collagen network effectively fixes or "clamps" the equilibrium hydration to lie within a very narrow range despite large changes in PG osmotic pressure. This result helps us understand three important phenomena: First, it explains why excised normal cartilage plugs immersed in 0.15 NaCl show little initial swelling although the osmotic pressure gradients are altered as a result of removal from the intact joint (7). Second, we can similarly see why normal human cartilage swells by only 1%–2% (42) when it is transferred from physiological saline into hypotonic solution. Third, the stiffness of the collagen network ensures that in vivo, normal human cartilage maintains dimensional stability when small changes in proteoglycan content occur (such as in normal turnover); and conversely, it follows that if collagen stiffness is decreased (as in OA), the same variations in PG osmotic pressure cause the cartilage to swell or shrink by a larger amount.

Moreover, it is important to note that the shape of the Pc vs (Vt–Vc)/Vc curve largely determines the PG concentration at equilibrium by controlling the volume of the hydrated tissue—and not vice versa: In normal specimens, high PG concentration, high FCD, and high ($_{PG}$ can be developed owing to high collagen network stiffness. This means that during load-bearing, because of the high GAG osmotic pressure, changes in tissue thickness and chondrocyte volume will remain relatively small.

On the other hand, in OA specimens, for the same FCD per dry weight, (Vt–Vc)/Vc at equilibrium is approximately twice as high as in normal specimens, and the equilibrium FCD (proteoglycan concentration), and hence $FCD_{eff}$ are halved (see FIG. 11). As a result, OA tissue cannot develop a high PG concentration: Even if PG quantity (i.e., the ratio of PG-to-dry collagen) were to increase, the tissue would simply imbibe more water, and swell to a larger volume, without increasing PG concentration significantly. Hence, load bearing capacity of the tissue would not increase.

The trypsin treatment, which reduced the FCD per dry weight (see FIG. 11) to the lowest level found among our OA specimens, did not result in any discernible change in Pc vs (Vt–Vc)/Vc at equilibrium. Hence there was no increase in hydration, and therefore, the $FCD_{eff}$ was considerably higher than in the OA specimens at equilibrium (see FIG. 11).

In our present study, we have confirmed a previous finding that the equilibrium values of Pc=$\pi_{PG}$ increase with age (37) (43). This increase is likely due to an increase in the slope of Pc vs (Vt–Vc)/Vc with age, however, more data are required to assess adequately these trends and other characteristics of the collagen network with age.

Looking at the other side of the coin, while a stiff collagen network is essential to the adequate function of cartilage, excessive rigidity of the collagen network could render it brittle and hence more prone to failure from long-term fatigue. Now that we can measure Pc vs (Vt–Vc)/Vc quantitatively, it is also possible to measure the level of stiffness in cartilage (or of synthetic cartilage substitutes), and relate it to the quality of load bearing and fatigue resistance.

So far, we have discussed some physiological consequences of the stiffness of the collagen network in human articular cartilage. However, this work also raises crucial biochemical and structural questions which, for the time being, must be left unanswered: What specific molecular and ultrastructural factors give rise to human articular cartilage's singularly high resistance to swelling?; and how do these factors change during development, aging, and degeneration? We know that the "backbone" of the network consists of fibrillar assemblies of collagen II, with some collagen XI (47, 48). These molecules undergo post-translational changes with age, such as inter-molecular cross-links involving lysine and hydroxylysine residues and cross-links of the pentosidine type brought about by non-enzymatic glycation (49). These assemblies contain, in addition, a number of other molecular constituents such as collagen IX, decorin and fibromodulin (50). Some of these molecules are bound to the surface of the fibrils, as putative non-covalent supra-molecular cross-bridges (48, 50). Some of their side-chain substituents that may be involved in collagen cross-linking, may change with age (51). Ultimately, we would like to know what role these various constitutuents (and their interactions) play in determining the mechanical properties of the collagen network that we are now in a position to measure.

Another biological question worthy of further study is how the various enzymes affect the molecular organization and structure of the collagen network, and its gross mechanical properties? Since it is also possible by external treatment with specific enzymes or to modify specific network constituents by activating proteases, it is worthwhile to try to understand the mechanical consequences to the collagen network by these manipulations. We hope that our quantitative methodology will provide an effective tool for assessing the physiological implication of specific molecular changes of the above type, particularly in relation to the actual load-bearing function of the tissue.

Cartilage is not a Polyelectrolyte Gel

Because Pc vs (Vt−Vc)/Vc and $\pi_{PG}$ vs (Vt−Vc)/Vc are both monotonic functions of (Vt−Vc)/Vc, the equilibrium state of cartilage is a mechanically stable one—the tissue always returns to the equilibrium state after a departure from it. This property is crucial in order for cartilage to maintain its dimensional stability. Cartilage (as well as some man-made analogs such as reinforced concrete) would be poorly adapted for load bearing if they could assume a multiplicity of equilibrium volumes when subjected to a static load, which is the case for many non-electrolyte and polyelectrolyte gels (52). The latter can assume a multiplicity of equilibrium network volumes under the same thermodynamic equilibrium conditions. One fundamental difference between the architecture of cartilage and simple cross-linked polyelectrolyte gels is that in cartilage, the PG constituents that produce the osmotic pressure and the collagen network that resists it are largely independent (compare response of normal and normal trypsin-treated specimens in FIG. 17), whereas in polyelectrolytes and polyelectrolyte gels, they are chemically crosslinked. By separating the polyelectrolytes and elastic network phases, Nature may have precluded the possibility that cartilage exhibits possibly deleterious phase transitions.

Distinguishing Cartilage Matrix and Collagen Network Properties

It is important to contrast the behavior of the cartilage matrix and the collagen network under equilibrium isotropic loading. FIG. 14 shows the measured equilibrium curves Pc, $\pi_{PG}$, and $\pi_{PEG}$ vs $W/W_i$ for a normal cartilage specimen. $\pi_{PEG}$ vs $W/W_i$ represents the (isotropic) osmotic stress one would apply to deswell the tissue, whereas Pc vs $W/W_i$ represents the restraining pressure produced by the collagen network in tension at each $W/W_i$ in response to the applied load, and the PG swelling pressure. Additionally, though the relationship between $\pi_{PEG}$ vs $W/W_i$ is approximately linear for small tissue deformation about the unloaded equilibrium, this "aggregate" curve results from the balance of two highly non-linear stresses, the swelling stress of the PGs and the restraining stress exerted by the collagen network, neither of which is zero when the tissue is in an "unloaded" state.

Cartilage is not a Rock or a Soil

This distinction between the behavior of the aggregate tissue and its individual constituents, e.g., displayed in FIG. 14, shed light on existing biomechanical models of cartilage. Following McCutchen's seminal suggestion that when loaded, cartilage deforms by expressing or squeezing out water like a sponge or a soil (53), subsequent biomechanical models (54) have treated cartilage literally as a soil, consisting of a "pore fluid" phase and a single "elastic network" phase. Moreover, they have characterized the material properties of the cartilage matrix by using a constitutive law that is identical in form to one used to describe settlement or consolidation of rocks and soils (55). As our present study demonstrates, to understand the equilibrium swelling behavior of cartilage (and other extracellular matrices) requires separating its "solid" matrix phase into at least two constituents: the PGs that exert an osmotic pressure, and the collagen network that restrains them. The PG and collagen components of cartilage are structurally and compositionally distinct, they possess distinct physicochemical properties, and perform distinct physiological functions. Their aggregation into a single "solid-like" phase (54, 56) can obscure these differences. A biologically sensible constitutive law of the cartilage matrix should express its total stress tensor as a sum of (at least) collagen network and PG stress tensors, however, this decomposition is not possible with previously proposed constitutive laws of the cartilage matrix (54, 56).

Implications for the Unsteady State

Our findings have significant consequences for non-equilibrium loading regimes, particularly since the collagen network acts to restrain the PGs over a relatively wide range of hydrations. For example, in static loading, both in confined and unconfined compression, initially, the driving pressure (45) will be underestimated over the range in which the collagen network is in tension when using the D'Arcy equation as it is presently applied (e.g., (45)). In cyclic loading, both for small and large deformations, the non-linear collagen network contributions will be significant, both in compression and in recovery, particularly at small strains. These contributions are expected to be particularly relevant to load-bearing during locomotion, and will be affected by subsequent modifications in the collagen network associated with OA. The underestimation of the driving pressure also has significant implications to the dynamics of joint lubrication.

Appendix 1

Procedure for Determining Pc in Cartilage in Hypotonic Solutions

In essence, the method consists in finding, by trial and error, the PEG concentration in 0.015M NaCl (and hence $\pi_{PEG}$) which was just sufficient to shrink a given cartilage specimen to the same water content as it had in 0.15M NaCl, without PEG. The equilibrium in the swollen state in the presence of PEG is described by the equation:

$$Pc_{(o)}^{(0.015M)} + \pi_{PEG(o)}^{(0.015M)} = \pi_{PG(o)}^{(0.015M)}$$

If we assume Pc is a function of tissue volume alone, $Pc_{(o)}^{(0.015M)} = Pc_{(o)}^{(0.15M)}$, the latter quantity having already been determined. We also found that the osmotic pressures of PEG solution in 0.015M NaCl are the same as in 0.15 M NaCl (authors' unpublished data), therefore, we know $\pi_{PEG(o)}^{(0.015M)}$ from data in FIG. 8. Thus, we calculate $\pi_{PEG(o)}^{(0.015M)}$ from Eq. (A 1).

For normal specimens, the increase in water content due to swelling in 0.015 M NaCl is of the order of only 1% to 2%, so that the change in $FCD_{EFF}$ and hence in $\pi_{PG}$ from the unswollen state is very small and can be neglected: thus, we can assume that $\pi_{PG(SW)}^{(0.015M)} \sim \pi_{PG(o)}^{(0.015M)}$ and substitute the latter value into Eq. (A 1) to obtain $Pc_{(SW)}^{(0.015M)}$ corresponding to the increase in the tissue volume.

In the case of OA specimens, where the increase in hydration due to swelling in 0.015 M NaCl can reach 10%, one cannot assume $\pi_{PG(SW)}^{(0.015M)} \sim \pi_{PG(o)}^{(0.015M)}$. To estimate $\pi_{PG(o)}^{(0.015M)}$ we assume a linear relationship of $\pi_{PG}^{(0.015M)}$ vs hydration over the range of swelling in question and calculate $\pi_{PG(SW)}^{(0.015M)}$ from $\pi_{PG(o)}^{(0.015M)}$ in this manner.

References

1. Ogston, A. G. (1970) in Chemistry and Molecular Biology of the Intracellular Matrix: The biological functions of the glycosaminoglycans Eds.), pp. Academic Press, London.
2. Maroudas, A., Evans, H., and Almeida, L. (1973) Ann. Rheum. Dis. 32, 1–9.

3. Hjertquist, S. O. and Lemperg, R. C. (1972) Calcified Tissue Research 10, 223–237.
4. Bollet, A. J. and Nance, J. L. (1966) Journal of Clinical Investigations 45, 1170–1177.
5. Mankin, H. and Thrasher, A. Z. (1975) Journal of Bone and Joint Surgery 57A, 76–80.
6. Maroudas, A. and Venn, M. (1977) Ann Rheum Dis 36, 399–406.
7. Maroudas, A. (1976) Nature 260, 808–9.
8. Bonassar, L. J., Frank, E., and Murray, J. C. (1995) Arthritis and Rheumatism 38, 173–183.
9. Farquhar, T., Xia, Y., Burton-Wurster, N., Jelinski, L., and Lust, G., (1995) in Transactions of the 41st Annual Meeting of the ORS, Orlando, FL, 195.
10. Bank, R., Krikken, M., lafeber, F., and Te Koppele, J., (1996) in 42nd Annual Meeting of the ORS, Atlanta, 750.
11. Maroudas, A., Wachtel, E., Gmushko, G., Katz, E. P., and Weinberg, P. (1991) Biochim Biophys Acta 1073, 285–94.
12. Maroudas, A. (1980) in Studies in Joint Diseases: Metabolism of cartilagenous tissues: a quantitative approach (Maroudas, A. and Holborow, E. J., Eds.), pp. 59–86, Pitman Medical, London.
13. Libby, W. F., Berger, R., Mead, J. F., Alexander, G. V., and Ross, J. I. (1964) Science 146, 1170.
14. Kempson, G. E. (1980) in The Joints and Synovial Fluid: The mechanical properties of articular cartilage (Sokoloff, L., Eds.), pp. 177–237, Academic Press, New York.
15. Schmidt, M. B., Mow, V. C., Chun, L. E., and Eyre, D. R. (1990) J Orthop Res 8, 353–363.
16. Chun, L. E., Koob, T. J., and Eyre, D., (1986) in Transactions of the 32nd Annual Meeting of the ORS, New Orleans, 96.
17. Volpe, M. and Katz, E. P. (1991) J. Biomech. 28, 67–77.
18. Byers, P., Contemponi, C. A., and Farkas, T. A. (1970) Ann. Rheum. Dis. 29, 15–21.
19. Meachim, G. (1972) Ann. Rheum. Dis. 31, 457–464.
20. Bayliss, M. T., Venn, M., Maroudas, A., and Ali, S. Y. (1983) Biochem J 209, 387400.
21. Maroudas, A., Muir, H., and Wingham, J. (1969) Biochem. Biophys. Acta 177, 492–500.
22. Maroudas, A. and Grushko, G. (1990) in Methods in Cartilage Research: Measurement of Swelling Pressure of Cartilage (Maroudas, A. and Kuettner, K. E., Eds.), pp. 298–301, Academic Press, San Diego.
23. Erlich, S. (1994) The influence of age and degeneration on changes in the osmotic pressure of the proteoglycans in the intervertral disc, , 66.
24. Erlich, S., Maroudas, A., Schneiderman, R., Winlove, C. P., and Parker, K. (to be submitted 1997).
25. Parsegian, V. A., Rand, R. P., Fuller, N. L., and Rau, D. C. (1986) Methods of Enzymology 127, 400–416.
26. Wachtel, E. and Maroudas, A. (to be submitted 1997) Biochim. Biophys. Acta.
27. Urban, J. P., Maroudas, A., Bayliss, M. T., and Dillon, J. (1979) Biorheology 16, 447–64.
28. Schneiderman, R. and Maroudas, A. (1995) Archives of Biochemistry and Biophysics 324, 172.
29. Maroudas, A. and Thomas, H. (1970) Biochimica et Biophysica Acta 215, 214–216.
30. Urban, J. P., Holm, S., Maroudas, A., and Nachemson, A. (977) Clin Orthop, 101–14.
31. Edmond, E. and Ogston, A. G. (1968) Biochem J. 109, 569–576.
32. Miller, E. J., Narkates, A. J., and Niemann, M. A. (1990) Anal. Biochem. 190, 92–97.
33. Katz, E. P., Wachtel, E. J., and Maroudas, A. (1986) Biochim Biophys Acta 882, 136–9.
34. Wachtel, E., Maroudas, A., and Schfieiderman,;R. (1995) Biochim Biophys Acta 1243, 23943.
35. Leikin, S., Rau, D. C., and Parsegian, V. A. (1994) Proc. Natl. Acad. Sci. USA 91, 276–280.
36. Venn, M. and Maroudas, A. (1977) Ann Rheum Dis 36, 121–9.
37. Grushko, G., Schneidernan, R., and Maroudas, A. (1989) Connective Tissue Research 19, 149–176.
38. Fasman, G. D. (1975) Handbook of Biochemistry and Molecular Biology: Physical and Chemical Data, CRC Press, Boca Raton.
39. Ogston, A. G., Preston, B. N., and Wells, J. D. (1972) Proc. R. Soc. Lond. 333, 297–316.
40. Noda, H. (1972) J. Biochem. (Japan) 71, 699–703.
41. Basser, P. J. and Maroudas, A. (1997 (to be submitted)) Conn. Tiss. Res.
42. Maroudas, A., Ziv, I., Weisman, N., and Venn, M. (1985) Biorheology 22, 159–69.
43. Grushko, G. (1987) Age-related variations in some physical and chemical properties of articular cartilage, Master's Thesis, Technion, Haifa, 138.
44. Maroudas, A. and Bannon, C. (1981) Biorheology 18, 619–32.
45. Maroudas, A., Mizrahi, J., Benaim, E., Schneiderman, R., and Grusbko, G. (1992) in Mechanics of Swelling: Swelling Pressure of Cartilage: Roles Played by Proteoglycans and Collagen (Karlis, T. K., Eds.), pp. Springer-Verlag, Berlin.
46. Mankin, H. J. and Lippiello, L. (1971) Journal of Clinical Investigation 50, 1712.
47. Mendler, M., Eich-Bender, S. G., Vaughan, L., Winterhalter, K. H., and Bruckner, P. (1989) J. Cell. Biol. 108, 191–197.
48. Eyre, D., Wu, J. J., and Woods, P. (1992) in Articular Cartilage in Osteoarthritis: Cartilage-specific collagens: Structural studies (Kuettner, K. E., Schleyerbach, R., Peyron, J. G., and Hascall, V. C., Eds.), pp. Raven Press, New York.
49. Takahashi, M., Hoshino, H., Kushida, K., and Inoue, T. (1995) Ann. iochem. 232, 158–162.
50. Hedbom, E. and Heinegird, D. (1993) J. Biol. Chem. 268, 27307–27312.
51. Reinholdt, P. (1996) Personal Communication.
52. Tanaka, T. and Fillmore, D. J. (1978) J. Chem. Phys. 70, 1214–1218.
53. McCutchen, C. W. (1962) Wear 5, 1–17.
54. Mow, V. C., Kuei, S. C., Lai, W. M., and Armstrong, C. G. (1980) J. Biomech. Engng. 102, 73–84.
55. Rice, J. R. and Cleary, M. P. (1976) Rev. Geophys. Space Phys. 14, 227–241.
56. Lai, W. M., Hou, J. S., and Mow, V. C. (1991) J. Biomech. Eng. 113, 245–258.
57. Maroudas, A., Schneiderman, R., and Popper, 0. (1992) in Articular Cartilage and Osteoarthritis: The Role of Water, Proteoglycan, and Collagen in Solute Transport in Cartilage (Kuettner, K. E., Schleyerbach, R., Peyron, J. G., and Hascall, V. C., Eds.), pp. 351–371, Raven Press, Ltd., New York.

58. Maroudas, A., Bayliss, M. T., and Venn, M. F. (1980) Ann Rheum Dis 39, 514–23.

Thus, as illustrated through the preferred embodiment and the foregoing example, and as understood by further practicing the present invention, many advantages and attendant advantages are provided by the present invention.

This paper establishes an experimental and theoretical framework for treating the properties of the collagen network quantitatively: We are now able to measure Pc, the restraining stress exerted by the collagen network as function of collagen network hydration by varying the applied osmotic stress on the tissue such that the collagen network dilatation spans the range from being distended to being collapsed.

We have also clarified the role that the collagen network plays in determining tissue hydration, fixed charge density (FCD), tissue dimensional stability; and have suggested how collagen network properties influence both static and dynamic behavior of articular cartilage. One significant consequence of our simultaneous measurements of PG and collagen network properties is that it can help answer whether hydration changes in OA cartilage are caused by a loss of PGs or of collagen network integrity. Our data suggest the latter.

In particular, in accordance with the present invention, we view cartilage tissue matrix as a composite medium in which PGs are sequestered in mechanically coupled, but distinct collagenous dialysis sacks. This compels us to treat the collagen network and PG phases separately. However, in doing so, changes in their individual properties can be readily examined both qualitatively and quantitatively as well as their collective effect on the cartilage tissue matrix. A simple model readily permits us to explore the effects of changes in independent variables on dependent variables: $m_{EFHO2}^{eq}$, $m_{IFH2O}^{eq}$, $P_{PG}^{eq}$, $FCD_{eff}^{eq}$, $_{and}Pc^{eq}$. However, one should keep in mind that the model of cartilage behavior is inherently coupled—changes in one independent variable effect all dependent variables.

Mechano-osmotic titration is a powerful experimental methodology for studying the behavior of connective tissues, such as cartilage. It entails applying an osmotic pressure on a tissue whose collagen network is not fully distended, measuring the resulting Pc, the hydrostatic pressure the collagen network exerts in tension as function of collagen network hydration. Equilibrium isotropic loading using osmotic stress also represents the simplest mechanical loading regimen one could apply to tissue. Its use has leads to new insights into collagen network and PG behavior. Moreover, the model we present here to describe PG and collagen network behavior in isotropic loading is simple to implement graphically or solve numerically. This simplicity is achieved, in part, by combining conservation laws (e.g., conservation of momentum and charge) that must hold, with phenomenological equations of state (or constitutive laws) that must be carefully measured.

It is important to note that the model itself represents a relationship between macroscopic dependent variables such as $P_{PG}^{eq}$ and $Pc^{eq}$, and physical/chemical or ultrastructural characteristics of the cartilage matrix constituents, such as the virial coefficients of the PG solution, and collagen fibril spacing (that enters into the fitted function in Eq. (5)). Although symbolic expressions for each of the dependent variables in equilibrium could not be found, it is still possible to assess the influence of individual physical/chemical or ultrastructural characteristics of the cartilage matrix constituents on them, as well as how changes in these parameters (e.g., owing to experimental error or intersubject variation) influence changes in each of the dependent variables in equilibrium. However, it is clear that more research should be directed to relate macroscopically measured variables to macromolecular physical/chemical characteristics and ultrastructural parameters of connective tissues.

Our use of an empirical equation of state, such as $\pi_{PG}$ vs FCD, is a necessity, as there is no theory that adequately predicts the entropic and electrostatic interactions measured among PGs in solution. There is presently no adequate microstructural or micromechanical model of the collagen network from which we can derive Pc vs V, or from which we can infer the tensile stress distribution within the collagen fibrils at each degree of collagen network 'inflation' or state of deformation. (Interestingly, one would need to use an ultrastructural scale model to infer the stress distribution within the collagen network even if we know the hydrostatic pressure the network exerts on the PGs. We can understand why by again considering the inflation of a balloon, in which Laplace's law describes the relationship between the tensile stress developed within the membrane and the pressure the balloon supports. Without knowing the geometry of the balloon (e.g., the membrane thickness and radius) it is impossible to relate the pressure it exerts to the stress developed within the membrane.) Such a model would be useful since it would be possible to use it to estimate the tensile stresses developed within the collagen network caused by opposing the osmotic pressure exerted on the PGs.) There is also no molecular scale model that adequately predicts the relationship between intrafibrillar water content and net osmotic pressure, nor is there even a model that adequately predicts the form of $P_{PG}$ vs PEG concentration. Deriving these useful empirical relationships from basic principles is necessary if we are ever to understand the fundamental physical and chemical bases of cartilage behavior.

In accordance with the present invention, the novel combination of an osmotic titration experiment and a physical-chemical based model of cartilage swelling is rooted in Ogston's novel idea that at a macromolecular length scale, PGs produce an osmotic pressure that tends to swell cartilage, and the collagen network resists it. The balance between these two physically and chemically distinct constituents of cartilage, with distinct physiological functions, and distinct roles in the etiology of extracellular matrix pathologies, is essential to explaining cartilage Behavior, as well as other connective tissues.

Since it is necessary to incorporate the contributions of the collagen network and PG phases separately to describing the mechano-chemical behavior of cartilage, it is possible to develop a new constitutive relationship for the cartilage matrix that preserves the individual contributions of the PGs and collagen network. Such a model of tissue behavior could easily be incorporated into existing poroelastic or mixture theory models in order to describe the steady and unsteady behavior of cartilage under various loading conditions, lubrication, load bearing, and electromechanical processes. Such a model would finally synthesize and reconcile Ogston's and McCutchen's views of cartilage.

Although the above description provides many specificities, these enabling details should not be construed as limiting the scope of the invention, and it will be readily understood by those persons skilled in the art that the present invention is susceptible to many modifications, adaptations, and equivalent implementations without departing from this scope and without diminishing its attendant advantages. It is therefore intended that the present invention is not limited to the disclosed embodiments but should be defined in ccordance with the claims which follow.

We claim:

1. A method for determining the mechanical integrity of a collagen network in a tissue, said collagen network containing a moiety that exerts an osmotic pressure counteracted by a recoil pressure of the collagen network, the method comprising:

applying a known stress to the tissue;

measuring a quantity representing a hydration of the tissue; and providing the recoil pressure according to the known stress and to a second quantity representing an independently determined osmotic pressure of said moiety at said hydration.

2. The method according to claim 1, wherein said recoil pressure is provided for a plurality of applied known stresses to the tissue.

3. The method according to claim 1, wherein said recoil pressure is provided for a plurality of hydrations.

4. The method according to claim 1, wherein said known stress is applied by dialyzing the tissue against a solution of known osmotic pressure.

5. The method according to claim 1, further comprising assessing changes in moiety characteristics or collagen network characteristics in response to a stimulus or treatment.

6. The method according to claim 1 wherein said independently determined osmotic pressure is determined according to measurements of moiety osmotic pressure dependence on moiety fixed charge density and to measurements of intra-fibrillar and extra-fibrillar water content determined by x-ray analysis.

7. A method for determining the mechanical integrity of a tissue construct having a network containing a moiety that exerts an osmotic pressure counteracted by a recoil pressure of the network, the method comprising:

applying a known stress to the tissue construct;

measuring a quantity representing a hydration of the tissue construct; and providing the recoil pressure according to the known stress and to a second quantity representing an independently determined osmotic pressure of said moiety at said hydration.

8. The method according to claim 7, wherein said network is collagen, and wherein said moiety includes proteoglycans.

9. A method for identifying pathology in cartilage, comprising the steps of:

measuring the relationship between collagen network recoil pressure and hydration for said cartilage sample;

identifying pathology according to said relationship.

10. The method according to claim 9, wherein said step of identifying pathology includes comparing the measured relationship with corresponding relationships obtained for known normal or known pathological cartilage samples.

11. The method according to claim 9, wherein said step of identifying pathology is based on the stiffness of said collagen network as represented by the slope of said relationship.

12. A method for obtaining a bulk modulus for modeling cartilage, comprising the steps of:

modeling collagen recoil pressure and proteoglycan osmotic pressure; and relating the bulk modulus to a proteoglycan phase and to a collagen network phase.

13. The method according to claim 1, wherein said tissue is cartilage and said moiety includes a proteoglycan.

* * * * *